(12) United States Patent
Hille et al.

(10) Patent No.: US 9,549,903 B2
(45) Date of Patent: Jan. 24, 2017

(54) TRANSDERMAL DELIVERY SYSTEM COMPRISING BUPRENORPHINE

(71) Applicant: Purdue Pharma L.P., Stamford, CT (US)

(72) Inventors: Thomas Hille, Neuwied (DE); Gabriel Wauer, Bad Neuenahr-Ahrweiler (DE); Kevin John Smith, Cambridge (GB); Helen Elizabeth Johnson, Cambridge (GB); Gillian Elizabeth Mundin, Cambridge (GB)

(73) Assignee: PURDUE PHARMA L.P., Stamford, CT (US)

( * ) Notice: Subject to any disclaimer, the term of this patent is extended or adjusted under 35 U.S.C. 154(b) by 0 days.

(21) Appl. No.: 14/992,122

(22) Filed: Jan. 11, 2016

(65) Prior Publication Data

US 2016/0120823 A1    May 5, 2016

Related U.S. Application Data

(63) Continuation of application No. 14/364,192, filed as application No. PCT/IB2012/002973 on Dec. 12, 2012.

(60) Provisional application No. 61/569,609, filed on Dec. 12, 2011.

(51) Int. Cl.
   *A61K 9/70*     (2006.01)
   *A61K 31/485*   (2006.01)
   *A61K 47/12*    (2006.01)
   *A61K 31/4748*  (2006.01)

(52) U.S. Cl.
   CPC ........... *A61K 9/7069* (2013.01); *A61K 9/7053* (2013.01); *A61K 31/4748* (2013.01); *A61K 31/485* (2013.01); *A61K 47/12* (2013.01); *A61K 9/7084* (2013.01)

(58) Field of Classification Search
   CPC .................................................. A61K 9/7023
   See application file for complete search history.

(56) References Cited

U.S. PATENT DOCUMENTS

| | | | |
|---|---|---|---|
| 3,433,791 A | 3/1969 | Bentley | |
| 4,806,341 A | 2/1989 | Chien | |
| 5,240,711 A | 8/1993 | Hille et al. | |
| 5,968,547 A * | 10/1999 | Reder | A61K 9/0019 424/448 |
| 6,264,980 B1 | 7/2001 | Hille et al. | |
| 6,344,212 B2 | 2/2002 | Reder | |
| 6,783,769 B1 | 8/2004 | Arth et al. | |
| 7,390,500 B2 | 6/2008 | Muller | |
| 9,289,397 B2 | 3/2016 | Wright | |
| 9,308,202 B2 | 4/2016 | Hille et al. | |
| 2001/0002259 A1 | 5/2001 | Reder | |
| 2004/0081685 A1 | 4/2004 | Wright | |
| 2004/0126416 A1 | 7/2004 | Reidenberg | |
| 2004/0202710 A1 | 10/2004 | Muller | |
| 2004/0228906 A1 | 11/2004 | Bartholomaeus | |
| 2005/0118245 A1 | 6/2005 | Wilsmann | |
| 2005/0191340 A1 | 9/2005 | Bartholomaeus | |
| 2006/0148364 A1 | 7/2006 | Pohlmann | |
| 2008/0113013 A1 | 5/2008 | Koch | |
| 2010/0119585 A1 * | 5/2010 | Hille | A61K 9/7084 424/449 |
| 2014/0363487 A1 | 12/2014 | Hille | |
| 2015/0306093 A1 | 10/2015 | Wauer | |
| 2016/0008294 A1 | 1/2016 | Hille et al. | |
| 2016/0120823 A1 | 5/2016 | Hille et al. | |
| 2016/0175447 A1 | 6/2016 | Hille et al. | |

FOREIGN PATENT DOCUMENTS

| | | |
|---|---|---|
| DE | 39 39 376 C1 | 5/1991 |
| DE | 199 58 554 A1 | 1/2001 |

(Continued)

OTHER PUBLICATIONS

Chien "Transdermal Controlled System Medications", Marcel Dekker Inc., 1987, pp. 36-45.
European Pat Appln. 12 826 670.7 (based on PCT Application No. PCT/IB2012/002973)—Third party submission dated May 24, 2015.
European Pat. Appln. No. 14 171 110.1 (Pub. No. 2 810 646) (corresponds to PCT Application No. PCT/EP2014/061567)—Response to Third Party Submission dated Jun. 12, 2015.

(Continued)

*Primary Examiner* — Robert A Wax
*Assistant Examiner* — Amanda Heyes
(74) *Attorney, Agent, or Firm* — Jones Day

(57) ABSTRACT

The invention relates to transdermal therapeutic system for the transdermal administration of buprenorphine, comprising a buprenorphine-containing self-adhesive layer structure comprising
 A) a buprenorphine-impermeable backing layer, and
 B) a buprenorphine-containing pressure-sensitive adhesive layer on said buprenorphine-impermeable backing layer, the adhesive layer comprising
  a) at least one polymer-based pressure-sensitive adhesive,
  b) an analgesically effective amount of buprenorphine base or a pharmaceutically acceptable salt thereof, and
  c) a carboxylic acid selected from the group consisting of oleic acid, linoleic acid and linolenic acid, levulinic acid and mixtures thereof, in an amount sufficient so that said analgesically effective amount of buprenorphine is solubilized therein to form a mixture, and the carboxylic acid buprenorphine mixture forms dispersed deposits in the said pressure-sensitive adhesive,
wherein said buprenorphine-containing pressure-sensitive adhesive layer is the skin contact layer.

28 Claims, 5 Drawing Sheets

(56) References Cited

FOREIGN PATENT DOCUMENTS

| | | |
|---|---|---|
| DE | 10 2004 062 647 A1 | 6/2006 |
| DE | 10 2004 062 614 A1 | 7/2006 |
| EP | 0 368 409 A2 | 5/1990 |
| EP | 0 430 019 A2 | 6/1991 |
| EP | 0 430 019 B1 | 3/1996 |
| EP | 1 572 167 A1 | 9/2005 |
| EP | 0 964 677 B1 | 8/2006 |
| EP | 1 731 152 A2 | 12/2006 |
| GB | 1136214 | 12/1968 |
| JP | 2000-511936 A | 9/2000 |
| JP | 2003-503445 | 1/2003 |
| JP | 2003-522144 | 7/2003 |
| RU | 2251413 | 5/2005 |
| RU | 2005132834 A | 4/2006 |
| WO | WO 96/19975 | 7/1996 |
| WO | WO 98/36728 A | 8/1998 |
| WO | WO 01/01967 | 1/2001 |
| WO | WO 01/58447 | 8/2001 |
| WO | WO 03/018071 | 3/2003 |
| WO | WO 03/079962 | 10/2003 |
| WO | WO 2004/014336 A | 2/2004 |
| WO | WO 2004/054553 A1 | 7/2004 |
| WO | WO 02/41878 | 5/2005 |
| WO | WO 2006/030030 | 3/2006 |
| WO | WO 2014/195352 A1 | 12/2014 |

OTHER PUBLICATIONS

European Pat. Appln. No. 14 171 110.1 (Pub. No. 2 810 646) (corresponds to PCT Application No. PCT/EP2014/061567)—Third Party Submission dated May 8, 2015.
European Pat. Appln. No. 14 171 110.1 (Pub. No. 2 810 646) (corresponds to PCT Application No. PCT/EP2014/061567)—Communication re: European Search Report dated Aug. 21, 2014.
*Fachinformation* TRANSTEC, 2001, Bundesvethand der Pharmazeutishen Inudtrie e. V. (in German w/ English translation).
*Gebrauchsinformation: Information für den Anwender, Transtec 35 Mikrogramm/h—transdermales Pflaster, Version 5.0m* Nov. 18, 2010 (in German with English translation of p. 8, last paragraph (item 6) to p. 9, first paragraph of the Summary of Product Characteristics of Transtec 35 micrograms/hr (Transtec SPC)).
Highlights of Prescribing Information—Butrans (buprenorphine) Transdermal System—Aug. 2010.
Highlights of Prescribing Information—Butrans (buprenorphine) Transdermal System—Jun. 2010.
Kandavilli, S. "Polymers n Transdermal Drug Delivery Systems", *Pharmaceutical Technology*, May 2002, pp. 62-80.
Merck Index "An encyclopedia of chemicals, drugs, and biological",15th Edition, p. 264 (buprenorphine).
Napp Pharmaceuticals Limited, BuTrans 5, 10 and 20 ug/h Transdermal Patch—Summary of Product Characteristics, Mar. 11, 2010.
PCT Application No. PCT/EP2007/09622—International Preliminary Report on Patentability (IPRP) and Written Opinion of IPRP (WO-IPRP) from EPO as International Search Authority (in German) dated Jun. 10, 2009 (with English translation).
PCT Application No. PCT/EP2007/09622—International Search Report dated Jul. 18, 2008.
PCT Application No. PCT/EP2013/076325—International Search Report (ISR) and Written Opinion from EPO as International Search Authority dated May 13, 2014.
PCT Application No. PCT/EP2013/076325—International Preliminary Report on Patentability dated Jun. 16, 2015 with Written Opinion from EPO as International Search Authority.
PCT Application No. PCT/EP2014/061567—International Search Report (ISR) and Written Opinion from EPO as International Search Authority dated Aug. 21, 2014.
PCT Application No. PCT/IB2012/002973—International Preliminary Report on Patentability (IPRP) and Written Opinion from EPO as International Search Authority, Jun. 17, 2014.
Posker, GL "Buprenorphine 5, 10 and 20 µg/h Transdermal Patch—A review of Its Use in the Management of Chronic Non-Malignant Pain," Adis International Ltd, Drugs, Dec. 1, 2011, 71(18).
Transdermanye terapevti' cheskie sistemy (Transdermal Therapeutic System), http://medi.ru/doc/991011.htm, 2001 (in Russion with English translation).
Transtec 35, 52.5 and 70 micrograms transdermal patch—Summary of Product Characteristics, Nov. 10, 2014.
PCT Application No. PCT/EP2007/09622—International Preliminary Report on Patentability (IPRP) and Written Opinion of ISA Jun. 10, 2009.
Roy et al., "Transdermal Delivery of Buprenorphine through Cadaver Skin", Journal of Pharmaceutical Sciences, vol. 83, No. 2 Feb. 1994, pp. 126-130.
Rustan et al., "Fatty Acids: Structures and Properties", Encyclopedia of Life Sciences 2005, John Wiley & Sons, pp. 1-7.
Chilean Appln. No. 001559-2014—Notification of Oppositions dated Jan. 23, 2015 (in Spanish with English translation).
Chilean Appln. No. 001559-2014—Opposition dated Dec. 2, 2014 by Asociacion Industrial de Laboratorios Farmaceuticos AG (in Spanish with English translation).
Chilean Appln. No. 001559-2014—Opposition dated Dec. 9, 2014 by Laboratorios Recalcine SA (in Spanish with English translation).
Chilean Appln. No. 001559-2014—Response with attachments dated Mar. 23, 2015 to Oppositions by Asociacion Industrial de Laboratorios Farmaceuticos AG and Laboratorios Recalcine SA (in Spanish with English translation of Response).
Colombian Appln. No. 14.149.730—Opposition by Laboratorio Franco Colombiano SAS Lafrancol SAS, publication in Gazette 700 dated Jul. 21, 2014 (in Spanish with English translation).
Colombian Appln. No. 14.149.730—Response dated Jan. 21, 2015 to Opposition by Laboratorio Franco Colombiano SAS Lafrancol SAS (in Spanish with English translation).
Correa, Carlos, "Pautas para el examen de patentes farmaceuticas. Una perspectiva desde Ia Salud Publica" ("Guidelines for the examination of pharmaceutical patents" Developing a public health perspective), Universidad de Buenos Aires, Mar. 2008 (in Spanish with English translation of Foreword, pp. vii-viii).
ROMPP Online, Version 3.27, "Emulsionen", Sep. 6, 2012, Angsgar Behler (ed.) (in German with English translation).
Falbe, J., ROMPP Chemie Lexikon, (1990), Georg Thieme Verlag Stuttgart, pp. 1158-1159 (in German with English translation).
Liao, et al., "In Vitro Skin Permeation of Buprenorphine Transdermal Patch," J. Food and Drug Analysis, vol. 16, No. 6 (2008) pp. 8-15.
Indian Patent Appln. No. 2662/CHENP/2009—Pre-Grant Opposition dated Jan. 8, 2016 by Indian Pharmaceutical Alliance.
Chilean Patent Appln. No. 2015-001577—Pre-Grant Opposition dated Feb. 9, 2016 by Asociacion Industrial de Labomtorios Farmaceuticos AG (ASILFA) (in Spanish with English translation).
Chilean Patent Appln. No. 2015-001577—Applicant's Response dated Apr. 12, 2016 to Pre-Grant Opposition by Asociacion Industrial de Laboratorios Farmaceuticos AG (ASILFA) with Amended Claims (in Spanish with English translation).

* cited by examiner

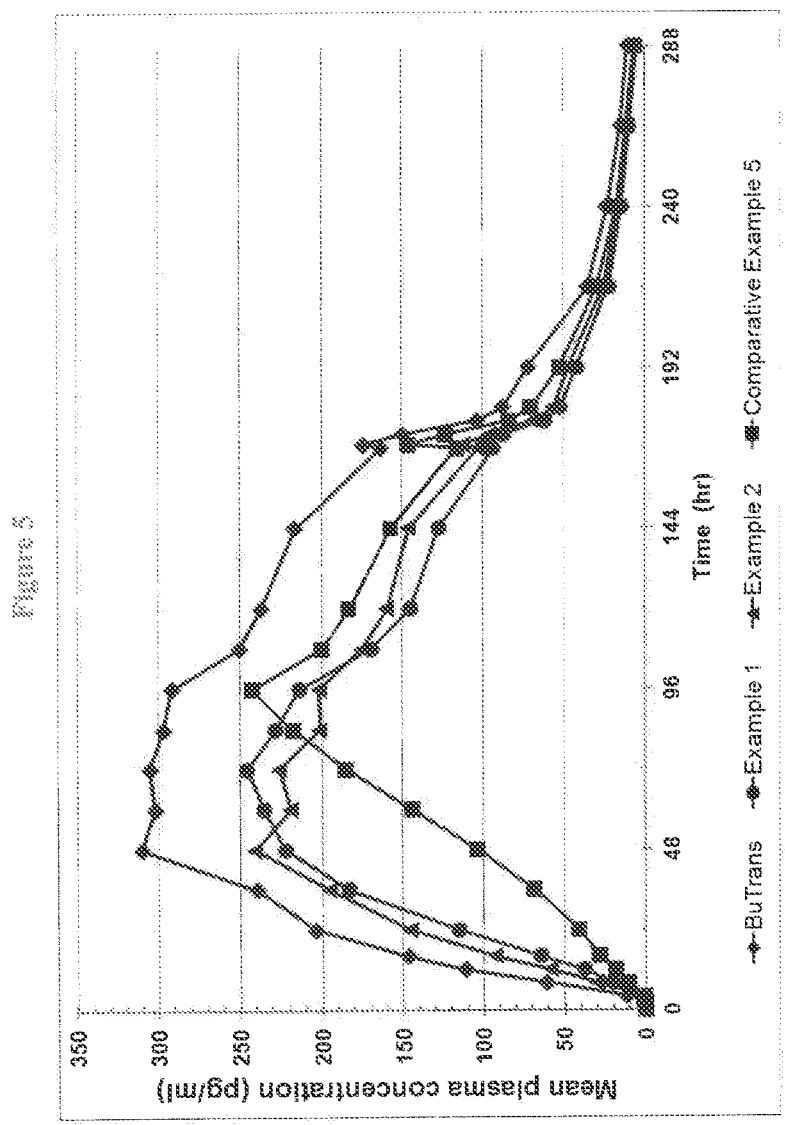

TRANSDERMAL DELIVERY SYSTEM COMPRISING BUPRENORPHINE

This application claims priority benefit of U.S. application Ser. No. 14/364,192, filed Jun. 10, 2014, which claims priority benefit of International Patent Application No. PCT/IB2012/002973, filed Dec. 12, 2012, which claims benefit of U.S. Provisional Application No. 61/569,609, filed Dec. 12, 2011, the disclosures of which are herein incorporated by reference in their entireties.

TECHNICAL FIELD OF THE INVENTION

The present invention relates to a transdermal therapeutic system (TTS) for the transdermal administration of buprenorphine, and processes of manufacture, uses thereof, and corresponding methods of treatment therewith.

BACKGROUND OF THE INVENTION

The active ingredient buprenorphine (5R,6R,7R,9R,13S,14S)-17-Cyclopropylmethyl-7-[(S)-3,3-dimethyl-2-hydroxybutan-2-yl]-6-methoxy-4,5-epoxy-6,14-ethanomorphinan-3-ol) is a partially synthetic opiate with high potency. Cancer patients may be treated with daily doses of around 1 mg. Despite its rather high molecular weight of 467.64 daltons, it is currently used for transdermal administration. The commercial TTS product Norspan®, also known as BuTrans®, delivers buprenorphine to the skin sufficiently to treat patients in pain for a time period of 7 days (about 168 hours) and allows therefore a use of the TTS over a time period of 7 days and allows in a fixed dosing regimen a once-weekly TTS exchange. This is specifically beneficial in terms of convenience and patient compliance. Thus the overall efficacy of the pain medicament is enhanced. However, the long administration periods may cause problems with skin irritation, which in combination with the considerable size (i.e., area of release) of the TTS may be problematic. Also, the large amount of excess drug in the TTS necessary to sustain enough driving force for sustaining the appropriate drug delivery over the long period of time is costly and has the potential to be subject to illicit use.

It is therefore desirable to reduce the overall size (i.e., area of release) of the TTS as well as the total amount of buprenorphine in the TTS before administration and also the amount remaining in the TTS after proper use, the residual amount. Thereby, the amount of drug available for illicit use (before and after proper use), and the amount to be wasted after proper use are both reduced. US Patent Application No. 2010/0119585 describes a certain TTS size and amount of drug reduction in comparison with the commercial TTS product Transtec® approved for an up-to-4 days administration regimen. Thus, the TTS needs to be replaced after 4 days at the latest. It is recommended to change Transtec® twice a week always on the same days at specific times, e.g. Monday mornings and Thursday evenings.

For convenience reasons it is, however, desirable to maintain the once weekly exchange mode (7 day dosing regimen) as, e.g., provided by the commercial product Norspan® instead of the every three to four days exchange mode as provided by, e.g., Transtec®.

All references and publications cited herein are hereby incorporated by reference in their enteritis for all purposes.

OBJECTS AND SUMMARY OF THE INVENTION

It is an object of certain embodiments of the present invention to provide a transdermal therapeutic system for the transdermal administration of buprenorphine (e.g., buprenorphine base), which requires a relatively small amount of buprenorphine (e.g., buprenorphine base) contained therein.

It is an object of certain embodiments of the present invention to provide a transdermal therapeutic system for the transdermal administration of buprenorphine (e.g., buprenorphine base) which requires a relatively small area of release.

It is an object of certain embodiments of the present invention to provide a transdermal therapeutic system for the transdermal administration of buprenorphine (e.g., buprenorphine base) providing a release suitable for providing pain relief for about 168 hours (corresponding to 7 days or one week).

These objects and others are accomplished by the present invention, which according to one aspect relates to a transdermal therapeutic system for the transdermal administration of buprenorphine (e.g., buprenorphine base), comprising a buprenorphine (e.g., buprenorphine base) containing self-adhesive layer structure comprising A) a buprenorphine (e.g., buprenorphine base) impermeable backing layer, and B) a buprenorphine (e.g., buprenorphine base) containing pressure-sensitive adhesive layer on said buprenorphine-impermeable backing layer, the adhesive layer comprising
  a) at least one polymer-based pressure-sensitive adhesive,
  b) an analgesically effective amount of buprenorphine base or a pharmaceutically acceptable salt thereof, and
  c) a carboxylic acid selected from the group consisting of oleic acid, linoleic acid, linolenic acid, levulinic acid and mixtures thereof, in an amount sufficient so that said analgesically effective amount of buprenorphine (e.g. buprenorphine base) is solubilized therein to form a mixture, and the carboxylic acid buprenorphine mixture forms dispersed deposits in said pressure-sensitive adhesive, wherein said buprenorphine-containing pressure-sensitive adhesive layer is the skin contact layer.

According to further aspects the invention relates to a method of treating pain in a patient by applying a transdermal therapeutic system in accordance with the invention to the skin of a patient, in particular to a method of treating pain in a patient by applying a transdermal therapeutic system in accordance with the invention to the skin of said patient for more than about 96 hours (or for more than 4 days), or for about 120 hours (or for 5 days), or for about 144 hours (or for 6 days) or for about 168 hours (or for 7 days or for one week).

According to one specific aspect, the invention relates to a method of treating pain in a patient by applying to the skin of said patient for about 168 hours (or for 7 days or for one week) a transdermal therapeutic system, comprising a buprenorphine (e.g., buprenorphine base) containing self-adhesive layer structure comprising A) a buprenorphine (e.g., buprenorphine base) impermeable backing layer, and B) a buprenorphine (e.g., buprenorphine base) containing pressure-sensitive adhesive layer on said buprenorphine-impermeable backing layer, the adhesive layer comprising
  a) at least one polymer-based pressure-sensitive adhesive, b) an analgesically effective amount of buprenorphine base or a pharmaceutically acceptable salt thereof, and c) a carboxylic acid selected from the group consisting of oleic acid, linoleic acid, linolenic acid, levulinic acid and mixtures thereof, in an amount sufficient so that said analgesically effective amount of buprenorphine (e.g., buprenorphine base) is solubilized therein to form a mixture, and the carboxylic acid buprenorphine mixture forms dispersed deposits in said pressure-sensitive adhesive, wherein said buprenorphine-containing pressure-sensitive adhesive layer is the skin contact layer.

According to one aspect, the invention relates to a transdermal therapeutic system for the transdermal administration of buprenorphine base, comprising a buprenorphine base-containing self-adhesive layer structure comprising A) a buprenorphine base-impermeable backing layer, and
B) a buprenorphine base-containing pressure-sensitive adhesive layer on said buprenorphine base-impermeable backing layer, the adhesive layer comprising
  a) at least one pressure-sensitive adhesive based on polysiloxane,
  b) an analgesically effective amount of buprenorphine base, and
  c) levulinic acid, in an amount sufficient so that said analgesically effective amount of buprenorphine base is solubilized therein to form a mixture, and the levulinic acid buprenorphine base mixture forms dispersed deposits in said pressure-sensitive adhesive, wherein said buprenorphine base-containing pressure-sensitive adhesive layer is the skin contact layer.

According to one aspect, the invention relates to a method of treating pain in a patient by applying to the skin of said patient for about 168 hours (or for 7 days or for one week) a transdermal therapeutic system, comprising a buprenorphine base-containing self-adhesive layer structure comprising A) a buprenorphine base-impermeable backing layer, and
B) a buprenorphine base-containing pressure-sensitive adhesive layer on said buprenorphine base-impermeable backing layer, the adhesive layer comprising
  a) at least one pressure-sensitive adhesive based on polysiloxane,
  b) an analgesically effective amount of buprenorphine base, and
  c) levulinic acid, in an amount sufficient so that said analgesically effective amount of buprenorphine base is solubilized therein to form a mixture, and the levulinic acid buprenorphine base mixture forms dispersed deposits in said pressure-sensitive adhesive, wherein said buprenorphine base-containing pressure-sensitive adhesive layer is the skin contact layer.

According to one aspect, the invention relates to a transdermal therapeutic system for the transdermal administration of buprenorphine, comprising a buprenorphine-containing self-adhesive layer structure comprising A) a buprenorphine-impermeable backing layer, and
B) a buprenorphine-containing pressure-sensitive adhesive layer on said buprenorphine-impermeable backing layer, the adhesive layer comprising
  a) at least one polymer-based pressure-sensitive adhesive,
  b) an analgesically effective amount of buprenorphine base or a pharmaceutically acceptable salt thereof, and
  c) a carboxylic acid selected from the group consisting of oleic acid, linoleic acid, linolenic acid, levulinic acid and mixtures thereof, in an amount sufficient so that said analgesically effective amount of buprenorphine is solubilized therein to form a mixture, and the carboxylic acid buprenorphine mixture forms dispersed deposits in said pressure-sensitive adhesive, wherein said buprenorphine-containing pressure-sensitive adhesive layer is the skin contact layer and contains more than about 0.55 mg/cm$^2$ or more than 0.6 mg/cm$^2$ of buprenorphine base or an equimolar amount of a pharmaceutically acceptable salt thereof.

According to one aspect, the invention relates to a method of treating pain in a patient by applying to the skin of said patient for about 168 hours a transdermal therapeutic system for the transdermal administration of buprenorphine, comprising a buprenorphine-containing self-adhesive layer structure comprising A) a buprenorphine-impermeable backing layer, and
B) a buprenorphine-containing pressure-sensitive adhesive layer on said buprenorphine-impermeable backing layer, the adhesive layer comprising
  a) at least one polymer-based pressure-sensitive adhesive,
  b) an analgesically effective amount of buprenorphine base or a pharmaceutically acceptable salt thereof, and
  c) a carboxylic acid selected from the group consisting of oleic acid, linoleic acid and linolenic acid, levulinic acid and mixtures thereof, in an amount sufficient so that said analgesically effective amount of buprenorphine is solubilized therein to form a mixture, and the carboxylic acid buprenorphine mixture forms dispersed deposits in the said pressure-sensitive adhesive, wherein said buprenorphine-containing pressure-sensitive adhesive layer is the skin contact layer and contains more than about 0.55 mg/cm$^2$ or more than 0.6 mg/cm$^2$ of buprenorphine base or an equimolar amount of a pharmaceutically acceptable salt thereof.

According to one aspect, the invention relates to a transdermal therapeutic system for the transdermal administration of buprenorphine base, comprising a buprenorphine base-containing self-adhesive layer structure comprising A) a buprenorphine base-impermeable backing layer, and
B) a buprenorphine base-containing pressure-sensitive adhesive layer on said buprenorphine base-impermeable backing layer, the adhesive layer comprising
  a) at least one pressure-sensitive adhesive based on polysiloxane,
  b) an analgesically effective amount of buprenorphine base, and
  c) levulinic acid, in an amount sufficient so that said analgesically effective amount of buprenorphine base is solubilized therein to form a mixture, and the levulinic acid buprenorphine base mixture forms dispersed deposits in the said pressure-sensitive adhesive, wherein said buprenorphine base-containing pressure-sensitive adhesive layer is the skin contact layer and contains more than about 0.55 mg/cm$^2$ or more than 0.6 mg/cm$^2$ buprenorphine base.

According to one aspect, the invention relates to a method of treating pain in a patient by applying to the skin of said patient for about 168 hours (or for 7 days or for one week) a transdermal therapeutic system comprising a buprenorphine base-containing self-adhesive layer structure comprising A) a buprenorphine base-impermeable backing layer, and
B) a buprenorphine base-containing pressure-sensitive adhesive layer on said buprenorphine base-impermeable backing layer, the adhesive layer comprising
   a) at least one pressure-sensitive adhesive based on polysiloxane,
   b) an analgesically effective amount of buprenorphine base, and
   c) levulinic acid, in an amount sufficient so that said analgesically effective amount of buprenorphine base is solubilized therein to form a mixture, and the levulinic acid buprenorphine base mixture forms dispersed deposits in the said pressure-sensitive adhesive, wherein said buprenorphine base-containing pressure-sensitive adhesive layer is the skin contact layer and contains more than about 0.55 mg/cm$^2$ or more than 0.6 mg/cm$^2$ buprenorphine base.

According to one aspect, the invention relates to a set of two to five different transdermal therapeutic systems for the transdermal administration of buprenorphine base selected from five different transdermal therapeutic systems, a first, a second, a third, a forth and a fifth transdermal therapeutic system, each of the five different transdermal therapeutic systems comprising a buprenorphine-containing self-adhesive layer structure comprising A) a buprenorphine base-impermeable backing layer, and
B) a buprenorphine base-containing pressure-sensitive adhesive layer on said buprenorphine base-impermeable backing layer, the adhesive layer comprising
   a) at least one pressure-sensitive adhesive based on polysiloxanes,
   b) an analgesically effective amount of buprenorphine base, and
   c) levulinic acid, in an amount sufficient so that said analgesically effective amount of buprenorphine base is solubilized therein to form a mixture, and the levulinic acid buprenorphine base mixture forms dispersed deposits in the said pressure-sensitive adhesive, wherein,
the first transdermal therapeutic system provides a size of said buprenorphine-containing pressure-sensitive adhesive layer providing the area of release ranging from about 1 cm$^2$ to about 4.8 cm$^2$ and contains from about 1 mg to about 4 mg buprenorphine base;
the second transdermal therapeutic system provides a size of said buprenorphine-containing pressure-sensitive adhesive layer providing the area of release ranging from about 3 cm$^2$ to about 9.5 cm$^2$ and contains an amount of from about 3.5 mg to about 8 mg buprenorphine base; and
the third transdermal therapeutic system provides a size of said buprenorphine-containing pressure-sensitive adhesive layer providing the area of release ranging from about 6 cm$^2$ to about 19 cm$^2$ and contains from about 6.5 mg to about 16 mg buprenorphine base; and
the fourth transdermal therapeutic system provides a size of said buprenorphine-containing pressure-sensitive adhesive layer providing the area of release ranging from about 12 cm$^2$ to about 28.5 cm$^2$ and contains from about 11.5 mg to about 24 mg buprenorphine base; and
the fifth transdermal therapeutic system provides a size of said buprenorphine-containing pressure-sensitive adhesive layer providing the area of release ranging from about 16 cm$^2$ to about 38 cm$^2$ and contains from about 15 mg to about 32 mg buprenorphine base, wherein the five different transdermal therapeutic systems have increasing areas of release and amounts of buprenorphine from the first to the fifth transdermal therapeutic system, in particular for use in method of treating pain by applying one of said transdermal therapeutic systems for about 168 hours on the skin of a patient.

According to one aspect, the invention relates to a transdermal therapeutic system comprising buprenorphine for the transdermal administration of buprenorphine selected from:
a first transdermal therapeutic system providing a size of the area of release ranging from about 1 cm$^2$ to about 4.8 cm$^2$ and containing an amount of said buprenorphine from 1 mg to about 4 mg buprenorphine base or an equimolar amount of a pharmaceutically acceptable salt thereof and providing a mean AUCt of more than 8,000 pg.hr/ml over about 168 hours of administration after a single-dose administration to a subject population;
a second transdermal therapeutic system providing a size of the area of release ranging from about 3 cm$^2$ to about 9.5 cm$^2$ and containing an amount of said buprenorphine from about 3.5 mg to about 8 mg buprenorphine base or an equimolar amount of a pharmaceutically acceptable salt thereof and providing a mean AUCt of more than 16,000 pg.hr/ml over about 168 hours of administration after a single-dose administration to a subject population; and
a third transdermal therapeutic system providing a size of the area of release ranging from about 6 cm$^2$ to about 19 cm$^2$ and containing an amount of said buprenorphine from about 6.5 mg to about 16 mg buprenorphine base or an equimolar amount of a pharmaceutically acceptable salt thereof and providing a mean AUCt of more than 32,000 pg.hr/ml over about 168 hours of administration after a single-dose administration to a subject population; and
a fourth transdermal therapeutic system providing a size of the area of release ranging from about 12 cm$^2$ to about 28.5 cm$^2$ and containing an amount of said buprenorphine from about 11.5 mg to about 24 mg buprenorphine base or an equimolar amount of a pharmaceutically acceptable salt thereof and providing a mean AUCt of more than 48,000 pg.hr/ml over about 168 hours of administration after a single-dose administration to a subject population; and
a fifth transdermal therapeutic system providing a size of the area of release ranging from about 16 cm$^2$ to about 38 cm$^2$ and containing an amount of said buprenorphine from about 15 mg to about 32 mg buprenorphine base or an equimolar amount of a pharmaceutically acceptable salt thereof and providing a mean AUCt of more than 64,000 pg.hr/ml over about 168 hours of administration after a single-dose administration to a subject population, in particular for use in method of treating pain by applying said selected transdermal therapeutic system for about 168 hours on the skin of a patient.

According to one aspect, the invention relates to a transdermal therapeutic system comprising buprenorphine for the transdermal administration of buprenorphine selected from:
a first transdermal therapeutic system providing a size of the area of release ranging from about 1 cm$^2$ to about 4.8 cm$^2$ and containing an amount of said buprenorphine from 1 mg to about 4 mg buprenorphine base or an equimolar amount of a pharmaceutically acceptable salt thereof and providing a nominal mean release rate of about 5 µg/hr over about 168 hours of administration;

a second transdermal therapeutic system providing a size of the area of release ranging from about 3 cm² to about 9.5 cm² and containing an amount of said buprenorphine from about 3.5 mg to about 8 mg buprenorphine base or an equimolar amount of a pharmaceutically acceptable salt thereof and providing a nominal mean release rate of about 10 µg/hr over about 168 hours of administration; and a third transdermal therapeutic system providing a size of the area of release ranging from about 6 cm² to about 19 cm² and containing an amount of said buprenorphine from about 6.5 mg to about 16 mg buprenorphine base or an equimolar amount of a pharmaceutically acceptable salt thereof and providing a nominal mean release rate of about 20 µg/hr over about 168 hours of administration; and a fourth transdermal therapeutic system providing a size of the area of release ranging from about 12 cm² to about 28.5 cm² and containing an amount of said buprenorphine from about 11.5 mg to about 24 mg buprenorphine base or an equimolar amount of a pharmaceutically acceptable salt thereof and providing a nominal mean release rate of about 30 µg/hr over about 168 hours of administration; and a fifth transdermal therapeutic system providing a size of the area of release ranging from about 16 cm² to about 38 cm² and containing an amount of said buprenorphine from 15 mg to about 32 mg buprenorphine base or an equimolar amount of a pharmaceutically acceptable salt thereof and providing a nominal mean release rate of about 40 µg/hr over about 168 hours of administration, in particular for use in method of treating pain by applying said selected transdermal therapeutic system for about 168 hours on the skin of a patient.

According to one aspect, the invention relates to a set of transdermal therapeutic systems including at least two transdermal therapeutic systems selected from the first, second, third, fourth and fifth transdermal therapeutic systems as described in the previous paragraphs.

According to one aspect, the invention relates to a method of treating pain in a patient by selecting for said patient the appropriate transdermal therapeutic system from the first, second, third, fourth and fifth transdermal therapeutic system as described in the previous paragraphs and subsequently applying said selected transdermal therapeutic system on the skin of said patient for about 168 hours.

According to one aspect, the invention relates to a transdermal therapeutic system comprising buprenorphine for the transdermal administration of buprenorphine, wherein buprenorphine is present in the form of buprenorphine base and providing a non-cumulative release of buprenorphine base as measured in a Franz diffusion cell with dermatomed human skin of 2 µg/cm² to 10 µg/cm² in the first 8 hours,
20 µg/cm² to 80 µg/cm² from hour 8 to hour 24,
20 µg/cm² to 80 µg/cm² from hour 24 to hour 32,
30 µg/cm² to 120 µg/cm² from hour 32 to hour 48,
40 µg/cm² to 150 µg/cm² from hour 48 to hour 72,
100 µg/cm² to 300 µg/cm² from hour 72 to hour 144, and
30 µg/cm² to 100 µg/cm² from hour 144 to hour 168, in particular for use in method of treating pain by applying the transdermal therapeutic system for about 168 hours on the skin of a patient.

According to one aspect, the invention relates to a transdermal therapeutic system comprising buprenorphine for the transdermal administration of buprenorphine, wherein buprenorphine is present in the form of buprenorphine base and providing a non-cumulative release of buprenorphine base as measured in a Franz diffusion cell with dermatomed human skin of 2 µg/cm² to 10 µg/cm² in the first 8 hours,
20 µg/cm² to 80 µg/cm² from hour 8 to hour 24,
20 µg/cm² to 80 µg/cm² from hour 24 to hour 32,
30 µg/cm² to 120 µg/cm² from hour 32 to hour 48,
40 µg/cm² to 150 µg/cm² from hour 48 to hour 72,
100 µg/cm² to 300 µg/cm² from hour 72 to hour 144, and
30 µg/cm² to 100 µg/cm² from hour 144 to hour 168, and comprising a buprenorphine base-containing self-adhesive layer structure comprising A) a buprenorphine base-impermeable backing layer, and
B) a buprenorphine base-containing pressure-sensitive adhesive layer on said buprenorphine base-impermeable backing layer, the adhesive layer comprising
   a) at least one polymer-based pressure-sensitive adhesive,
   b) an analgesically effective amount of buprenorphine base, and optionally
   c) a carboxylic acid selected from the group consisting of oleic acid, linoleic acid, linolenic acid, levulinic acid and mixtures thereof, in an amount sufficient so that said analgesically effective amount of buprenorphine base is solubilized therein to form a mixture, and the carboxylic acid buprenorphine base solution forms dispersed deposits in the said pressure-sensitive adhesive, wherein said buprenorphine base-containing pressure-sensitive adhesive layer is the skin contact layer, in particular for use in method of treating pain by applying the transdermal therapeutic system for about 168 hours on the skin of a patient.

Within the meaning of this invention, the term "transdermal therapeutic system" (or TTS) refers to the entire individual unit that is applied to the skin of a patient, and which comprises the buprenorphine-containing self-adhesive layer structure and optionally an additional larger active-free self-adhesive layer structure on top of the buprenorphine-containing self-adhesive layer structure, which TTS provides the percutaneous delivery of the active buprenorphine to the patient. During storage, such a TTS is normally located on a redetachable protective layer from which it is removed immediately before application to the surface of the patient's skin. A TTS protected this way may be stored in a blister pack or a side sealed bag.

Within the meaning of this invention, the term "buprenorphine-containing self-adhesive layer structure" refers to the active agent-containing structure providing the area of release of the active agent.

Within the meaning of this invention, "polymer-based pressure-sensitive adhesive" refers to a pressure-sensitive adhesive containing from 75% to 100% of said polymer based on the dry weight of the pressure-sensitive adhesive, e.g., 75% to 100% of polysiloxane. According to certain embodiments the pressure-sensitive adhesive contains from 80% to 100%, or from 85% to 100%, or from 90% to 100%, or from 95% to 100% of the polymer (e.g., polysiloxane) based on the dry weight of the pressure sensitive adhesive. A pressure-sensitive adhesive is in particular a material that adheres with finger pressure, is permanently tacky, exerts a strong holding force and should be removable from smooth surface without leaving a residue. Examples of useful pressure-sensitive adhesives based on polysiloxane which are commercially available include the standard Bio-PSA series (7-4400, 7-4500 and 7-4600 series), the amine compatible (endcapped) Bio-PSA series (7-4100, 7-4200 and 7-4300 series) and the Soft Skin Adhesives series (7-9800) manufactured by Dow Corning. Preferred pressure-sensitive adhesives based on polysiloxane are heptane-solvated pressure-sensitive adhesives including BIO-PSA 7-4201, BIO-PSA 7-4301, BIO-PSA 7-4501.

Within the meaning of this invention, the term "additional larger active agent-free self-adhesive layer structure" refers to a self-adhesive layer structure that is free of active agent and larger than the active agent-containing structure and providing additional area adhering to the skin, but no area of release of the active agent, and enhancing thereby the overall adhesive properties of the TTS.

Within the meaning of this invention, the term "buprenorphine-containing pressure-sensitive adhesive layer" and "matrix layer" have the same meaning and refer to the layer containing the active in a matrix-type structure of active in-adhesive.

Within the meaning of this invention, the term "skin contact layer" refers to the part of the TTS which is in direct contact with the skin of the patient during administration and is located in/co-extensive with the buprenorphine-containing self-adhesive layer structure. The sizes of the "skin contact layer" and the buprenorphine-containing self-adhesive layer structure are co-extensive and correspond to the area of release.

Within the meaning of this invention, the term "deposit" refers to distinguishable, e.g., visually distinguishable, areas within the pressure-sensitive adhesive. Such deposits are e.g., droplets. Deposits that are visually distinguishable may be identified by use of a microscope.

Within the meaning of this invention, the parameter "mean cumulative skin permeation rate" is provided in $\mu g/cm^2$-hr and is calculated from the cumulative release as measured by in vitro experiments carried out with the Franz diffusion cell over the total time period of release, e.g., 168 hours, in $\mu g/cm^2$ divided by the hours corresponding to said total time period of release, e.g., 168 hours.

Within the meaning of this invention, the parameter "mean non-cumulative skin permeation rate" is provided in $\mu g/cm^2$-hr and is calculated from the non-cumulative release of a certain sample interval as measured in a Franz diffusion cell in $\mu g/cm^2$ divided by the hours of said sample interval.

Within the meaning of this invention, the parameter "cumulative release" is provided in $\mu g/cm^2$ and relates to the total amount released over the total time period of release, e.g., 168 hours, as measured in a Franz diffusion cell. The value is a mean value of at least 3 experiments.

Within the meaning of this invention, the parameter "non-cumulative release" is provided in $\mu g/cm^2$ and relates to the amount released in a sample interval at certain elapsed time within the total time period of release, e.g., hour 16 of release corresponding to a sample interval of 8 hours from hour 8 to hour 16 of release within 168 hours of total time period of release, as measured in a Franz diffusion cell. The value is a mean value of at least 3 experiments.

Within the meaning of this invention, the parameter "mean release rate" refers to the mean release rate in $\mu g/hr$ over the period of administration (e.g., 7 days) by which the active agent permeates through the human skin into the blood system and is based on the AUC obtained over said period of administration in a clinical study.

Within the meaning of this invention, the parameter "nominal mean release rate" refers to an assigned mean release rate determined by comparison with the commercial reference product BuTrans® which is applied for 7 days to the skin of the subjects and of which mean release rates are publicly available from the package insert. The corresponding known nominal mean release rate of the 25 $cm^2$ area of release BuTrans® reference TTS containing 20 mg buprenorphine is 20 $\mu g/hr$. The mean release rate is proportional to the size of the area of release of a TTS and may be used to distinguish TTSs by the dosage strength. The BuTrans® TTS with half the size (i.e. 12.5 $cm^2$ area of release) and containing 10 mg of buprenorphine provides the known nominal mean release rate of 10 $\mu g/hr$. The BuTrans® TTS with a size of 6.25 $cm^2$ area of release and containing 5 mg of buprenorphine provides the known nominal mean release rate of 5 $\mu g/hr$. Accordingly, it can be assumed that a corresponding TTS with a size of 50 $cm^2$ area of release and containing 40 mg of buprenorphine provides a nominal mean release rate of 40 $\mu g/hr$, and a corresponding TTS with a size of 37.5 $cm^2$ area of release and containing 30 mg of buprenorphine provides a nominal mean release rate of 30 $\mu g/hr$. The nominal mean release rates are assigned to the TTSs in accordance with the invention based on bioequivalence considerations by at least comparing the mean AUCt of the reference TTS BuTrans® with the mean AUCt of the TTSs in accordance with the invention obtained in the same clinical study.

Within the meaning of this invention, the meaning of "by applying to the skin of said patient for about 168 hours" corresponds to "by applying to the skin of said patient for about 7 days or for one week" and refers to a once a week exchange mode or dosing regimen. Likewise, about 96 hours correspond to 4 days, about 120 hours correspond to 5 days and about 144 hours correspond to 6 days. The term "applying to the skin of a patient for a certain period of time" has the same meaning as "administration for a certain period of time".

Within the meaning of this invention, the term "patient" refers to a subject who has presented a clinical manifestation of a particular symptom or symptoms suggesting the need for treatment, who is treated preventatively or prophylactically for a condition, or who has been diagnosed with a condition to be treated.

If not indicated otherwise "%" refers to weight-%.

Within the meaning of this invention, the term "active", "active agent", and the like, as well as the term "buprenorphine" refers to buprenorphine base or a pharmaceutically acceptable salt thereof. Unless otherwise indicated the amounts of buprenorphine in the TTS relate to the amount of buprenorphine before administration of the TTS. The amounts of buprenorphine in the TTS after administration are referred to as residual amounts.

Within the meaning of this invention, values and ranges specifying the size of the area of release and the amount of buprenorphine contained in the transdermal therapeutic system are mean values of at least 3 measurements.

Within the meaning of this invention the term "pharmacokinetic parameters" refers to parameters describing the blood plasma curve, e.g. Cmax, AUCt and AUCINF obtained in a clinical study, e.g. by single-dose administration of the active agent TTS, e.g. the buprenorphine base TTS to healthy human subjects. The pharmacokinetic parameters of the individual subjects are summarized using arithmetic and geometric means, e.g. a mean Cmax, a mean AUCt and a mean AUCINF, and additional statistics such as the respective standard deviations and standard errors, the minimum value, the maximum value, and the middle value when the list of values is ranked (Median). In the context of the present invention, pharmacokinetic parameters, e.g. the mean Cmax, the mean AUCt and the mean AUCINF refer to geometric mean values if not indicated otherwise. It cannot be precluded that the absolute mean values obtained for a certain TTS in a clinical study vary to a certain extend from study to study. To allow a comparison of absolute mean values between studies, a reference formulation, e.g. the commercial reference product BuTrans® or in the future any product based on the invention, may be used as internal standard. A comparison of the AUC per area of release, e.g. the mean AUCt per area of release of the respective reference product in the earlier and later study can be used to obtain a correction factor to take into account differences from study to study.

Clinical studies according to the present invention refer to studies performed in full compliance with the International Conference for Harmonization of Clinical Trials (ICH) and all applicable local Good Clinical Practices (GCP) and regulations.

Within the meaning of this invention, the term "healthy human subject" refers to a male or female subject with a body weight ranging from 55 kg to 100 kg and a body mass index (BMI) ranging from 18 to 29 and normal physiological parameters, such as blood pressure, etc. Healthy human subjects for the purposes of the present invention are selected according to inclusion and exclusion criteria which are based on and in accordance with recommendations of the ICH.

Within the meaning of this invention, the term "subject population" refers to at least ten individual healthy human subjects.

Within the meaning of this invention, the term "geometric mean" refers to the mean of the log transformed data backtransformed to the original scale.

Within the meaning of this invention, the term "arithmetic mean" refers to the sum of all values of observation divided by the total number of observations.

Within the meaning of this invention, the parameter "AUC" corresponds to the area under the plasma concentration-time curve. The AUC value is proportional to the amount of active agent absorbed into the blood circulation in total and is hence a measure for the bioavailability.

Within the meaning of this invention, the parameter "AUCt" is provided in pg.hr/ml and relates to the area under the plasma concentration-time curve from hour 0 to the last measurable plasma concentration and is calculated by the linear trapezoidal method.

Within the meaning of this invention, the parameter "mean AUCt per area of release" is provided in pg.hr/ml-cm$^2$ and is calculated from the geometric mean AUCt as determined for a certain TTS in pg.hr/ml divided by the area of release of said TTS.

Within the meaning of this invention, the parameter "AUCINF" is provided in pg.hr/ml and relates to the area under the plasma concentration-time curve extrapolated to infinity and is calculated using the formula:

$$AUCINF = AUCt + \frac{CLast}{LambdaZ}$$

where CLast is the last measurable plasma concentration and LambdaZ is the apparent terminal phase rate constant.

Within the meaning of this invention, the parameter "Cmax" is provided in pg/ml and relates to the maximum observed blood plasma concentration of the active agent.

Within the meaning of this invention, the parameter "tmax" is provided in hr and relates to the time point at which the Cmax value is reached. In other words, tmax is the time point of the maximum observed plasma concentration.

Within the meaning of this invention, the parameter "LambdaZ" is provided in 1/hr and relates to the apparent terminal phase rate constant, where LambdaZ is the magnitude of the slope of the linear regression of the log concentration versus time profile during the terminal phase.

Within the meaning of this invention, the parameter "t½Z" is provided in hr and relates to the apparent plasma terminal phase half-life and is commonly determined as t½Z=(ln 2)/LambdaZ.

Within the meaning of this invention, the term "mean plasma concentration" is provided in pg/ml and is a mean of the individual plasma concentrations of active agent, e.g. buprenorphine base, at each point in time.

Within the meaning of this invention, the term "bioequivalent" is defined to refer to a TTS that provides geometric mean values of Cmax, AUCt, and AUCINF for buprenorphine, wherein the 90% confidence intervals estimated for the ratio test/reference fall within the range of 80.00% to 125.00%.

BRIEF DESCRIPTION OF THE DRAWINGS

FIG. 5 depicts the mean plasma concentration for Examples 1 and 2, Comparative Example 5 and BuTrans®. The area of release of the transdermal therapeutic systems according to Examples 1 and 2 being 10 cm$^2$, the area of release of the transdermal therapeutic systems according to Comparative Example 5 being 15 cm$^2$ and the area of release for BuTrans® being 25 cm$^2$. The amount of buprenorphine base for Examples 1 and 2 being 12 mg, the amount of buprenorphine base for Comparative Example 5 being 6.75 mg and the amount of buprenorphine base for BuTrans® being 20 mg.

DETAILED DESCRIPTION

TTS Structure

Figure 1:
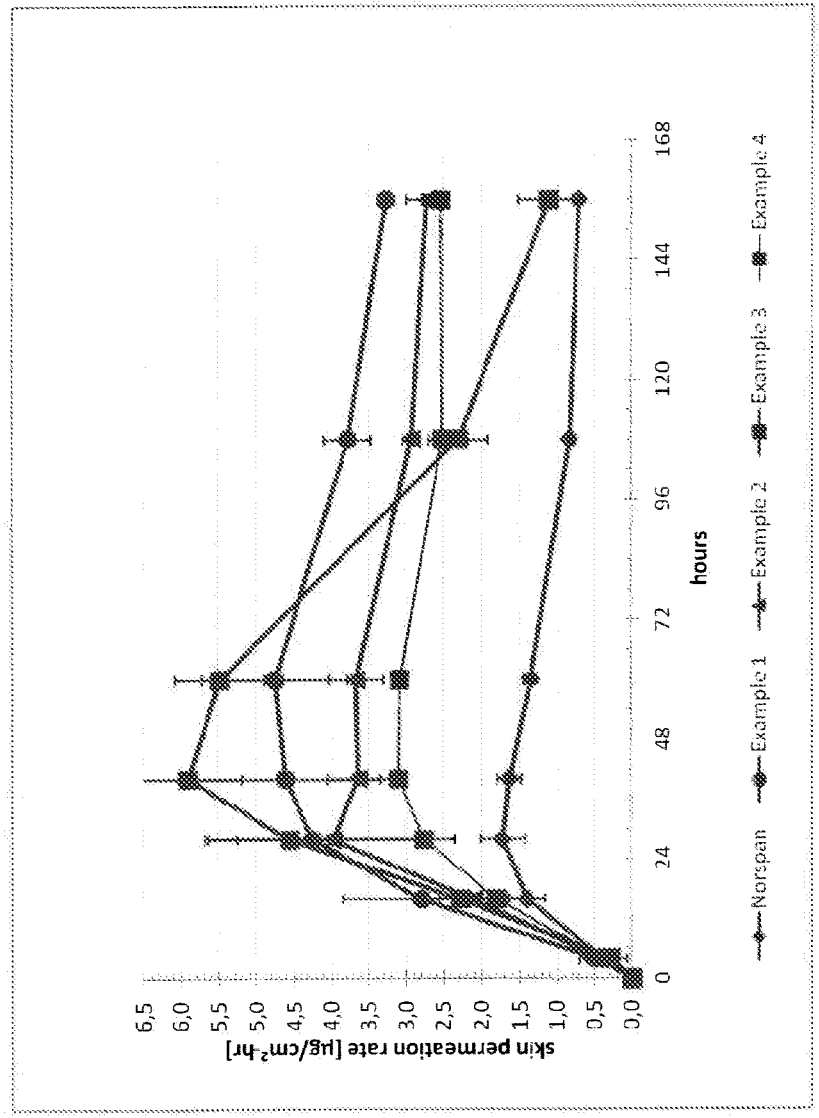
FIG. 1 depicts the mean non-cumulative skin permeation rate for Examples 1 to 4 and Norspan®.

According to the invention wherein the structure is concerned, the TTS for the transdermal administration of buprenorphine comprises a buprenorphine-containing self-adhesive layer structure comprising A) a buprenorphine-impermeable backing layer, and
B) a buprenorphine-containing pressure-sensitive adhesive layer on said buprenorphine-impermeable backing layer, the adhesive layer comprising
 a) at least one polymer-based pressure-sensitive adhesive,
 b) an analgesically effective amount of buprenorphine base or a pharmaceutically acceptable salt thereof, and c) a carboxylic acid selected from the group consisting of oleic acid, linoleic acid, linolenic acid, levulinic acid and mixtures thereof, in an amount sufficient so that said analgesically effective amount of buprenorphine is solubilized therein to form a mixture, and the carboxylic acid buprenorphine mixture forms dispersed deposits in the said pressure-sensitive adhesive, wherein said buprenorphine-containing pressure-sensitive adhesive layer is the skin contact layer.

According to an aspect of the invention the TTS for the transdermal administration of buprenorphine base comprises a buprenorphine base-containing self-adhesive layer structure comprising A) a buprenorphine base-impermeable backing layer, and
B) a buprenorphine base-containing pressure-sensitive adhesive layer on said buprenorphine base-impermeable backing layer, the adhesive layer comprising
   a) at least one pressure-sensitive adhesive based on polysiloxane,
   b) an analgesically effective amount of buprenorphine base or a pharmaceutically acceptable salt thereof, and
   c) levulinic acid in an amount sufficient so that said analgesically effective amount of buprenorphine base is solubilized therein to form a mixture, and the levulinic acid buprenorphine base mixture forms dispersed deposits in the said pressure-sensitive adhesive, wherein said buprenorphine base-containing pressure-sensitive adhesive layer is the skin contact layer. Hence, the TTS according to the invention allows no additional layer in between the buprenorphine base-containing pressure-sensitive adhesive layer and the skin.

According to certain preferred embodiments, the invention relates to a TTS with a buprenorphine-containing self-adhesive layer structure consisting essentially of:

A) a buprenorphine base-impermeable backing layer, and
B) a buprenorphine base-containing pressure-sensitive adhesive layer on said buprenorphine base-impermeable backing layer, the adhesive layer comprising
   a) at least one pressure-sensitive adhesive based on polysiloxane,
   b) an analgesically effective amount of buprenorphine base or a pharmaceutically acceptable salt thereof, and
   c) levulinic acid, in an amount sufficient so that said analgesically effective amount of buprenorphine base is solubilized therein to form a mixture, and the levulinic acid buprenorphine base mixture forms dispersed deposits in the said pressure-sensitive adhesive.

According to certain embodiments of the invention, the TTS comprises in addition to the buprenorphine-containing self-adhesive layer structure attached thereto a larger active agent-free self-adhesive layer structure, e.g., a peripheral adhesive or overlying adhesive, for enhancing the adhesive properties of the overall transdermal therapeutic system. Said active agent-free self-adhesive layer structure comprises also a backing layer, e.g., beige colored, and in this case an active agent free pressure-sensitive adhesive layer of polymer-based pressure-sensitive adhesive, e.g., based on polyacrylates or polysiloxane. The area of said second active agent agent-free self-adhesive layer structure adds to the overall size of the TTS but does not add to the area of release. The pressure-sensitive adhesive in the active agent containing and the active agent-free self-adhesive layer structures may be the same or different. If the adhesive in the active agent free self-adhesive layer is different from that of the buprenorphine-containing layer, then pressure-sensitive adhesives selected from the group of poly acrylate based or poly isobutylene based pressure-sensitive adhesives can be used, and poly acrylate based pressure-sensitive adhesives are preferred, in particular pressure-sensitive adhesives based on an acrylate-vinylacetate polymer, e.g., such as those available from Henkel under the tradename Duro Tak®, e.g., Duro Tak® 387 2051. Such pressure-sensitive adhesives are provided in an organic solution of ethyl acetate and heptane. Such pressure-sensitive adhesives provide a 180° Peel at 20 minutes of at least about 20 N/25 mm, and at 24 minutes of at least about 25 N/25 cm, and at one week of at least about 30 N/25 mm and a Loop tack of at least 15 N/25 mm$^2$, or of at least 20 N/25 mm$^2$, or of at least 22 N/25 mm$^2$.

Active Agent

The TTS according to the invention comprises an analgesically effective amount of buprenorphine base or an equimolar amount of a pharmaceutically acceptable salt thereof. Pharmaceutically acceptable salts may be selected from those known in the art, such as the hydrochloride, sulphate, phosphate, tartrate, maleinate, oxalate, acetate and lactate salts. According to a preferred embodiment of the invention the active agent is buprenorphine base.

An analgesically effective amount may vary from about 1 mg to about 50 mg, in particular from about 2 mg to about 30 mg of buprenorphine base or an equimolar amount of a pharmaceutically acceptable salt, or from about 2 mg to about 25 mg of buprenorphine base or an equimolar amount of a pharmaceutically acceptable salt thereof. According to certain embodiments, the TTS contains according to five different dosages from about 1 mg to about 4 mg, or from about 3.5 mg to about 8 mg, or from about 6.5 mg to about 16 mg, or from about 11.5 mg to about 24 mg, or from about 15 mg to about 32 mg of buprenorphine base or a an equimolar amount of a pharmaceutically acceptable salt thereof, or the TTS contains according to five different dosages from about 1 mg to about 4.5 mg, or about 3 mg, or from about 4 mg to about 9 mg, or about 6 mg, or from about 8 mg to about 14 mg, or about 12 mg, or from about 15 mg to about 20 mg, or about 18 mg or from about 20 mg to about 28 mg, or about 24 mg of buprenorphine base or a an equimolar amount of a pharmaceutically acceptable salt thereof Pressure-Sensitive Adhesive The Pressure-sensitive adhesives used for the present invention are polymer-based pressure-sensitive adhesives. Such polymer-based pressure-sensitive adhesives may e.g., be based on polysiloxanes or polyisobutylenes. For the present invention polysiloxane based pressure-sensitive adhesives are preferred. Such polysiloxanes adhesives need, unlike other organic pressures-sensitive adhesives, no additives like antioxidants, stabilizers, plasticizers, catalysts or other potentially extractable ingredients. These pressure-sensitive adhesives provide for suitable tack for quick bonding to various skin types, including wet skin, suitable adhesive and cohesive qualities, long lasting adhesion to the skin of up to 7 days, a high degree of flexibility, a permeability to moisture, and compatibility to many actives and film-substrates. It is possible to provide them with sufficient amine resistance and therefore enhanced stability in the presence of amines. Such pressure-sensitive adhesives are based on a resin-in-polymer concept wherein, by condensation reaction of silanol end blocked polydimethylsiloxane with a silica resin, a polysiloxane is prepared which for amine stability the residual silanol functionality is additionally capped with trimethylsiloxy groups. The dimethiconol content contributes to the viscous component of the viscoelastic behavior, and impacts the wetting and the spreadability properties of the adhesive. The resin acts as a tackifying and reinforcing agent, and participates in the elastic component. The correct balance between dimethiconol and resin provides for the correct adhesive properties.

The adhesive strength of the polysiloxanes may be sufficient for the desired skin contact. In certain embodiments of the invention a plasticizer or a tackifying agent is incorporated into the formulation to improve the adhesive characteristics of the pressure-sensitive adhesive layer. It may be advantageous in an individual case to improve the tack by adding small amounts of tackifiers such as polyterpenes, rosin derivatives, or silicone oils. In preferred embodiments, the tackifying agent is a silicone oil (e.g., 360 Medical Fluid, available from Dow Corning Corporation, Midland, Mich.).

The pressure-sensitive adhesives are supplied and used in solvents like heptane, ethyl acetate or other volatile silicone fluids. For the present invention heptane is preferred. The solids content is usually between 60 and 80%.

The preferred pressure-sensitive adhesives based on polysiloxanes in accordance with the invention are characterized by a solution viscosity at 25° C. and 60% solids content in heptane of more than about 150 mPa s, or from about 200 mPa s to about 700 mPa s, in particular from about 350 mPa s to about 600 mPa s, more preferred from about 480 mPa s to about 550 mPa s, or most preferred of about 500 mPa s or alternatively from about 400 mPa s to about 480 mPa s, or most preferred of about 450 mPa s. Theses may also be characterized by a complex viscosity at 0.01 rad/s at 30° C. of less than about $1 \times 10^9$ Poise or from about $1 \times 10^5$ to about $9 \times 10^8$ Poise, or more preferred from about $1 \times 10^5$ to about $1 \times 10^7$ Poise, or most preferred about $5 \times 10^6$ Poise or alternatively more preferred from about $2 \times 10^7$ to about $9 \times 10^8$ Poise, or most preferred about $1 \times 10^8$ Poise.

Suitable pressure-sensitive adhesives based on polysiloxanes may be obtained from Dow Corning® BIO-PSA Standard Silicone Adhesives. Preferred are the BIO-PSA 7 4301 and BIO-PSA 7 4201 Silicone Adhesives. According to certain embodiments BIO-PSA 7 4301 is preferred and according to certain other embodiments BIO-PSA 7 4201 is preferred. BIO-PSA 4201 has a solution viscosity at 25° C. and about 60% solids content in heptane of 450 mPa s and a complex viscosity at 0.01 rad/s at 30° C. of $1 \times 10^8$ Poise. BIO-PSA 4301 has a solution viscosity at 25° C. and about 60% solids content in heptane of 500 mPa s and a complex viscosity at 0.01 rad/s at 30° C. of $5 \times 10^6$ Poise.

The pressure-sensitive adhesive layer of the TTS of the invention may further comprise in addition to the above mentioned ingredients a), b) and c), namely a polymer-based pressure-sensitive adhesive, the buprenorphine and the carboxylic acid selected from the group of oleic acid, linoleic acid, linolenic acid and levulinic acid as described herein, other various excipients or additives, for example from the group of solubilizers, fillers, tackifiers, substances which influence the barrier properties of the stratum corneum in the sense of increasing the active agent permeability, pH regulators, and preservatives.

Substances which influence the barrier properties of the stratum corneum in the sense of increasing the active agent permeability are known to the skilled worker and the substance appropriate for the respective active agents must-if necessary-be found by means of permeation studies. Some examples are polyhydric alcohols such as dipropylene glycol, propylene glycol, and polyethylene glycol; oils such as olive oil, squalene, and lanolin; fatty ethers such as cetyl ether and oleyl ether; fatty acid esters such as isopropyl myristate; urea and urea derivatives such as allantoin; polar solvents such as dimethyldecylphosphoxide, methyloctylsulfoxide, dimethyllaurylamine, dodecylpyrrolidone, isosorbitol, dimethylacetonide, dimethylsulfoxide, decylmethylsulfoxide, and dimethylformamide; salicylic acid; amino acids; benzyl nicotinate; and higher molecular weight aliphatic surfactants such as lauryl sulfate salts. Other agents include oleic and linoleic acids, ascorbic acid, panthenol, butylated hydroxytoluene, tocopherol, tocopheryl acetate, tocopheryl linoleate, propyl oleate, and isopropyl palmitate. The TTS of the invention may additionally comprise according to certain embodiments in which the pressure-sensitive adhesive layer comprises a) the polymer-based pressure-sensitive adhesive, b) the buprenorphine and c) levulinic acid or linolenic acid or mixtures of both as the carboxylic acid as described herein, oleic and linoleic acids as substances influencing the barrier properties of the stratum corneum in the sense of increasing the active agent permeability.

Such substances as described in the previous paragraph may be included in a TTS and may be present in an amount of about 1% to about 10% by weight. In a preferred embodiment of the present invention such additional substances are however not necessary. According to an embodiment of the invention the TTS does not comprise such additional substances as mentioned in the previous paragraph.

In addition to the carboxylic acid selected from oleic acid, linoleic acid, linolenic acid, levulinic acid, the solubility of the drug can be further altered by the optional addition of an agent that increases the solubility of drug or inhibits drug crystallization in the transdermal composition, such as polyvinylpyrrolidone, vinyl acetate/vinylpyrrolidone copolymer and cellulose derivatives.

Viscosity-increasing substances are preferably used in conjunction with an active agent solution. Suitable substances for increasing the viscosity of the active agent solution are, for example, cellulose derivatives such as ethylcellulose, hydroxylpropylcellulose and high molecular mass polyacrylic acids and/or their salts and/or their derivatives such as esters.

Fillers such as silica gels, titanium dioxide and zinc oxide may be used in conjunction with the polymer in order to influence certain physical parameters, such as cohesion and bond strength, in the desired way.

Buprenorphine-Containing Self-Adhesive Layer Structure

In accordance with the invention, the buprenorphine-containing self-adhesive layer structure comprises a buprenorphine-impermeable backing layer, and a buprenorphine-containing pressure-sensitive adhesive layer coated thereon. In a preferred embodiment, the buprenorphine-containing self-adhesive layer structure consists of these two elements.

The buprenorphine-containing pressure-sensitive adhesive layer may be coated at any dry weight, but is preferably coated at a dry weight of more than about 6 mg/cm$^2$ (about 60 g/m$^2$), or of more than about 8 mg/cm$^2$ (about 80 g/m$^2$), or ranging from about 6 mg/cm$^2$ (about 60 g/m$^2$) to about 14 mg/cm² (about 140 g/m²), or from about 8 mg/cm² (about 80 g/m²) to about 14 mg/cm² (about 140 g/m²). Specifically, the dry weight is more than about 10 mg/cm² (about 100 g/m²), or ranges from about 10 mg/cm² (about 100 g/m²) to about 13 mg/cm² (about 130 g/m²), or ranges from about 11.5 mg/cm² (about 115 g/m²) to about 12.5 mg/cm² (about 125 g/m²), or is specifically about 12 mg/cm² (about 120 g/m²).

The dry buprenorphine-containing pressure-sensitive adhesive layer preferably contains buprenorphine base, but may contain equimolar amounts of pharmaceutically acceptable salts. According to the invention preferably more than 5%, or more than about 6%, or more than about 7%, or more than about 8%, or more than about 9%, or from about 6% to about 20%, or from about 7% to about 20%, or from about 8% to about 20%, or from about 9% to about 20%, or from about 6% to about 15%, or from about 7% to about 15%, or from about 8 to about 15% or from about 9 to about 15% buprenorphine base or equimolar amounts of pharmaceutically acceptable salts based on the total dry weight of the dry buprenorphine-containing pressure-sensitive adhesive layer are contained in the dry buprenorphine-containing pressure-sensitive adhesive layer. In a specific embodiment, about 10% buprenorphine base is contained in the dry buprenorphine-containing pressure-sensitive adhesive layer.

Preferably, the TTS contains in the pressure-sensitive adhesive layer more than about 0.55 mg/cm², or more than about 0.6 mg/cm², or more than about 0.7 mg/cm², or more than about 0.8 mg/cm², or more than about 0.9 mg/cm², or more than about 1 mg/cm², or more than about 1.1 mg/cm², buprenorphine base, or from about 0.55 mg/cm² to about 2 mg/cm², or from about 0.6 mg/cm² to about 2 mg/cm², or from about 0.7 mg/cm² to about 2 mg/cm², or from about 0.8 mg/cm² to about 2 mg/cm², or from about 0.9 mg/cm² to about 2 mg/cm², or from about 1 mg/cm² to about 2 mg/cm², or from about 1.1 mg/cm² to about 2 mg/cm² buprenorphine base or contains about 1.2 mg/cm² buprenorphine base. The TTS may also contain equimolar amounts of pharmaceutically acceptable salts.

In order to provide the desired delivery rate of buprenorphine, a carboxylic acid is present. The carboxylic acid may be selected from the group consisting of oleic acid, linoleic acid, linolenic acid, levulinic acid and mixtures thereof, wherein levulinic acid is preferred. The buprenorphine is in mixture with, e.g., dissolved in, the carboxylic acid, e.g., the levulinic acid, and this mixture, e.g., solution, is dispersed in the form of small deposits, e.g., droplets, in the matrix layer. Buprenorphine, with its known physicochemical properties, namely its poor solubility, its comparatively high melting point of 216° C., and its high molecular weight, tends readily towards crystallization. For this reason, a solubilizer with at least one acidic group is used in order to prevent the buprenorphine from crystallizing during the storage of the pharmaceutical form. Buprenorphine and levulinic acid have an extremely low solubility in polysiloxanes. As a consequence of this, it is possible to solubilize buprenorphine in levulinic acid and to disperse this mixture in the form of small deposits in a matrix layer prepared on the basis of polysiloxanes as described herein.

Levulinic acid is sparingly soluble in the organic solvents of the adhesives. Consequently, the liquid mixture of buprenorphine and levulinic acid can be dispersed in the solution of the adhesive, with the dispersion being retained following removal of the solvent. In a matrix layer of this kind, the solubility of the buprenorphine is dependent virtually only on the amount of the levulinic acid.

The amount of the dispersed mixture of buprenorphine, e.g., buprenorphine base, and the carboxylic acid, e.g., levulinic acid, can be up to about 40% by weight, it being preferred not to exceed about 25% or about 20% by weight and ranges from about 15% to about 25%, or from about 15% to about 20%, or from about 17% to about 20%. The deposit, e.g., droplet, size (diameter) itself ought preferably not to exceed about 150 μm, or ranges from about 1 to about 150 μm, preferably from about 1 to about 50 μm, or from about 5 to about 50 μm, or from about 1 to about 25 μm or from about 5 to about 25 μm. The preferred size is dependent, furthermore, on the thickness of the matrix layer.

Since the carboxylic acid, e.g., the levulinic acid, can likewise be absorbed through the skin, the amount in the TTS becomes less as the time of application elapses, and leads to a reduction of the solubility of buprenorphine. As a result, the decrease in the thermodynamic activity of buprenorphine due to depletion is compensated by the reduced drug solubility in the buprenorphine/levulinic acid deposits.

According to the invention the dry buprenorphine-containing pressure-sensitive adhesive layer contains more than about 5%, or more than about 6%, or more than about 7%, or more than about 8%, or more than about 9%, or from about 6% to about 20%, or from about 7% to about 20%, or from about 8 to about 20%, or from about 9 to about 20%, or from about 5% to about 15%, or from about 6% to about 15%, or from about 6% to about 9%, or from about 9% to about 15% carboxylic acid, e.g., levulinic acid based on the total dry weight of the dry buprenorphine-containing pressure-sensitive adhesive layer. In a specific embodiment the dry buprenorphine-containing pressure-sensitive adhesive layer contains from about 6% to about 11% levulinic acid, or from about 6% to about 9% or from about 9% to about 15% levulinic acid, or about 7% levulinic acid or about 10% levulinic acid. According to a specific embodiment the pressure-sensitive adhesive layer contains the same %-amount of levulinic acid and buprenorphine base or equimolar amounts of pharmaceutically acceptable salts. According to another specific embodiment, the pressure-sensitive adhesive layer contains less %-amount of levulinic acid than it contains %-amount of buprenorphine base or equimolar amounts of pharmaceutically acceptable salts.

According to a specific embodiment, the pressure-sensitive adhesive layer contains from more than 9% to about 15% buprenorphine base and from about 6% to about 9% levulinic acid or from more than 9% to about 15% buprenorphine base and from about 9% to about 15% levulinic acid based on the total dry weight.

According to a certain embodiment the pressure-sensitive adhesive layer is coated at a dry weight of from about 10 mg/cm² to about 14 mg/cm², or from about 11.5 mg/cm² to about 12.5 mg/cm² or is about 12 mg/cm², and the dry pressure-sensitive adhesive layer contains from about 7% to about 13% or from about 8% to about 12%, or from about 9% to about 11% or about 10% buprenorphine base and from about 6% to about 8%, or about 7% levulinic acid. In a specific embodiment the dry pressure-sensitive adhesive layer has a dry weight of about 12 mg/cm² and contains about 7% levulinic acid and about 10% buprenorphine base.

According to a certain other embodiment, the pressure-sensitive adhesive layer is coated at a dry weight of from about 10 mg/cm² to about 14 mg/cm², or from about 11.5 mg/cm² to about 12.5 mg/cm², or is about 12 mg/cm², and the dry pressure-sensitive adhesive layer contains from about 7% to about 13% or from about 8% to about 12%, or from about 9% to about 11% or about 10% buprenorphine base and from about 8 to about 12% or about 10% levulinic acid. In a specific embodiment, the dry pressure-sensitive adhesive layer has a dry weight of about 12 mg/cm$^2$, and contains about 10% levulinic acid and about 10% buprenorphine base.

In accordance with the above, the TTS contains more than about 0.55 mg/cm$^2$, or more than about 0.6 mg/cm$^2$, or more than about 0.7 mg/cm$^2$, or more than about 0.8 mg/cm$^2$, or more than about 0.9 mg/cm$^2$, or more than about 1 mg/cm$^2$, or more than about 1.1 mg/cm$^2$ buprenorphine base or from about 0.6 mg/cm$^2$ to about 2 mg/cm$^2$, or from about 0.7 mg/cm$^2$ to about 2 mg/cm$^2$, or from about 0.8 mg/cm$^2$ to about 2 mg/cm$^2$, or from about 0.9 mg/cm$^2$ to about 2 mg/cm$^2$, or from about 1 mg/cm$^2$ to about 2 mg/cm$^2$, or from about 1.1 mg/cm$^2$ to about 2 mg/cm$^2$ buprenorphine base or contains about 1.2 mg/cm$^2$ buprenorphine base or an equimolar amount of a pharmaceutically acceptable salt thereof, buprenorphine base is preferred. According to a specific embodiment, the pressure-sensitive adhesive layer contains the same amounts of levulinic acid and buprenorphine base. According to another specific embodiment, the pressure-sensitive adhesive layer contains less levulinic acid than it contains buprenorphine base or an equimolar amount of a pharmaceutically acceptable salt thereof.

According to a certain embodiment of the invention, the pressure-sensitive adhesive in the buprenorphine-containing layer and in the active agent-free layer are different, and the adhesive in the active agent-free layer is a pressure-sensitive adhesive based on polyacrylates. According to certain other embodiments the adhesive in the active agent-containing and the active agent-free layer are the same and are an amine-resistant pressure-sensitive adhesive based on polysiloxane wherein the polysiloxane is a product of the condensation reaction of silanol endblocked polydimethylsiloxane with a silica resin and the residual silanol functionality is capped with trimethylsiloxy groups and characterized by a solution viscosity at 25° C. and about 60% solids content in heptanes of about 500 mPa s or of about 450 mPa s, and the buprenorphine-containing layer pressure-sensitive adhesive layer is coated at a dry weight of about 12 mg/cm$^2$ and contains about 10% Buprenorphine base and about 10% levulinic acid.

According to certain embodiments, the area of release ranges from about 1 cm$^2$ to about 38 cm$^2$, or the area of release is less than 25 cm$^2$, or less than 22 cm$^2$, or ranges from about 1.5 to about 25 cm$^2$, or from about 1.5 to about 22 cm$^2$, or from about 1.5 to about 20 cm$^2$, or is about 3 cm$^2$ or about 6 cm$^2$, or about 10 cm$^2$, or about 15 cm$^2$ or about 20 cm$^2$.

According to certain embodiments, the TTS contains from about 1 mg to about 32 mg of buprenorphine base or an equimolar amount of a pharmaceutically acceptable salt thereof, or from about 1 mg to about 28 mg, or 2 mg to about 25 mg, or from about 2 mg to about 24 mg of buprenorphine base or an equimolar amount of a pharmaceutically acceptable salt thereof. Considering five different increasing dosage strengths, the TTS in specific cases preferably contains a) from about 1 mg to about 4 mg, or from about 1 mg to about 4.5 mg, preferably from about 1 mg to about 3.5 mg, or from about 2 mg to about 4 mg, more preferably from about 1 mg to about 3 mg, or from about 2.5 mg to about 4 mg, or about 3 mg buprenorphine base or an equimolar amount of a pharmaceutically acceptable salt thereof, or b) from about 3.5 mg to about 8 mg, or from about 4 mg to about 9 mg, preferably from about 3.5 mg to about 7 mg, or from about 5 mg to about 8 mg, more preferably from about 3.5 mg to about 6 mg, or from about 5 mg to about 7 mg, or about 6 mg buprenorphine base or an equimolar amount of a pharmaceutically acceptable salt thereof, or c) from about 6.5 mg to about 16 mg, or from about 8 mg to about 14 mg, preferably from about 6.5 mg to about 14 mg, or from about 10 mg to about 14 mg, more preferably from about 6.5 mg to about 11 mg, or from about 11 mg to about 13 mg, or about 12 mg buprenorphine base or an equimolar amount of a pharmaceutically acceptable salt thereof, or d) from about 11.5 mg to about 24 mg, or from about 15 mg to about 20 mg, preferably from about 11.5 mg to about 21 mg, or from about 16 mg to about 19 mg, more preferably from about 11.5 mg to about 14 mg, or from about 17 mg to about 19 mg, or about 18 mg buprenorphine base or an equimolar amount of a pharmaceutically acceptable salt thereof, or e) from about 15 mg to about 32 mg, or from about 20 mg to about 28 mg, preferably from about 15 mg to about 28 mg, or from about 21 mg to about 26 mg, more preferably from about 15 mg to about 24 mg, or from about 22 mg to about 25 mg, or about 24 mg of buprenorphine base or an equimolar amount of a pharmaceutically acceptable salt thereof.

Correspondingly the area of release ranges from about 1 cm$^2$ to about 38 cm$^2$, or from 1.5 cm$^2$ to about 24 cm$^2$, or ranges from 1.5 cm$^2$ to about 22 cm$^2$, or ranges from 1.5 cm$^2$ to about 20 cm$^2$ and with respect to the five specific preferred dosage strengths a) to e)

a) ranges from about 1 cm$^2$ to about 4.8 cm$^2$, or from about 1.5 cm$^2$ to about 5.5 cm$^2$, preferably from about 1 cm$^2$ to about 4.5 cm$^2$, or from about 2 cm$^2$ to about 4 cm$^2$, more preferably from about 2.5 cm$^2$ to about 4 cm$^2$, or from about 2 cm$^2$ to about 3 cm$^2$, or is about 2.5 cm$^2$, or b) ranges from about 3 cm$^2$ to about 9.5 cm$^2$, or from about 3 cm$^2$ to about 9 cm$^2$, preferably from about 3 cm$^2$ to about 9 cm$^2$, or from about 4.5 cm$^2$ to about 7.5 cm$^2$, more preferably from about 5 cm$^2$ to about 8 cm$^2$, or from about 4.5 cm$^2$ to about 6 cm$^2$, or is about 5 cm$^2$, or c) ranges from about 6 cm$^2$ to about 19 cm$^2$, or from about 6 cm$^2$ to about 14 cm$^2$, preferably from about 6 cm$^2$ to about 18 cm$^2$, or from about 8 cm$^2$ to about 12 cm$^2$, more preferably from about 10 cm$^2$ to about 16 cm$^2$, or from about 9 cm$^2$ to about 11 cm$^2$, or is about 10 cm$^2$, or d) ranges from about 12 cm$^2$ to about 28.5 cm$^2$, or from about 13 cm$^2$ to about 17 cm$^2$, preferably from about 12 cm$^2$ to about 27 cm$^2$, or from about 13 cm$^2$ to about 16 cm$^2$, more preferably from about 17 cm$^2$ to about 23 cm$^2$, or from about 14 cm$^2$ to about 16 cm$^2$, or is about 15 cm$^2$, or e) ranges from about 16 cm$^2$ to about 38 cm$^2$, or from about 16 cm$^2$ to about 24 cm$^2$, preferably or from about 16 cm$^2$ to about 35 cm$^2$, or from about 17 cm$^2$ to about 22 cm$^2$, more preferably from about 23.5 cm$^2$ to about 32 cm$^2$, or from about 18 cm$^2$ to about 21 cm$^2$, or is about 20 cm$^2$.

In such embodiments the dry pressure-sensitive adhesive layer preferably comprises a pressure-sensitive adhesive based on polysiloxanes and has preferably a dry weight of about 6 mg/cm$^2$, 7.5 mg/cm$^2$, 8 mg/cm$^2$, 9 mg/cm$^2$, 10.5 mg/cm$^2$, or 12 mg/cm$^2$ and contains 10% buprenorphine base.

According to certain preferred embodiments, the TTS contains with respect to five dosage strengths a) to e) the following amounts of buprenorphine base or an equimolar amount of a pharmaceutically acceptable salt thereof and provides the following corresponding area of release ranges:

| a) | about 1 cm² to about 4.8 cm² | about 1 cm² to about 4.5 cm² | about 2.5 cm² to about 4 cm² |
|---|---|---|---|
| about 1 mg to about 4 mg | X | X | X |
| about 1 mg to about 3.5 mg | X | X | X |
| about 1 mg to about 3 mg | X | X | X |

| b) | about 3 cm² to about 9.5 cm² | about 3 cm² to about 9 cm² | about 5 cm² to about 8 cm² |
|---|---|---|---|
| about 3.5 mg to about 8 mg | X | X | X |
| about 3.5 mg to about 7 mg | X | X | X |
| about 3.5 mg to about 6 mg | X | X | X |

| c) | about 6 cm² to about 19 cm² | about 6 cm² to about 18 cm² | about 10 cm² to about 16 cm² |
|---|---|---|---|
| about 6.5 mg to about 16 mg | X | X | X |
| about 6.5 mg to about 14 mg | X | X | X |
| about 6.5 mg to about 11 mg | X | X | X |

| d) | about 12 cm² to about 28.5 cm² | about 12 cm² to about 27 cm² | about 17 cm² to about 23 cm² |
|---|---|---|---|
| about 11.5 mg to about 24 mg | X | X | X |
| about 11.5 mg to about 21 mg | X | X | X |
| about 11.5 mg to about 14 mg | X | X | X |

| e) | about 16 cm² to about 38 cm² | about 16 cm² to about 35 cm² | about 23.5 cm² to about 32 cm² |
|---|---|---|---|
| about 15 mg to about 32 mg | X | X | X |
| about 15 mg to about 28 mg | X | X | X |
| about 15 mg to about 24 mg | X | X | X |

Set of Transdermal Therapeutic Systems

For the treatment of pain a patient needs to be titrated to the individual dose of buprenorphine to adequately control the pain. In order to meet the individual requirements five different dosage strengths are provided in accordance with the invention.

According to one aspect, the invention relates to a set of two (first and second, or second and third, or third and fourth, or fourth and fifth TTS, or any other combination of two of the five different dosage strengths), three (first to third, or second to fourth or third to fifth TTS, or any other combination of three of the five different dosage strengths), four (first to fourth or second to fifth TTS, or any other combination of four of the five different dosage strengths) or five (first to fifth TTS) different transdermal therapeutic systems in accordance with the invention, wherein:

the first transdermal therapeutic system provides a size of said buprenorphine-containing pressure-sensitive adhesive layer providing the area of release ranging from about 1 cm² to about 4.8 cm², or from about 1.5 cm² to about 5.5 cm² and contains an amount of said buprenorphine from about 1 mg to about 4 mg, or from about 1 mg to about 4.5 mg buprenorphine base or an equimolar amount of a pharmaceutically acceptable salt thereof; and the second transdermal therapeutic system provides a size of said buprenorphine-containing pressure-sensitive adhesive layer providing the area of release ranging from about 3 cm² to about 9.5 cm², or from about 3 cm² to about 9 cm² and contains an amount of said buprenorphine from about 3.5 mg to about 8 mg, or from about 4 mg to about 9 mg buprenorphine base or an equimolar amount of a pharmaceutically acceptable salt thereof; and the third transdermal therapeutic system provides a size of said buprenorphine-containing pressure-sensitive adhesive layer providing the area of release ranging from about 6 cm² to about 19 cm², or from about 6 cm² to about 14 cm² and contains an amount of said buprenorphine from about 6.5 mg to about 16 mg, or from about 8 mg to about 14 mg buprenorphine base or an equimolar amount of a pharmaceutically acceptable salt thereof; and the fourth transdermal therapeutic system provides a size of said buprenorphine-containing pressure-sensitive adhesive layer providing the area of release ranging from about 12 cm² to about 28.5 cm², or from about 13 cm² to about 17 cm² and contains an amount of said buprenorphine from about 11.5 mg to about 24 mg, or from about 15 mg to about 20 mg buprenorphine base or an equimolar amount of a pharmaceutically acceptable salt thereof; and the fifth transdermal therapeutic system provides a size of said buprenorphine-containing pressure-sensitive adhesive layer providing the area of release ranging from about 16 cm² to about 38 cm², or from about 16 cm² to about 24 cm² and contains an amount of said buprenorphine from about 15 mg to about 32 mg, or from about 20 mg to about 28 mg buprenorphine base or an equimolar amount of a pharmaceutically acceptable salt thereof The invention relates also to set of transdermal therapeutic systems, wherein:

the first transdermal therapeutic system provides a size of said buprenorphine-containing pressure-sensitive adhesive layer providing the area of release ranging from about 1 cm² to about 4.5 cm², or from about 2 cm² to about 4 cm² and contains an amount of said buprenorphine from about 1 mg to about 3.5 mg, or from about 2 mg to about 4 mg buprenorphine base or an equimolar amount of a pharmaceutically acceptable salt thereof; and the second transdermal therapeutic system provides a size of said buprenorphine-containing pressure-sensitive adhesive layer providing the area of release ranging from about 3 cm² to about 9 cm², or from about 4.5 cm² to about 7.5 cm² and contains an amount of said buprenorphine from about 3.5 mg to about 7 mg, or from about 5 mg to about 8 mg buprenorphine base or an equimolar amount of a pharmaceutically acceptable salt thereof; and the third transdermal therapeutic system provides a size of said buprenorphine-containing pressure-sensitive adhesive layer providing the area of release ranging from about 6 cm² to about 18 cm², or from about 8 cm² to about 12 cm² and contains an amount of said buprenorphine from about 6.5 mg to about 14 mg, or from about 10 mg to about 14 mg buprenorphine base or an equimolar amount of a pharmaceutically acceptable salt thereof; and the fourth transdermal therapeutic system provides a size of said buprenorphine-containing pressure-sensitive adhesive layer providing the area of release ranging from about 12 cm$^2$ to about 27 cm$^2$, or from about 13 cm$^2$ to about 16 cm$^2$ and contains an amount of said buprenorphine from about 11.5 mg to about 21 mg, or from about 16 mg to about 19 mg buprenorphine base or an equimolar amount of a pharmaceutically acceptable salt thereof; and the fifth transdermal therapeutic system provides a size of said buprenorphine-containing pressure-sensitive adhesive layer providing the area of release ranging from about 16 cm$^2$ to about 35 cm$^2$, or from about 17 cm$^2$ to about 22 cm$^2$ and contains an amount of said buprenorphine from about 15 mg to about 28 mg, or from about 21 mg to about 26 mg buprenorphine base or an equimolar amount of a pharmaceutically acceptable salt thereof The invention relates also to set of different transdermal therapeutic, wherein:

the first transdermal therapeutic system provides a size of said buprenorphine-containing pressure-sensitive adhesive layer providing the area of release ranging from about 2.5 cm$^2$ to about 4 cm$^2$, or from about 2 cm$^2$ to about 3 cm$^2$ and contains an amount of said buprenorphine from about 1 mg to about 3 mg, or from about 2.5 mg to about 4 mg buprenorphine base or an equimolar amount of a pharmaceutically acceptable salt thereof; and the second transdermal therapeutic system provides a size of said buprenorphine-containing pressure-sensitive adhesive layer providing the area of release ranging from about 5 cm$^2$ to about 8 cm$^2$, or from about 4.5 cm$^2$ to about 6 cm$^2$ and contains an amount of said buprenorphine from about 3.5 mg to about 6 mg, or from about 5 mg to about 7 mg buprenorphine base or an equimolar amount of a pharmaceutically acceptable salt thereof; and the third transdermal therapeutic system provides a size of said buprenorphine-containing pressure-sensitive adhesive layer providing the area of release ranging from about 10 cm$^2$ to about 16 cm$^2$, or from about 9 cm$^2$ to about 11 cm$^2$ and contains an amount of said buprenorphine from about 6.5 mg to about 11 mg, or from about 11 mg to about 13 mg buprenorphine base or an equimolar amount of a pharmaceutically acceptable salt thereof; and the fourth transdermal therapeutic system provides a size of said buprenorphine-containing pressure-sensitive adhesive layer providing the area of release ranging from about 17 cm$^2$ to about 23 cm$^2$, or from about 14 cm$^2$ to about 16 cm$^2$ and contains an amount of said buprenorphine from about 11.5 mg to about 14 mg, or from about 17 mg to about 19 mg buprenorphine base or an equimolar amount of a pharmaceutically acceptable salt thereof; and the fifth transdermal therapeutic system provides a size of said buprenorphine-containing pressure-sensitive adhesive layer providing the area of release ranging from about 23.5 cm$^2$ to about 32 cm$^2$, or from about 18 cm$^2$ to about 21 cm$^2$ and contains an amount of said buprenorphine from about 15 mg to about 24 mg, or from about 22 mg to about 25 mg buprenorphine base or an equimolar amount of a pharmaceutically acceptable salt thereof In a further aspect of the invention a transdermal therapeutic system selected from a set of transdermal therapeutic systems as described in the previous paragraphs is provided wherein buprenorphine is present in the form of buprenorphine base and wherein the first transdermal therapeutic system when tested in a comparative clinical study is bioequivalent to a reference product having an area of release of about 6.25 cm$^2$ and providing a nominal mean release rate of about 5 µg/hr over about 168 hours of administration, the second transdermal therapeutic system when tested in a comparative clinical study is bioequivalent to a reference product having an area of release of about 12.5 cm$^2$ and providing a nominal mean release rate of about 10 µg/hr over about 168 hours of administration, the third transdermal therapeutic system when tested in a comparative clinical study is bioequivalent to a reference product having an area of release of about 25 cm$^2$ and providing a nominal mean release rate of about 20 µg/hr over about 168 hours of administration, the fourth transdermal therapeutic system when tested in a comparative clinical study is bioequivalent to a reference product having an area of release of about 37.5 cm$^2$ and providing a nominal mean release rate of about 30 µg/hr over about 168 hours of administration, the fifth transdermal therapeutic system when tested in a comparative clinical study is bioequivalent to a reference product having an area of release of about 50 cm$^2$ and providing a nominal mean release rate of about 40 µg/hr over about 168 hours of administration, wherein the reference product is prepared by the following steps:

1. homogenizing of 1,139 g of a 47.83% polyacrylate solution of a self-crosslinked acrylate copolymer of 2-ethylhexyl acrylate, vinyl acetate, acrylic acid (solvent: ethyl acetate:heptanes:isopropanol:toluene:acetylacetonate in the ratio of 37:26:26:4:1), 100 g of levulinic acid, 150 g of oleyl oleate, 100 g of polyvinylpyrrolidone, 150 g of ethanol, 200 g of ethyl acetate, and 100 g of buprenorphine base to provide a mixture;
2. stirring the mixture of step 1 for about 2 hours and controlling the dissolution of all solids visually whereas controlling the evaporation loss by reweighing and replenishing the possible solvent loss by ethyl acetate;
3. subsequently applying the mixture on a transparent polyester film in such a manner that the mass per unit area of the dry adhesive layer amounts to about 80 g/m$^2$ wherein the polyester film is rendered removable by means of siliconization and serves as protective layer;
4. removing the solvents of the mixture applied on a transparent polyester film in step 3 by drying with heated air which is led over a moist lane resulting in evaporation of the solvents, but also in melting of the levulinic acid and covering the adhesive film with a polyester foil;
5. punching the area of release of 6.25 cm$^2$, 12.5 cm$^2$, 25 cm$^2$, 37.5 cm$^2$ and 50 cm$^2$, respectively, by means of suitable cutting tools and removing the edges left between the individual systems.

According to one aspect, the invention relates to a transdermal therapeutic system described as first transdermal therapeutic system in the previous paragraphs wherein buprenorphine is present in the form of buprenorphine base and which is when tested in a comparative clinical study bioequivalent to the commercial product BuTrans®, also known as Norspan®, having an area of release of 6.25 cm$^2$.

According to one aspect, the invention relates to a transdermal therapeutic system described as second transdermal therapeutic system in the previous paragraphs wherein buprenorphine is present in the form of buprenorphine base and which is when tested in a comparative clinical study bioequivalent to the commercial product BuTrans®, also known as Norspan®, having an area of release of 12.5 cm².

According to one aspect, the invention relates to a transdermal therapeutic system described as third transdermal therapeutic system in the previous paragraphs wherein buprenorphine is present in the form of buprenorphine base and which is when tested in a comparative clinical study bioequivalent to the commercial product BuTrans®, also known as Norspan®, having an area of release of 25 cm².

According to one aspect, the invention relates to a transdermal therapeutic system comprising buprenorphine for the transdermal administration of buprenorphine selected from:
a first transdermal therapeutic system providing a size of the area of release ranging from about 1 cm² to about 4.8 cm² and containing an amount of said buprenorphine from 1 mg to about 4 mg buprenorphine base or an equimolar amount of a pharmaceutically acceptable salt thereof and providing a nominal mean release rate of about 5 μg/hr and/or providing a mean AUCt of more than 7,000 pg.hr/ml, preferably more than 8,000 pg.hr/ml, or of from more than 7,000 pg.hr/ml to about 16,000 pg.hr/ml, or of from more than 8,000 pg.hr/ml to about 16,000 pg.hr/ml over about 168 hours of administration after a single-dose administration to a subject population;
a second transdermal therapeutic system providing a size of the area of release ranging from about 3 cm² to about 9.5 cm² and containing an amount of said buprenorphine from about 3.5 mg to about 8 mg buprenorphine base or an equimolar amount of a pharmaceutically acceptable salt thereof and providing a nominal mean release rate of about 10 μg/hr and/or providing a mean AUCt of more than 14,000 pg.hr/ml, preferably of more than 16,000 pg.hr/ml, or of from more than 14,000 pg.hr/ml to about 32,000 pg.hr/ml, or of from more than 16,000 pg.hr/ml to about 32,000 pg.hr/ml over about 168 hours of administration after a single-dose administration to a subject population; and
a third transdermal therapeutic system providing a size of the area of release ranging from about 6 cm² to about 19 cm² and containing an amount of said buprenorphine from about 6.5 mg to about 16 mg buprenorphine base or an equimolar amount of a pharmaceutically acceptable salt thereof and providing a nominal mean release rate of about 20 μg/hr and/or providing a mean AUCt of more than 28,000 pg.hr/ml, preferably of more than 32,000 pg.hr/ml, or of from more than 28,000 pg.hr/ml to about 64,000 pg.hr/ml, or of from more than 32,000 pg.hr/ml to about 64,000 pg.hr/ml over about 168 hours of administration after a single-dose administration to a subject population; and
a fourth transdermal therapeutic system providing a size of the area of release ranging from about 12 cm² to about 28.5 cm² and containing an amount of said buprenorphine from about 11.5 mg to about 24 mg buprenorphine base or an equimolar amount of a pharmaceutically acceptable salt thereof and providing a nominal mean release rate of about 30 μg/hr and/or providing a mean AUCt of more than 42,000 pg.hr/ml, preferably of more than 48,000 pg.hr/ml, or of from more than 42,000 pg.hr/ml to about 96,000 pg.hr/ml, or of from more than 48,000 pg.hr/ml to about 96,000 pg.hr/ml over about 168 hours of administration after a single-dose administration to a subject population; and
a fifth transdermal therapeutic system providing a size of the area of release ranging from about 16 cm² to about 38 cm² and containing an amount of said buprenorphine from about 15 mg to about 32 mg buprenorphine base or an equimolar amount of a pharmaceutically acceptable salt thereof and providing a nominal mean release rate of about 40 μg/hr and/or providing a mean AUCt of more than 62,000 pg.hr/ml, preferably of more than 64,000 pg.hr/ml, or of from more than 62,000 pg.hr/ml to about 128,000 pg.hr/ml, or of from more than 64,000 pg.hr/ml to about 128,000 pg.hr/ml over about 168 hours of administration after a single-dose administration to a subject population.

According to one aspect, the invention relates to a transdermal therapeutic system comprising buprenorphine for the transdermal administration of buprenorphine selected from:
a first transdermal therapeutic system providing a size of the area of release ranging from about 1 cm² to about 4.5 cm² and containing an amount of said buprenorphine from 1 mg to about 3.5 mg buprenorphine base or an equimolar amount of a pharmaceutically acceptable salt thereof and providing a nominal mean release rate of about 5 μg/hr and/or providing a mean AUCt of more than 7,000 pg.hr/ml, preferably more than 8,000 pg.hr/ml, or of from more than 7,000 pg.hr/ml to about 16,000 pg.hr/ml, or of from more than 8,000 pg.hr/ml to about 16,000 pg.hr/ml over about 168 hours of administration after a single-dose administration to a subject population;
a second transdermal therapeutic system providing a size of the area of release ranging from about 3 cm² to about 9 cm² and containing an amount of said buprenorphine from about 3.5 mg to about 7 mg buprenorphine base or an equimolar amount of a pharmaceutically acceptable salt thereof and providing a nominal mean release rate of about 10 μg/hr and/or providing a mean AUCt of more than 14,000 pg.hr/ml, preferably of more than 16,000 pg.hr/ml, or of from more than 14,000 pg.hr/ml to about 32,000 pg.hr/ml, or of from more than 16,000 pg.hr/ml to about 32,000 pg.hr/ml over about 168 hours of administration after a single-dose administration to a subject population; and
a third transdermal therapeutic system providing a size of the area of release ranging from about 6 cm² to about 18 cm² and containing an amount of said buprenorphine from about 6.5 mg to about 14 mg buprenorphine base or an equimolar amount of a pharmaceutically acceptable salt thereof and providing a nominal mean release rate of about 20 μg/hr and/or providing a mean AUCt of more than 28,000 pg.hr/ml, preferably of more than 32,000 pg.hr/ml, or of from more than 28,000 pg.hr/ml to about 64,000 pg.hr/ml, or of from more than 32,000 pg.hr/ml to about 64,000 pg.hr/ml over about 168 hours of administration after a single-dose administration to a subject population; and
a fourth transdermal therapeutic system providing a size of the area of release ranging from about 12 cm² to about 27 cm² and containing an amount of said buprenorphine from about 11.5 mg to about 21 mg buprenorphine base or an equimolar amount of a pharmaceutically acceptable salt thereof and providing a nominal mean release rate of about 30 μg/hr and/or providing a mean AUCt of more than 42,000 pg.hr/ml, preferably of more than 48,000 pg.hr/ml, or of from more than 42,000 pg.hr/ml to about 96,000 pg.hr/ml, or of from more than 48,000 pg.hr/ml to about 96,000 pg.hr/ml over about 168 hours of administration after a single-dose administration to a subject population; and
a fifth transdermal therapeutic system providing a size of the area of release ranging from about 16 cm² to about 35 cm² and containing an amount of said buprenorphine from about 15 mg to about 28 mg buprenorphine base or an equimolar amount of a pharmaceutically acceptable salt thereof and providing a nominal mean release rate of about 40 μg/hr and/or providing a mean AUCt of more than 62,000 pg.hr/ml, preferably of more than 64,000 pg.hr/ml, or of from more than 62,000 pg.hr/ml to about 128,000 pg.hr/ml, or of from more than 64,000 pg.hr/ml to about 128,000 pg.hr/ml over about 168 hours of administration after a single-dose administration to a subject population.

According to one aspect, the invention relates a transdermal therapeutic system comprising buprenorphine for the transdermal administration of buprenorphine selected from:
a first transdermal therapeutic system providing a size of the area of release ranging from about 2.5 cm$^2$ to about 4 cm$^2$ and containing an amount of said buprenorphine from 1 mg to about 3 mg buprenorphine base or an equimolar amount of a pharmaceutically acceptable salt thereof and providing a nominal mean release rate of about 5 µg/hr and/or providing a mean AUCt of more than 7,000 pg.hr/ml, preferably more than 8,000 pg.hr/ml, or of from more than 7,000 pg.hr/ml to about 16,000 pg.hr/ml, or of from more than 8,000 pg.hr/ml to about 16,000 pg.hr/ml over about 168 hours of administration after a single-dose administration to a subject population;
a second transdermal therapeutic system providing a size of the area of release ranging from about 5 cm$^2$ to about 8 cm$^2$ and containing an amount of said buprenorphine from about 3.5 mg to about 6 mg buprenorphine base or an equimolar amount of a pharmaceutically acceptable salt thereof and providing a nominal mean release rate of about 10 µg/hr and/or providing a mean AUCt of more than 14,000 pg.hr/ml, preferably of more than 16,000 pg.hr/ml, or of from more than 14,000 pg.hr/ml to about 32,000 pg.hr/ml, or of from more than 16,000 pg.hr/ml to about 32,000 pg.hr/ml over about 168 hours of administration after a single-dose administration to a subject population; and
a third transdermal therapeutic system providing a size of the area of release ranging from about 10 cm$^2$ to about 16 cm$^2$ and containing an amount of said buprenorphine from about 6.5 mg to about 11 mg buprenorphine base or an equimolar amount of a pharmaceutically acceptable salt thereof and providing a nominal mean release rate of about 20 µg/hr and/or providing a mean AUCt of more than 28,000 pg.hr/ml, preferably of more than 32,000 pg.hr/ml, or of from more than 28,000 pg.hr/ml to about 64,000 pg.hr/ml, or of from more than 32,000 pg.hr/ml to about 64,000 pg.hr/ml over about 168 hours of administration after a single-dose administration to a subject population; and
a fourth transdermal therapeutic system providing a size of the area of release ranging from about 17 cm$^2$ to about 23 cm$^2$ and containing an amount of said buprenorphine from about 11.5 mg to about 14 mg buprenorphine base or an equimolar amount of a pharmaceutically acceptable salt thereof and providing a nominal mean release rate of about 30 µg/hr and/or providing a mean AUCt of more than 42,000 pg.hr/ml, preferably of more than 48,000 pg.hr/ml, or of from more than 42,000 pg.hr/ml to about 96,000 pg.hr/ml, or of from more than 48,000 pg.hr/ml to about 96,000 pg.hr/ml over about 168 hours of administration after a single-dose administration to a subject population; and
a fifth transdermal therapeutic system providing a size of the area of release ranging from about 23.5 cm$^2$ to about 32 cm$^2$ and containing an amount of said buprenorphine from about 15 mg to about 24 mg buprenorphine base or an equimolar amount of a pharmaceutically acceptable salt thereof and providing a nominal mean release rate of about 40 µg/hr and/or providing a mean AUCt of more than 62,000 pg.hr/ml, preferably of more than 64,000 pg.hr/ml, or of from more than 62,000 pg.hr/ml to about 128,000 pg.hr/ml, or of from more than 64,000 pg.hr/ml to about 128,000 pg.hr/ml over about 168 hours of administration after a single-dose administration to a subject population.

Release Characteristic

In accordance with the invention, the TTS is further characterized by the skin permeation rate determined by in vitro experiments carried out with the Franz diffusion cell (e.g., a 9 ml Franz diffusion cell), using human split thickness skin. Skin from cosmetic surgeries (female breast, date of birth 1989) can be used. A dermatome is used to prepare skin to a thickness of 800 µm, with an intact epidermis, in accordance with the OECD Guideline (adopted Apr. 13, 2004). Due to the prolonged test (168 hours) 800 µm skin is used instead of the recommended 200 to 400 µm skin. The receptor medium used is a phosphate buffer solution pH 5.5 with 0.1% saline azide as antibacteriological agent is used at a temperature of 32±1°. Example formulations with an area of 1.163 cm$^2$ are punched from laminates, and in the present examples are each tested against 1.163 cm$^2$ samples of the commercial product Norspan®. The concentrations of buprenorphine in the acceptor medium of the Franz cell are measured.

The TTS according to the invention provides a mean cumulative skin permeation rate of more than about 1.3 µg/cm$^2$-hr, or more than about 1.5 µg/cm$^2$-hr or more than about 1.7 µg/cm$^2$-hr over a 168 hours test, or of more than about 2 µg/cm$^2$-hr over a 168 hours test, or of more than about 2.5 µg/cm$^2$-hr over a 168 hours test, or of more than 2.7 µg/cm$^2$-hr over a 168 hours test, or of more than about 3 µg/cm$^2$-hr over a 168 hours test, or from about 1.3 µg/cm$^2$-hr to about 4 µg/cm$^2$-hr, or from about 1.7 µg/cm$^2$-hr to about 4 µg/cm$^2$-hr, or from about 2 µg/cm$^2$-hr to about 4 µg/cm$^2$-hr, or from about 2.5 µg/cm$^2$-hr to about 4 µg/cm$^2$-hr, or from about 2.7 µg/cm$^2$-hr to about 4 µg/cm$^2$-hr, or from about 3 µg/cm$^2$-hr to about 4 µg/cm$^2$-hr, over a 168 hours test. The commercial product Norspan® provides a mean cumulative skin permeation rate of about 1 µg/cm$^2$-hr over a 168 hours test in said test.

Figure 2:
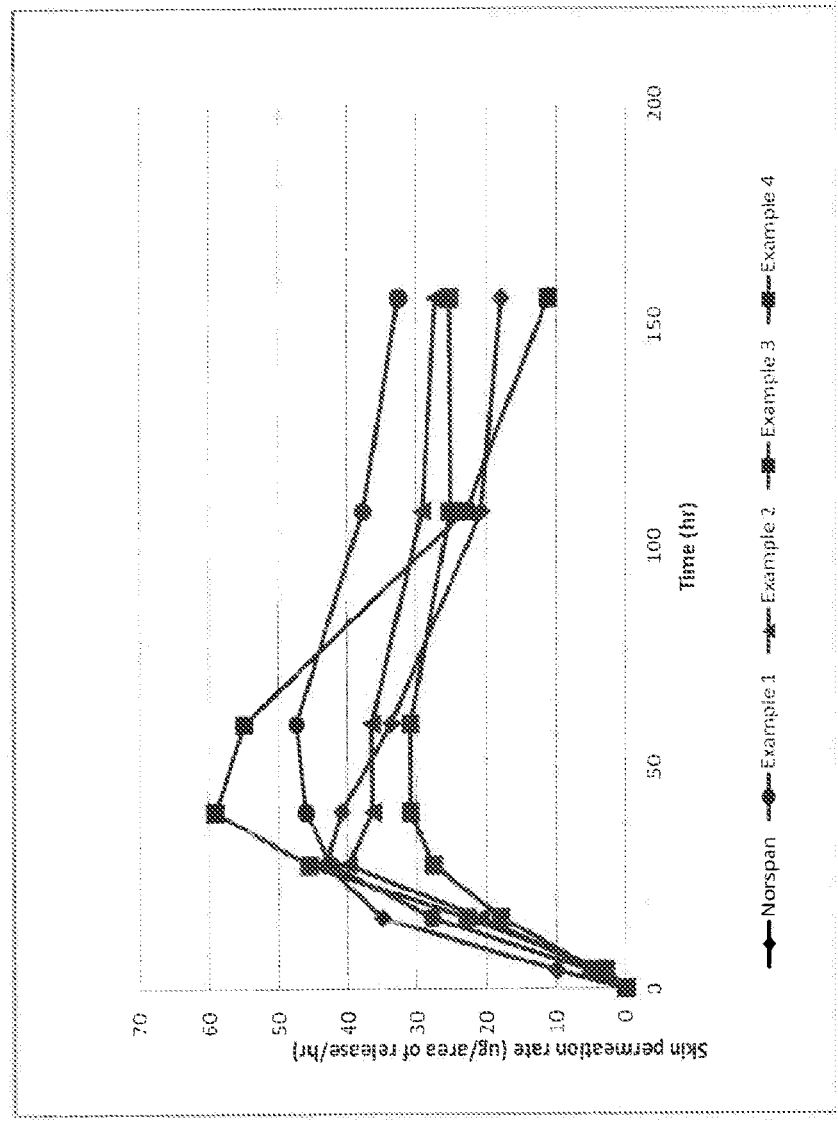
FIG. 2 depicts the mean non-cumulative skin permeation rate of the transdermal therapeutic systems. The area of release of the transdermal therapeutic systems according to Examples 1 to 4 being 10 cm$^2$ and the area of release for Norspan® being 25 cm$^2$. The amount of buprenorphine base for Examples 1 to 4 being 12 mg and the amount of buprenorphine base for Norspan® being 20 mg.
Figure 3:
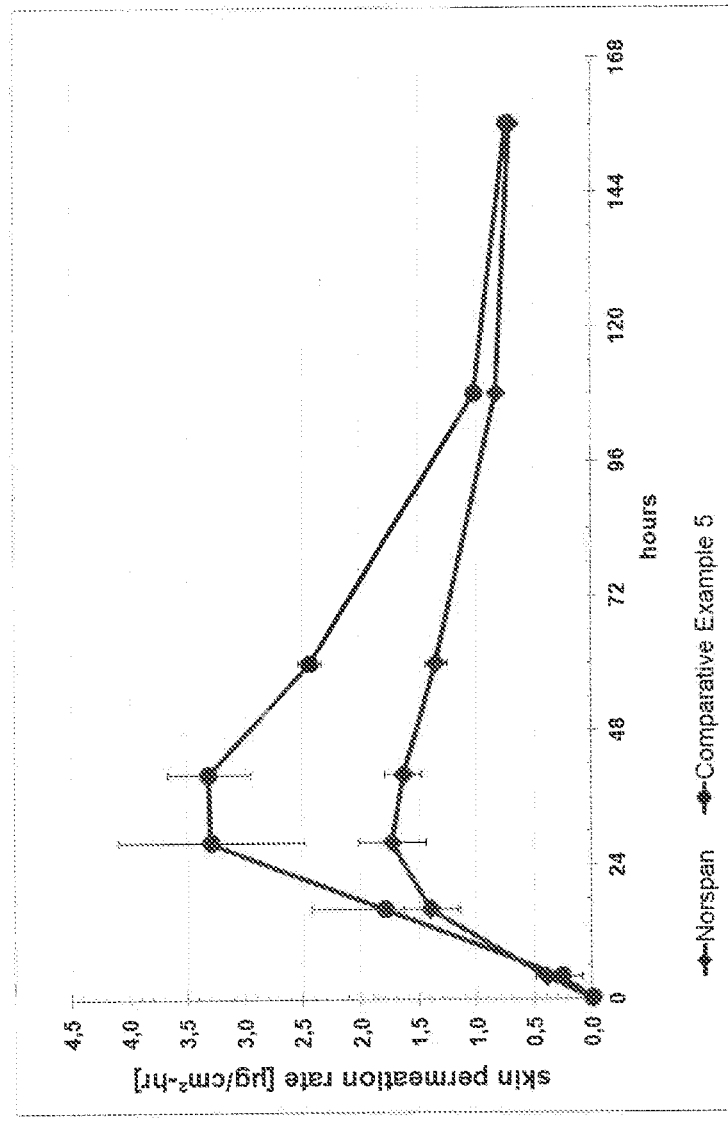
FIG. 3 depicts the mean non-cumulative skin permeation rate for Comparative Example 5 and Norspan®.
Figure 4:
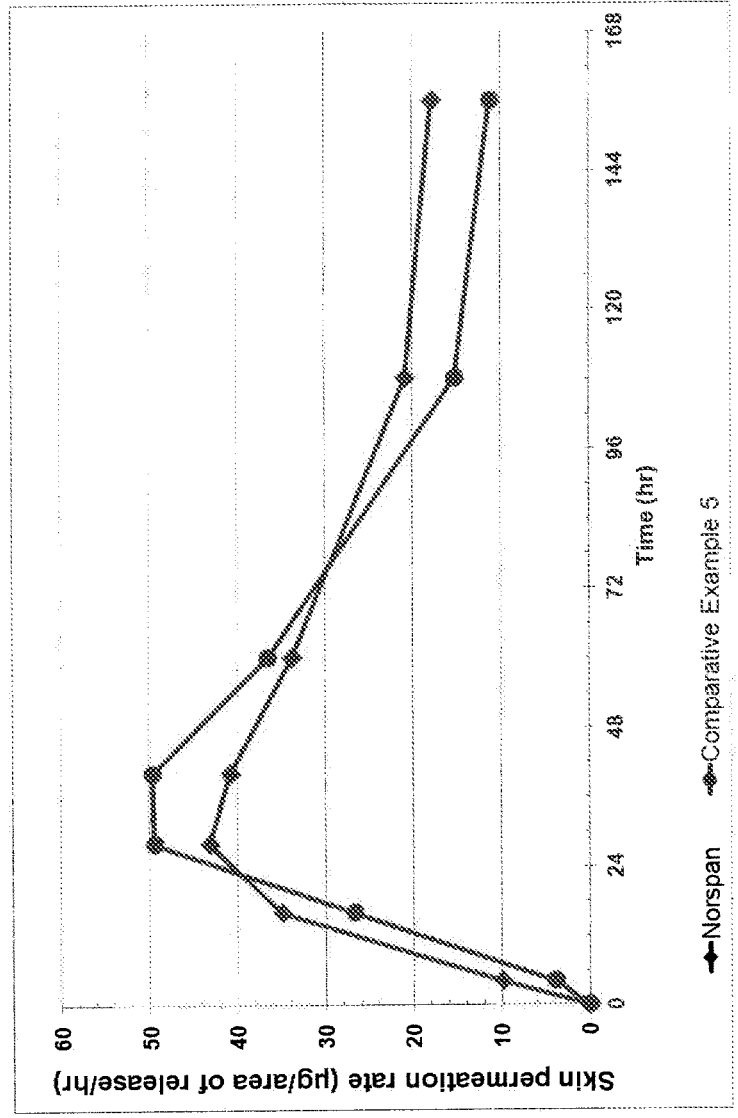
FIG. 4 depicts the mean non-cumulative skin permeation rate of the of the transdermal therapeutic systems. The area of release of the transdermal therapeutic system according to Comparative Example 5 being 15 cm$^2$ and the area of release for Norspan® being 25 cm$^2$. The amount of buprenorphine base for Comparative Example 5 being 6.75 mg and the amount of buprenorphine base for Norspan® being 20 mg.

According to certain embodiments, the TTS provides a cumulative release as measured in a Franz diffusion cell as mentioned above of about 220 µg/cm$^2$ to about 640 µg/cm$^2$ over a time period of 168 hours, or of about 400 µg/cm$^2$ to about 640 µg/cm$^2$, or of about 450 µg/cm$^2$ to about 640 µg/cm$^2$, or of about 500 µg/cm$^2$ to about 640 µg/cm$^2$, or of about 600 µg/cm$^2$ to about 640 µg/cm$^2$ over a time period of 168 hours. The commercial product Norspan® provides a cumulative release of about 175.29 µg/cm$^2$ in said test. As can be seen from FIG. 2, comparable skin permeation rates are measured using the 25 cm$^2$ Norspan® TTS including 20 mg buprenorphine base and TTS examples 1 to 4 in accordance with the invention with an area of 10 cm$^2$ and including 12 mg buprenorphine base. This corresponds to about a 60% size reduction and a reduction of about 40% in the amount of used buprenorphine base.

According to certain embodiments, the TTS provides a non-cumulative skin permeation rate of buprenorphine base as measured in a Franz diffusion cell of
2 µg/cm$^2$ to 10 µg/cm$^2$ in the first 8 hours,
20 µg/cm$^2$ to 80 µg/cm$^2$ from hour 8 to hour 24,
20 µg/cm$^2$ to 80 µg/cm$^2$ from hour 24 to hour 32,
30 µg/cm$^2$ to 120 µg/cm$^2$ from hour 32 to hour 48,
40 µg/cm$^2$ to 150 µg/cm$^2$ from hour 48 to hour 72,
100 µg/cm$^2$ to 300 µg/cm$^2$ from hour 72 to hour 144, and
30 µg/cm$^2$ to 100 µg/cm$^2$ from hour 144 to hour 168.

According to certain embodiments, the TTS provides a non-cumulative skin permeation rate of buprenorphine base as measured in a Franz diffusion cell of
2 µg/cm$^2$ to 6 µg/cm$^2$ in the first 8 hours,
25 µg/cm$^2$ to 60 µg/cm$^2$ from hour 8 to hour 24,
25 µg/cm$^2$ to 60 µg/cm$^2$ from hour 24 to hour 32,
40 µg/cm$^2$ to 100 µg/cm$^2$ from hour 32 to hour 48,
50 µg/cm$^2$ to 140 µg/cm$^2$ from hour 48 to hour 72,
100 µg/cm$^2$ to 280 µg/cm$^2$ from hour 72 to hour 144, and
30 µg/cm$^2$ to 100 µg/cm$^2$ from hour 144 to hour 168.

According to certain embodiments, the TTS provides a non-cumulative skin permeation rate of buprenorphine base as measured in a Franz diffusion cell of
3 µg/cm$^2$ to 6 µg/cm$^2$ in the first 8 hours,
30 µg/cm$^2$ to 50 µg/cm$^2$ from hour 8 to hour 24,
30 µg/cm$^2$ to 50 µg/cm$^2$ from hour 24 to hour 32,
60 µg/cm$^2$ to 90 µg/cm$^2$ from hour 32 to hour 48,
100 µg/cm$^2$ to 130 µg/cm$^2$ from hour 48 to hour 72,
200 µg/cm$^2$ to 280 µg/cm$^2$ from hour 72 to hour 144, and
60 µg/cm$^2$ to 100 µg/cm$^2$ from hour 144 to hour 168.

The commercial product Norspan® provides a non-cumulative skin permeation rate of buprenorphine base as measured in a Franz diffusion cell in the same setting of
3.19 µg/cm$^2$ in the first 8 hours,
22.40 µg/cm$^2$ from hour 8 to hour 24,
13.83 µg/cm$^2$ from hour 24 to hour 32,
26.17 µg/cm$^2$ from hour 32 to hour 48,
32.43 µg/cm$^2$ from hour 48 to hour 72,
60.10 µg/cm$^2$ from hour 72 to hour 144, and
17.17 µg/cm$^2$ from hour 144 to hour 168.

Method of Treatment/Medical Use

According to one aspect, the transdermal therapeutic system in accordance with the invention and as described above in detail is for use in a method of treating pain. The Method comprises in particular the application of the TTS for about 168 hours (corresponding to 7 days or one week) on the skin of a patient. According to other methods in accordance with the invention the TTS can be applied for more than about 96 hours corresponding to more than 4 days, or about 120 hours corresponding to 5 days and about 144 hours corresponding to 6 days. The application for about 168 hours is preferred.

According to one aspect, the invention relates to a method of treatment wherein a set of five different transdermal therapeutic systems corresponding to different dosage strengths and corresponding different nominal mean release rates and/or mean release rates over about 168 hours of administration is used, wherein:
the first transdermal therapeutic system provides a size of said buprenorphine-containing pressure-sensitive adhesive layer providing the area of release ranging from about 1.5 cm$^2$ to about 5.5 cm$^2$ and contains an amount of said buprenorphine from about 1 mg to about 4.5 mg buprenorphine base or an equimolar amount of a pharmaceutically acceptable salt thereof and provides a mean release rate of buprenorphine ranging from about 2.5 to about 7.5 µg/hr or from about 4 to about 6 µg/hr, and/or provides a nominal mean release rate of buprenorphine of about 5 µg/hr over about 168 hours of administration; and
the second transdermal therapeutic system provides a size of said buprenorphine-containing pressure-sensitive adhesive layer providing the area of release ranging from about 3 cm$^2$ to about 9 cm$^2$ and contains an amount of said buprenorphine from about 4 mg to about 9 mg buprenorphine base or an equimolar amount of a pharmaceutically acceptable salt thereof and provides a mean release rate of buprenorphine ranging from about 8 to about 12 µg/hr or from about 9 to about 11 µg/hr, and/or provides a nominal mean release rate of buprenorphine of about 10 µg/hr over about 168 hours of administration; and
the third transdermal therapeutic system provides a size of said buprenorphine-containing pressure-sensitive adhesive layer providing the area of release ranging from about 6 cm$^2$ to about 14 cm$^2$ and contains an amount of said buprenorphine from about 8 mg to about 14 mg buprenorphine base or an equimolar amount of a pharmaceutically acceptable salt thereof and provides a mean release rate of buprenorphine ranging from about 15 to about 25 µg/hr or from about 17 to about 22 µg/hr, and/or provides a nominal mean release rate of buprenorphine of about 20 µg/hr over about 168 hours of administration; and
the fourth transdermal therapeutic system provides a size of said buprenorphine-containing pressure-sensitive adhesive layer providing the area of release ranging from about 13 cm$^2$ to about 17 cm$^2$ and contains an amount of said buprenorphine from about 15 mg to about 20 mg buprenorphine base or an equimolar amount of a pharmaceutically acceptable salt thereof and provides a mean release rate of buprenorphine ranging from about 26 to about 35 µg/hr or from about 27 to about 32 µg/hr, and/or provides a nominal mean release rate of buprenorphine of about 30 µg/hr over about 168 hours of administration; and
the fifth transdermal therapeutic system provides a size of said buprenorphine-containing pressure-sensitive adhesive layer providing the area of release ranging from about 16 cm$^2$ to about 24 cm$^2$ and contains an amount of said buprenorphine from about 20 mg to about 28 mg buprenorphine base or an equimolar amount of a pharmaceutically acceptable salt thereof and provides a mean release rate of buprenorphine ranging from about 36 to about 45 µg/hr or from about 38 to about 42 µg/hr, and/or provides a nominal mean release rate of buprenorphine of about 40 µg/hr over about 168 hours of administration.

The invention relates also to set of transdermal therapeutic systems, wherein:
the first transdermal therapeutic system provides a size of said buprenorphine-containing pressure-sensitive adhesive layer providing the area of release ranging from about 2 cm$^2$ to about 4 cm$^2$ and contains an amount of said buprenorphine from about 2 mg to about 4 mg buprenorphine base or an equimolar amount of a pharmaceutically acceptable salt thereof and provides a mean release rate of buprenorphine ranging from about 2.5 to about 7.5 µg/hr or from about 4 to about 6 µg/hr, and/or provides a nominal mean release rate of buprenorphine of about 5 µg/hr over about 168 hours of administration; and
the second transdermal therapeutic system provides a size of said buprenorphine-containing pressure-sensitive adhesive layer providing the area of release ranging from about 4.5 cm$^2$ to about 7.5 cm$^2$ and contains an amount of said buprenorphine from about 5 mg to about 8 mg buprenorphine base or an equimolar amount of a pharmaceutically acceptable salt thereof and provides a mean release rate of buprenorphine ranging from about 8 to about 12 µg/hr or from about 9 to about 11 µg/hr, and/or provides a nominal mean release rate of buprenorphine of about 10 µg/hr over about 168 hours of administration; and
the third transdermal therapeutic system provides a size of said buprenorphine-containing pressure-sensitive adhesive layer providing the area of release ranging from about 8 cm$^2$ to about 12 cm$^2$ and contains an amount of said buprenorphine from about 10 mg to about 14 mg buprenorphine base or an equimolar amount of a pharmaceutically acceptable salt thereof and provides a mean release rate of buprenorphine ranging from about 15 to about 25 µg/hr or from about 17 to about 22 µg/hr, and/or provides a nominal mean release rate of buprenorphine of about 20 µg/hr over about 168 hours of administration; and
the fourth transdermal therapeutic system provides a size of said buprenorphine-containing pressure-sensitive adhesive layer providing the area of release ranging from about 13 cm² to about 16 cm² and contains an amount of said buprenorphine from about 16 mg to about 19 mg buprenorphine base or an equimolar amount of a pharmaceutically acceptable salt thereof and provides a mean release rate of buprenorphine ranging from about 26 to about 35 µg/hr or from about 27 to about 32 µg/hr, and/or provides a nominal mean release rate of buprenorphine of about 30 µg/hr over about 168 hours of administration; and the fifth transdermal therapeutic system provides a size of said buprenorphine-containing pressure-sensitive adhesive layer providing the area of release ranging from about 17 cm² to about 22 cm² and contains an amount of said buprenorphine from about 21 mg to about 26 mg buprenorphine base or an equimolar amount of a pharmaceutically acceptable salt thereof and provides a mean release rate of buprenorphine ranging from about 36 to about 45 µg/hr or from about 38 to about 42 µg/hr, and/or provides a nominal mean release rate of buprenorphine of about 40 µg/hr over about 168 hours of administration.

The invention relates also to set of different transdermal therapeutic, wherein:

the first transdermal therapeutic system provides a size of said buprenorphine-containing pressure-sensitive adhesive layer providing the area of release ranging from about 2 cm² to about 3 cm² and contains an amount of said buprenorphine from about 2.5 mg to about 4 mg buprenorphine base or an equimolar amount of a pharmaceutically acceptable salt thereof and provides a mean release rate of buprenorphine ranging from about 2.5 to about 7.5 µg/hr or from about 4 to about 6 µg/hr, and/or provides a nominal mean release rate of buprenorphine of about 5 µg/hr over about 168 hours of administration; and the second transdermal therapeutic system provides a size of said buprenorphine-containing pressure-sensitive adhesive layer providing the area of release ranging from about 4.5 cm² to about 6 cm² and contains an amount of said buprenorphine from about 5 mg to about 7 mg buprenorphine base or an equimolar amount of a pharmaceutically acceptable salt thereof and provides a mean release rate of buprenorphine ranging from about 8 to about 12 µg/hr or from about 9 to about 11 µg/hr, and/or provides a nominal mean release rate of buprenorphine of about 10 µg/hr over about 168 hours of administration; and the third transdermal therapeutic system provides a size of said buprenorphine-containing pressure-sensitive adhesive layer providing the area of release ranging from about 9 cm² to about 11 cm² and contains an amount of said buprenorphine from about 11 mg to about 13 mg buprenorphine base or an equimolar amount of a pharmaceutically acceptable salt thereof and provides a mean release rate of buprenorphine ranging from about 15 to about 25 µg/hr or from about 17 to about 22 µg/hr, and/or provides a nominal mean release rate of buprenorphine of about 20 µg/rh over about 168 hours of administration; and the fourth transdermal therapeutic system provides a size of said buprenorphine-containing pressure-sensitive adhesive layer providing the area of release ranging from about 14 cm² to about 16 cm² and contains an amount of said buprenorphine from about 17 mg to about 19 mg buprenorphine base or an equimolar amount of a pharmaceutically acceptable salt thereof and provides a mean release rate of buprenorphine ranging from about 26 to about 35 µg/hr or from about 27 to about 32 µg/hr, or about 30 µg/hr over about 168 hours of administration; and the fifth transdermal therapeutic system provides a size of said buprenorphine-containing pressure-sensitive adhesive layer providing the area of release ranging from about 18 cm² to about 21 cm² and contains an amount of said buprenorphine from about 22 mg to about 25 mg buprenorphine base or an equimolar amount of a pharmaceutically acceptable salt thereof and provides a mean release rate of buprenorphine ranging from about 36 to about 45 µg/hr or from about 38 to about 42 µg/hr, and/or provides a nominal mean release rate of buprenorphine of about 40 µg/hr over about 168 hours of administration.

According to one aspect, the invention relates to a method of treating pain in a patient wherein said patient is treated with one appropriately selected TTS from a set of two (first and second, or second and third, or third and fourth, or fourth and fifth TTS, or any other combination of two of the five different dosage strengths), three (first to third, or second to fourth or third to fifth TTS, or any other combination of three of the five different dosage strengths), four (first to fourth or second to fifth TTS, or any other combination of four of the five different dosage strengths) or five (first to fifth TTS) different transdermal therapeutic systems corresponding to different dosage strengths and corresponding different nominal mean release rates and/or mean release rates over about 168 hours of administration is used, wherein:

the first transdermal therapeutic system provides a size of said buprenorphine-containing pressure-sensitive adhesive layer providing the area of release ranging from about 1 cm² to about 4.8 cm² and contains an amount of said buprenorphine from about 1 mg to about 4 mg buprenorphine base or an equimolar amount of a pharmaceutically acceptable salt thereof and provides a mean release rate of buprenorphine of at least about 2 µg/hr, or of from about 2.5 to about 7.5 µg/hr or from about 4 to about 6 µg/hr, and/or provides a nominal mean release rate of buprenorphine of about 5 µg/hr over about 168 hours of administration; and the second transdermal therapeutic system provides a size of said buprenorphine-containing pressure-sensitive adhesive layer providing the area of release ranging from about 3 cm² to about 9.5 cm² and contains an amount of said buprenorphine from about 3.5 mg to about 8 mg buprenorphine base or an equimolar amount of a pharmaceutically acceptable salt thereof and provides a mean release rate of buprenorphine of at least about 6 µg/hr, or of from about 8 to about 12 µg/hr or from about 9 to about 11 µg/hr, and/or provides a nominal mean release rate of buprenorphine of about 10 µg/hr over about 168 hours of administration; and the third transdermal therapeutic system provides a size of said buprenorphine-containing pressure-sensitive adhesive layer providing the area of release ranging from about 6 cm² to about 19 cm² and contains an amount of said buprenorphine from about 6.5 mg to about 16 mg buprenorphine base or an equimolar amount of a pharmaceutically acceptable salt thereof and provides a mean release rate of buprenorphine of at least about 11 µg/hr, or of from about 15 to about 25 µg/hr or from about 17 to about 22 µg/hr, and/or provides a nominal mean release rate of buprenorphine of about 20 µg/hr over about 168 hours of administration; and the fourth transdermal therapeutic system provides a size of said buprenorphine-containing pressure-sensitive adhesive layer providing the area of release ranging from about 12 cm² to about 28.5 cm² and contains an amount of said buprenorphine from about 11.5 mg to about 24 mg buprenorphine base or an equimolar amount of a pharmaceutically acceptable salt thereof and provides a mean release rate of buprenorphine of at least about 21 µg/hr, or of from about 26 to about 35 µg/hr or from about 27 to about 32 µg/hr, and/or provides a nominal mean release rate of buprenorphine of about 30 µg/hr over about 168 hours of administration; and the fifth transdermal therapeutic system provides a size of said buprenorphine-containing pressure-sensitive adhesive layer providing the area of release ranging from about 16 cm² to about 38 cm² and contains an amount of said buprenorphine from about 15 mg to about 32 mg buprenorphine base or an equimolar amount of a pharmaceutically acceptable salt thereof and provides a mean release rate of buprenorphine of at least about 31 µg/hr, or of from about 36 to about 45 µg/hr or from about 38 to about 42 µg/hr, and/or provides a nominal mean release rate of buprenorphine of about 40 µg/hr over about 168 hours of administration.

The invention relates also to set of transdermal therapeutic systems, wherein:
the first transdermal therapeutic system provides a size of said buprenorphine-containing pressure-sensitive adhesive layer providing the area of release ranging from about 1 cm² to about 4.5 cm² and contains an amount of said buprenorphine from about 1 mg to about 3.5 mg buprenorphine base or an equimolar amount of a pharmaceutically acceptable salt thereof and provides a mean release rate of buprenorphine of at least about 2 µg/hr, or of from about 2.5 to about 7.5 µg/hr or from about 4 to about 6 µg/hr, and/or provides a nominal mean release rate of buprenorphine of about 5 µg/hr over about 168 hours of administration; and
the second transdermal therapeutic system provides a size of said buprenorphine-containing pressure-sensitive adhesive layer providing the area of release ranging from about 3 cm² to about 9 cm² and contains an amount of said buprenorphine from about 3.5 mg to about 7 mg buprenorphine base or an equimolar amount of a pharmaceutically acceptable salt thereof and provides a mean release rate of buprenorphine of at least about 6 µg/hr, or of from about 8 to about 12 µg/hr or from about 9 to about 11 µg/hr, and/or provides a nominal mean release rate of buprenorphine of about 10 µg/hr over about 168 hours of administration; and
the third transdermal therapeutic system provides a size of said buprenorphine-containing pressure-sensitive adhesive layer providing the area of release ranging from about 6 cm² to about 18 cm² and contains an amount of said buprenorphine from about 6.5 mg to about 14 mg buprenorphine base or an equimolar amount of a pharmaceutically acceptable salt thereof and provides a mean release rate of buprenorphine of at least about 11 µg/hr, or of from about 15 to about 25 µg/hr or from about 17 to about 22 µg/hr, and/or provides a nominal mean release rate of buprenorphine of about 20 µg/hr over about 168 hours of administration; and
the fourth transdermal therapeutic system provides a size of said buprenorphine-containing pressure-sensitive adhesive layer providing the area of release ranging from about 12 cm² to about 27 cm² and contains an amount of said buprenorphine from about 11.5 mg to about 21 mg buprenorphine base or an equimolar amount of a pharmaceutically acceptable salt thereof and provides a mean release rate of buprenorphine of at least about 21 µg/hr, or of from about 26 to about 35 µg/hr or from about 27 to about 32 µg/hr, and/or provides a nominal mean release rate of buprenorphine of about 30 µg/hr over about 168 hours of administration; and
the fifth transdermal therapeutic system provides a size of said buprenorphine-containing pressure-sensitive adhesive layer providing the area of release ranging from about 16 cm² to about 35 cm² and contains an amount of said buprenorphine from about 15 mg to about 28 mg buprenorphine base or an equimolar amount of a pharmaceutically acceptable salt thereof and provides a mean release rate of buprenorphine of at least about 31 µg/hr, or of from about 36 to about 45 µg/hr or from about 38 to about 42 µg/hr, and/or provides a nominal mean release rate of buprenorphine of about 40 µg/hr over about 168 hours of administration.

The invention relates also to set of different transdermal therapeutic, wherein:
the first transdermal therapeutic system provides a size of said buprenorphine-containing pressure-sensitive adhesive layer providing the area of release ranging from about 2.5 cm² to about 4 cm² and contains an amount of said buprenorphine from about 1 mg to about 3 mg buprenorphine base or an equimolar amount of a pharmaceutically acceptable salt thereof and provides a mean release rate of buprenorphine of at least about 2 µg/hr, or of from about 2.5 to about 7.5 µg/hr or from about 4 to about 6 µg/hr, and/or provides a nominal mean release rate of buprenorphine of about 5 µg/hr over about 168 hours of administration; and
the second transdermal therapeutic system provides a size of said buprenorphine-containing pressure-sensitive adhesive layer providing the area of release ranging from about 5 cm² to about 8 cm² and contains an amount of said buprenorphine from about 3.5 mg to about 6 mg buprenorphine base or an equimolar amount of a pharmaceutically acceptable salt thereof and provides a mean release rate of buprenorphine of at least about 6 µg/hr, or of from about 8 to about 12 µg/hr or from about 9 to about 11 µg/hr, and/or provides a nominal mean release rate of buprenorphine of about 10 µg/hr over about 168 hours of administration; and
the third transdermal therapeutic system provides a size of said buprenorphine-containing pressure-sensitive adhesive layer providing the area of release ranging from about 10 cm² to about 16 cm² and contains an amount of said buprenorphine from about 6.5 mg to about 11 mg buprenorphine base or an equimolar amount of a pharmaceutically acceptable salt thereof and provides a mean release rate of buprenorphine of at least about 11 µg/hr, or of from about 15 to about 25 µg/hr or from about 17 to about 22 µg/hr, and/or provides a nominal mean release rate of buprenorphine of about 20 µg/hr over about 168 hours of administration; and
the fourth transdermal therapeutic system provides a size of said buprenorphine-containing pressure-sensitive adhesive layer providing the area of release ranging from about 17 cm² to about 23 cm² and contains an amount of said buprenorphine from about 11.5 mg to about 14 mg buprenorphine base or an equimolar amount of a pharmaceutically acceptable salt thereof and provides a mean release rate of buprenorphine of at least about 21 µg/hr, or of from about 26 to about 35 µg/hr or from about 27 to about 32 µg/hr, and/or provides a nominal mean release rate of buprenorphine of about 30 µg/hr over about 168 hours of administration; and
the fifth transdermal therapeutic system provides a size of said buprenorphine-containing pressure-sensitive adhesive layer providing the area of release ranging from about 23.5 cm² to about 32 cm² and contains an amount of said buprenorphine from about 15 mg to about 24 mg buprenorphine base or an equimolar amount of a pharmaceutically acceptable salt thereof and provides a mean release rate of buprenorphine of at least about 31 µg/hr, or of from about 36 to about 45 µg/hr or from about 38 to about 42 µg/hr, and/or provides a nominal mean release rate of buprenorphine of about 40 µg/hr over about 168 hours of administration.

According to one aspect, the invention relates to a method of treating pain in a patient wherein a patient is treated with one appropriately selected TTS from a set of different transdermal therapeutic systems as described in the previous paragraphs, wherein:
the first transdermal therapeutic system provides a mean AUCt of more than 7,000 pg.hr/ml, preferably more than 8,000 pg.hr/ml, or of from more than 7,000 pg.hr/ml to about 16,000 pg.hr/ml, or of from more than 8,000 pg.hr/ml to about 16,000 pg.hr/ml over about 168 hours of administration after a single-dose administration to a subject population; and the second transdermal therapeutic system provides a mean AUCt of more than 14,000 pg.hr/ml, preferably of more than 16,000 pg.hr/ml, or of from more than 14,000 pg.hr/ml to about 32,000 pg.hr/ml, or of from more than 16,000 pg.hr/ml to about 32,000 pg.hr/ml over about 168 hours of administration after a single-dose administration to a subject population; and the third transdermal therapeutic system provides a mean AUCt of more than 28,000 pg.hr/ml, preferably of more than 32,000 pg.hr/ml, or of from more than 28,000 pg.hr/ml to about 64,000 pg.hr/ml, or of from more than 32,000 pg.hr/ml to about 64,000 pg.hr/ml over about 168 hours of administration after a single-dose administration to a subject population; and the fourth transdermal therapeutic system provides a mean AUCt of more than 42,000 pg.hr/ml, preferably of more than 48,000 pg.hr/ml, or of from more than 42,000 pg.hr/ml to about 96,000 pg.hr/ml, or of from more than 48,000 pg.hr/ml to about 96,000 pg.hr/ml over about 168 hours of administration after a single-dose administration to a subject population; and the fifth transdermal therapeutic system provides a mean AUCt of more than 62,000 pg.hr/ml, preferably of more than 64,000 pg.hr/ml, or of from more than 62,000 pg.hr/ml to about 128,000 pg.hr/ml, or of from more than 64,000 pg.hr/ml to about 128,000 pg.hr/ml over about 168 hours of administration after a single-dose administration to a subject population.

According to one aspect, the invention relates to a method of treatment described in the previous paragraphs, wherein the transdermal therapeutic system provides a mean AUCt per area of release of more than 1,700 pg.hr/ml-cm$^2$, or of more than 1,900 pg.hr/ml-cm$^2$, or of more than 2,300 pg.hr/ml-cm$^2$ over about 168 hours of administration after a single-dose administration to a subject population or provides a mean AUCt per area of release of from more than 1,700 pg.hr/ml-cm$^2$ to about 5,000 pg.hr/ml-cm$^2$, or of from more than 1,900 pg.hr/ml-cm$^2$ to about 5,000 pg.hr/ml-cm$^2$, or of from more than 2,300 pg.hr/ml-cm$^2$ to about 5,000 pg.hr/ml-cm$^2$ over about 168 hours of administration after a single-dose administration to a subject population.

According to one aspect, the invention relates to a method of treatment described in the previous paragraphs, wherein the transdermal therapeutic system provides an arithmetic mean tmax of from about 60 hr to about 120 hr, preferably from about 66 hr to less than 108 hr, or from about 72 hr to about 96 hr after a single-dose administration to a subject population.

Method of Manufacture

According to one further aspect, the invention relates to a method of manufacture of a transdermal therapeutic system for the transdermal administration of buprenorphine, comprising the steps of
1. providing a buprenorphine-containing adhesive mixture or solution comprising
  a) buprenorphine base or a pharmaceutically acceptable salt thereof
  b) a carboxylic acid (e.g., levulinic acid),
  c) a polymer-based pressure-sensitive adhesive, and
  d) solvent (e.g., heptane and ethanol)

2. coating said buprenorphine-containing adhesive mixture or solution on a film (e.g., polyethylene terephthalate film) in an amount to provide the desired dry weight,
3. drying said coated buprenorphine-containing adhesive mixture or solution to provide a buprenorphine-containing adhesive layer with the desired dry weight,
4. laminating said buprenorphine-containing adhesive layer to a backing layer (e.g., Scotchpak 1220 from 3M) to provide an buprenorphine-containing self-adhesive layer structure,
5. punching the individual systems from the buprenorphine-containing self-adhesive layer structure with the desired area of release, and
6. optionally adhering to the individual systems an active-free self-adhesive layer structure comprising also a backing layer and an active agent-free pressure-sensitive adhesive layer and which is larger than the individual systems of buprenorphine-containing self-adhesive layer structure.

In step 1 of said method of manufacture preferably buprenorphine base and levulinic acid are used and are suspended in ethanol and subsequently combined with the polymer-based pressure-sensitive adhesive based on polysiloxane in heptane to provide the buprenorphine-containing adhesive mixture or solution.

EXAMPLES

The present invention will now be more fully described with reference to the accompanying examples. It should be understood, however, that the following description is illustrative only and should not be taken in any way as a restriction of the invention.

Example 1

The composition of the buprenorphine base-containing adhesive solution is summarized in Table 1 below.

TABLE 1

| Ingredient (Trade Name) | Amt/unit (kg) |
| --- | --- |
| Buprenorphine base | 3.65 |
| Levulinic acid | 3.65 |
| Ethanol | 1.97 |
| Polysiloxane adhesive in n-heptane Solids content of 73% by weight (BIO-PSA 7-4301 from Dow Corning Healthcare) | 40.0 |
| n-heptane | 2.87 |
| Total | 52.14 |

In a stainless steel vessel, 3.65 kg of buprenorphine were suspended in 3.65 kg of levulinic acid and 1.97 kg of ethanol. With stirring, 40.0 kg of a polysiloxane adhesive in the form of a solution in n-heptane having a solids content of 73% by weight and 2.87 kg of heptane were added. The mixture was stirred until the buprenorphine base was fully dissolved, to give 52.14 kg of a buprenorphine-containing adhesive solution with 7% of buprenorphine, with a solids content of 70% (buprenorphine base-containing adhesive solution).

The buprenorphine base-containing adhesive solution was coated on an adhesive polyethylene terephthalate film (e.g., Scotchpak from 3M) using an Erichsen coater and the solvent was removed by drying at approximately 45° C. for 20 minutes. The coating thickness was chosen such that removal of the solvents results in a coating weight of the matrix layer of 120 g/m². This results in the 10% by weight of buprenorphine base and 10% by weight of levulinic acid in this matrix layer. The dried film was laminated with the backing layer (e.g Scotchpak from 3M) to provide the buprenorphine-containing self-adhesive layer structure.

The individual systems (TTS) were then punched from the buprenorphine-containing self-adhesive layer structure. In specific embodiments a TTS as described above can be provided with a further self-adhesive layer of larger surface area, preferably with rounded corners, comprising a pressure-sensitive adhesive matrix layer which is free of active ingredient and has a preferably skin-colored backing layer. This is of advantage when the TTS, on the basis of its physical properties alone, does not adhere sufficiently to the skin and/or when the buprenorphine-containing matrix layer, for the purpose of avoiding waste, has pronounced corners (square or rectangular shapes). The plasters are then punched out and sealed into pouches of the primary packaging material.

Example 2

The composition of the buprenorphine base-containing adhesive solution is summarized in Table 2 below.

TABLE 2

| Ingredient (Trade Name) | Amt/unit (kg) |
| --- | --- |
| Buprenorphine base | 3.65 |
| Levulinic acid | 2.56 |
| Ethanol | 1.83 |
| Polysiloxane adhesive in n-heptane Solids content of 73% by weight (BIO-PSA 7-4301 from Dow Corning Healthcare) | 41.49 |
| n-heptane | 2.61 |
| Total | 52.14 |

The process of manufacture was as described for Example 1. The coating thickness was also chosen such that removal of the solvents results in a coating weight of the matrix layer of 120 g/m² and thus resulted in 10% by weight buprenorphine base and 7% by weight levulinic acid in this matrix layer.

Example 3

The composition of the buprenorphine base-containing adhesive solution is summarized in Table 3 below.

TABLE 3

| Ingredient (Trade Name) | Amt/unit (kg) |
| --- | --- |
| Buprenorphine base | 3.65 |
| Levulinic acid | 3.65 |
| Ethanol | 1.97 |
| Polysiloxane adhesive in n-heptane Solids content of 74% by weight (BIO-PSA 7-4201 from Dow Corning Healthcare) | 39.46 |
| n-heptane | 3.41 |
| Total | 52.14 |

The process of manufacture was as described for Example 1. The coating thickness was also chosen such that removal of the solvents results in a coating weight of the matrix layer of 120 g/m² and thus resulted in 10% by weight buprenorphine base and 10% by weight levulinic acid in this matrix layer.

Example 4

The composition of the buprenorphine base-containing adhesive solution is summarized in Table 4 below.

TABLE 4

| Ingredient (Trade Name) | Amt/unit (kg) |
| --- | --- |
| Buprenorphine base | 3.65 |
| Levulinic acid | 2.56 |
| Ethanol | 1.83 |
| Polysiloxane adhesive in n-heptane Solids content of 74% by weight (BIO-PSA 7-4201 from Dow Corning Healthcare) | 40.93 |
| n-heptane | 3.17 |
| Total | 52.14 |

The process of manufacture was as described for Example 1. The coating thickness was also chosen such that removal of the solvents results in a coating weight of the matrix layer of 120 g/m² and thus resulted in 10% by weight buprenorphine base and 7% by weight levulinic acid in this matrix layer.

Comparative Example 5

In Comparative Example 5, a transdermal therapeutic system comprising an active-agent-free skin contact layer on a buprenorphine-containing matrix layer was prepared.

The composition of the buprenorphine base-containing adhesive solution is summarized in Table 5a below and the composition of the active-agent-free skin contact layer is summarized in Table 5b below.

TABLE 5a

| Ingredient (Trade Name) | Amt/unit (kg) |
| --- | --- |
| Buprenorphine base | 0.42 |
| Levulinic acid | 0.56 |
| Ethanol | 0.28 |
| Polysiloxane adhesive in n-heptane Solids content of 74% by weight (BIO-PSA 7-4201 from Dow Corning Healthcare) | 6.25 |
| n-heptane | 0.49 |
| Total | 8.00 |

TABLE 5b

| Ingredient (Trade Name) | Amt/unit (kg) |
| --- | --- |
| Polyacrylate adhesive prepared from 2-ethylhexyl acrylate, vinyl acetate and 2-hydroxyethyl acrylate in Ethyl acetate Solids content 50.5% | 3.69 |
| Ethyl acetate | 1.64 |
| Total | 5.33 |

In a stainless steel vessel, 0.42 kg of buprenorphine were suspended in 0.56 kg of levulinic acid and 0.28 kg of ethanol. With stirring, 6.25 kg of a polysiloxane adhesive in the form of a solution in n-heptane having a solids content of 74% by weight and 0.49 kg of heptane were added. The mixture was stirred until the buprenorphine base was fully dissolved, to give 8.00 kg of a buprenorphine-containing adhesive solution with 5.25% of buprenorphine, with a solids content of 70% (buprenorphine base-containing adhesive solution).

For the skin contact layer, a polyacrylate adhesive prepared from 2-ethylhexyl acrylate, vinyl acetate and 2-hydroxyethyl acrylate were used. 3.69 kg of a solution of this adhesive, with a solids content of 50.5% by weight, was admixed with 1.64 kg of ethyl acetate, following homogenization resulting in 5.33 kg of active-agent-free polyacrylate solution with a solids content of 35% (buprenorphine base-free adhesive solution)

The buprenorphine base-containing adhesive solution was coated on an adhesive polyethylene terephthalate film (e.g., Scotchpak from 3M) using an Erichsen coater and the solvent was removed by drying at approximately 50° C. for about 10 minutes to provide the buprenorphine base-containing matrix layer. The coating thickness was chosen such that removal of the solvents results in a coating weight of the buprenorphine base-containing matrix layer of 60 g/m$^2$. This results in the 7.5% by weight of buprenorphine base and 10% by weight of levulinic acid in this buprenorphine base-containing matrix layer. The dried film was laminated with the backing layer (e.g Scotchpak from 3M).

The active-agent-free polyacrylate adhesive solution was likewise coated onto an adhesively treated film (the later protective film to be removed before the systems are used) and the organic solvents were removed to produce the skin contact layer. The coating thickness of the resulting skin contact layer ought to amount, following removal of the solvents, to approximately 20 g/m$^2$. The adhesively treated film was then removed from the buprenorphine base-containing matrix layer produced first, and the buprenorphine base-containing matrix layer was laminated onto the skin contact layer.

The individual systems (TTS) were then punched from the buprenorphine-containing self-adhesive layer structure. In specific embodiments a TTS as described above can be provided with a further self-adhesive layer of larger surface area, preferably with rounded corners, comprising a pressure-sensitive adhesive matrix layer which is free of active ingredient and has a preferably skin-colored backing layer. This is of advantage when the TTS, on the basis of its physical properties alone, does not adhere sufficiently to the skin and/or when the buprenorphine-containing matrix layer, for the purpose of avoiding waste, has pronounced corners (square or rectangular shapes). The plasters are then punched out and sealed into pouches of the primary packaging material.

Example 6

In Example 6 the in-vitro releases and the corresponding skin permeation rates of Examples 1 to 4, Comparative Example 5 and Norspan® were determined by in vitro experiments in accordance with the OECD Guideline (adopted Apr. 13, 2004) carried out with a 9 ml Franz diffusion cell. Split thickness human skin from cosmetic surgeries (female breast, date of birth 1989) was used. A dermatome was used to prepare skin to a thickness of 800 μm, with an intact epidermis for all examples 1 to 4, Comparative Example 5 and the commercial product Norspan®. Diecuts with an area of 1.163 cm$^2$ were punched from examples 1 to 4 and Comparative Example 5, and were each tested against diecuts of the commercial product Norspan®. The concentrations of buprenorphine in the receptor medium of the Franz cell (phosphate buffer solution pH 5.5 with 0.1% saline azide as antibacteriological agent) at a temperature of 32±1° C. were measured. The results are shown in Tables 6.1 to 6.8 and FIGS. 1 to 4.

TABLE 6.1

| Elapsed time (hr) | Non-cumulative release [μg/cm$^2$] n = 3 (SD) | | | | |
|---|---|---|---|---|---|
| | Example 1 | Example 2 | Example 3 | Example 4 | Norspan ® |
| 0 | 0 | 0 | 0 | 0 | 0 |
| 8 | 4.06 | 3.53 | 2.35 | 3.33 | 3.19 |
| | (1.49) | (0.70) | (0.65) | (1.89) | (0.77) |
| 24 | 44.60 | 33.60 | 36.47 | 28.73 | 22.40 |
| | (16.99) | (7.10) | (10.19) | (8.84) | (3.76) |
| 32 | 34.00 | 31.93 | 36.47 | 22.10 | 13.83 |
| | (11.58) | (13.14) | (11.37) | (5.54) | (2.32) |
| 48 | 73.77 | 58.17 | 94.53 | 49.60 | 26.17 |
| | (20.38) | (6.62) | (20.48) | (11.47) | (2.46) |
| 72 | 113.83 | 87.83 | 131.67 | 74.10 | 32.43 |
| | (23.49) | (8.76) | (12.70) | (14.25) | (2.23) |
| 144 | 272.00 | 210.67 | 166.00 | 181.33 | 60.10 |
| | (22.52) | (8.08) | (28.62) | (28.22) | (2.02) |
| 168 | 78.30 | 65.60 | 26.73 | 60.97 | 17.17 |
| | (2.65) | (6.25) | (5.09) | (9.69) | (1.72) |

TABLE 6.2

| Elapsed time (hr) | Non-cumulative release [μg/cm$^2$] n = 3 (SD) | |
|---|---|---|
| | Comparative Example 5 | Norspan ® |
| 0 | 0 | 0 |
| 8 | 2.12 | 3.19 |
| | (1.44) | (0.77) |
| 24 | 28.60 | 22.40 |
| | (10.19) | (3.76) |
| 32 | 26.37 | 13.83 |
| | (6.47) | (2.32) |
| 48 | 53.03 | 26.17 |
| | (5.80) | (2.46) |
| 72 | 58.47 | 32.43 |
| | (2.42) | (2.23) |
| 144 | 73.27 | 60.10 |
| | (4.63) | (2.02) |
| 168 | 17.87 | 17.17 |
| | (1.35) | (1.72) |

TABLE 6.3

| Elapsed time (hr) | Sample interval (hr) | Mean non-cumulative skin permeation rate [μg/cm$^2$-hr] n = 3 (SD) | | | | |
|---|---|---|---|---|---|---|
| | | Example 1 | Example 2 | Example 3 | Example 4 | Norspan ® |
| 0 | 0 | 0 | 0 | 0 | 0 | 0 |
| 8 | 8 | 0.51 | 0.44 | 0.29 | 0.42 | 0.40 |
| | | (0.19) | (0.09) | (0.08) | (0.24) | (0.10) |
| 24 | 16 | 2.79 | 2.10 | 2.28 | 1.80 | 1.40 |
| | | (1.06) | (0.44) | (0.64) | (0.55) | (0.24) |
| 32 | 8 | 4.25 | 3.99 | 4.56 | 2.76 | 1.73 |
| | | (1.45) | (1.64) | (1.42) | (0.69) | (0.29) |

TABLE 6.3-continued

Mean non-cumulative skin permeation rate [μg/cm$^2$-hr] n = 3 (SD)

| Elapsed time (hr) | Sample interval (hr) | Example 1 | Example 2 | Example 3 | Example 4 | Norspan ® |
|---|---|---|---|---|---|---|
| 48 | 16 | 4.61 | 3.64 | 5.91 | 3.10 | 1.64 |
|  |  | (1.27) | (0.41) | (1.28) | (0.72) | (0.15) |
| 72 | 24 | 4.74 | 3.66 | 5.49 | 3.09 | 1.35 |
|  |  | (0.98) | (0.37) | (0.53) | (0.59) | (0.09) |
| 144 | 72 | 3.78 | 2.93 | 2.31 | 2.52 | 0.83 |
|  |  | (0.31) | (0.11) | (0.40) | (0.39) | (0.03) |
| 168 | 24 | 3.26 | 2.73 | 1.11 | 2.54 | 0.72 |
|  |  | (0.11) | (0.26) | (0.21) | (0.40) | (0.07) |

TABLE 6.4

Mean non-cumulative skin permeation rate [μg/cm$^2$-hr] n = 3 (SD)

| Elapsed time (hr) | Sample interval (hr) | Comparative Example 5 | Norspan ® |
|---|---|---|---|
| 0 | 0 | 0 | 0 |
| 8 | 8 | 0.27 | 0.40 |
|  |  | (0.18) | (0.10) |
| 24 | 16 | 1.79 | 1.40 |
|  |  | (0.64) | (0.24) |
| 32 | 8 | 3.30 | 1.73 |
|  |  | (0.81) | (0.29) |
| 48 | 16 | 3.31 | 1.64 |
|  |  | (0.36) | (0.15) |
| 72 | 24 | 2.44 | 1.35 |
|  |  | (0.10) | (0.09) |
| 144 | 72 | 1.02 | 0.83 |
|  |  | (0.06) | (0.03) |
| 168 | 24 | 0.74 | 0.72 |
|  |  | (0.06) | (0.07) |

TABLE 6.5

Mean non-cumulative skin permeation rate [μg/cm$^2$-hr] n = 3 (SD) and per area of release [μg/hr]

| Elapsed time (hr) | Sample interval (hr) | Area of release (cm$^2$) | Example 1 | Example 2 | Example 3 | Example 4 | Norspan ® Area of release (25 cm$^2$) |
|---|---|---|---|---|---|---|---|
| 0 | 0 |  | 0 | 0 | 0 | 0 | 0 |
| 8 | 8 |  | 0.51 | 0.44 | 0.29 | 0.42 | 0.40 |
|  |  |  | (0.19) | (0.09) | (0.08) | (0.24) | (0.10) |
|  |  | 10 | 5.08 | 4.42 | 2.93 | 4.16 | 9.97 |
|  |  | 15 | 7.61 | 6.63 | 4.40 | 6.24 | 9.97 |
|  |  | 18.75 | 9.52 | 8.28 | 5.50 | 7.80 | 9.97 |
| 24 | 16 |  | 2.79 | 2.10 | 2.28 | 1.80 | 1.40 |
|  |  |  | (1.06) | (0.44) | (0.64) | (0.55) | (0.24) |
|  |  | 10 | 27.88 | 21.00 | 22.79 | 17.96 | 35.00 |
|  |  | 15 | 41.81 | 31.50 | 34.19 | 26.94 | 35.00 |
|  |  | 18.75 | 52.27 | 39.38 | 42.73 | 33.67 | 35.00 |
| 32 | 8 |  | 4.25 | 3.99 | 4.56 | 2.76 | 1.73 |
|  |  |  | (1.45) | (1.64) | (1.42) | (0.69) | (0.29) |
|  |  | 10 | 42.50 | 39.92 | 45.58 | 27.63 | 43.23 |
|  |  | 15 | 63.75 | 59.88 | 68.38 | 41.44 | 43.23 |
|  |  | 18.75 | 79.69 | 74.84 | 85.47 | 51.80 | 43.23 |
| 48 | 16 |  | 4.61 | 3.64 | 5.91 | 3.10 | 1.64 |
|  |  |  | (1.27) | (0.41) | (1.28) | (0.72) | (0.15) |
|  |  | 10 | 46.10 | 36.35 | 59.08 | 31.00 | 40.89 |
|  |  | 15 | 69.16 | 54.53 | 88.63 | 46.50 | 40.89 |
|  |  | 18.75 | 86.45 | 68.16 | 110.78 | 58.13 | 40.89 |
| 72 | 24 |  | 4.74 | 3.66 | 5.49 | 3.09 | 1.35 |
|  |  |  | (0.98) | (0.37) | (0.53) | (0.59) | (0.09) |
|  |  | 10 | 47.43 | 36.60 | 54.86 | 30.88 | 33.78 |
|  |  | 15 | 71.15 | 54.90 | 82.29 | 46.31 | 33.78 |
|  |  | 18.75 | 88.93 | 68.62 | 102.86 | 57.89 | 33.78 |
| 144 | 72 |  | 3.78 | 2.93 | 2.31 | 2.52 | 0.83 |
|  |  |  | (0.31) | (0.11) | (0.40) | (0.39) | (0.03) |
|  |  | 10 | 37.78 | 29.26 | 23.06 | 25.19 | 20.87 |
|  |  | 15 | 56.67 | 43.89 | 34.58 | 37.78 | 20.87 |
|  |  | 18.75 | 70.83 | 54.86 | 43.23 | 47.22 | 20.87 |
| 168 | 24 |  | 3.26 | 2.73 | 1.11 | 2.54 | 0.72 |
|  |  |  | (0.11) | (0.26) | (0.21) | (0.40) | (0.07) |
|  |  | 10 | 32.63 | 27.33 | 11.14 | 25.40 | 17.88 |
|  |  | 15 | 48.94 | 41.00 | 16.71 | 38.10 | 17.88 |
|  |  | 18.75 | 61.17 | 51.25 | 20.89 | 47.63 | 17.88 |

TABLE 6.6

Mean non-cumulative skin permeation rate [μg/cm²-hr]
n = 3 (SD) and
per area of release [μg/hr]

| Elapsed time (hr) | Sample interval (hr) | Area of release (cm²) | Comp. Example 5 | Norspan ® Area of release (25 cm²) |
|---|---|---|---|---|
| 0 | 0 | | 0 | 0 |
| 8 | 8 | | 0.27 | 0.40 |
| | | | (0.18) | (0.10) |
| | | 10 | 2.65 | 9.97 |
| | | 15 | 3.98 | 9.97 |
| | | 18.75 | 4.98 | 9.97 |
| 24 | 16 | | 1.79 | 1.40 |
| | | | (0.64) | (0.24) |
| | | 10 | 17.88 | 35.00 |
| | | 15 | 26.81 | 35.00 |
| | | 18.75 | 33.52 | 35.00 |
| 32 | 8 | | 3.30 | 1.73 |
| | | | (0.81) | (0.29) |
| | | 10 | 32.96 | 43.23 |
| | | 15 | 49.44 | 43.23 |
| | | 18.75 | 61.80 | 43.23 |
| 48 | 16 | | 3.31 | 1.64 |
| | | | (0.36) | (0.15) |
| | | 10 | 33.15 | 40.89 |
| | | 15 | 49.72 | 40.89 |
| | | 18.75 | 62.15 | 40.89 |
| 72 | 24 | | 2.44 | 1.35 |
| | | | (0.10) | (0.09) |
| | | 10 | 24.36 | 33.78 |
| | | 15 | 36.54 | 33.78 |
| | | 18.75 | 45.68 | 33.78 |
| 144 | 72 | | 1.02 | 0.83 |
| | | | (0.06) | (0.03) |
| | | 10 | 10.18 | 20.87 |
| | | 15 | 15.26 | 20.87 |
| | | 18.75 | 19.08 | 20.87 |
| 168 | 24 | | 0.74 | 0.72 |
| | | | (0.06) | (0.07) |
| | | 10 | 7.44 | 17.88 |
| | | 15 | 11.17 | 17.88 |
| | | 18.75 | 13.96 | 17.88 |

TABLE 6.7

Cumulative release after 168 hours of release [μg/cm²] n = 3

| Example 1 | Example 2 | Example 3 | Example 4 | Comparative Example 5 | Norspan ® |
|---|---|---|---|---|---|
| 620.56 | 491.33 | 494.22 | 420.16 | 259.72 | 175.29 |

TABLE 6.8

Mean cumulative skin permeation rate over 168 hours [μg/cm²-hr]

| Example 1 | Example 2 | Example 3 | Example 4 | Comparative Example 5 | Norspan ® |
|---|---|---|---|---|---|
| 3.69 | 2.92 | 2.94 | 2.50 | 1.55 | 1.04 |

Example 7

In Example 7, a pharmacokinetic study in healthy adult male and female subjects was conducted as part of a 2 stage, randomised, open-label, single-dose, 4-part crossover design pharmacokinetic study to assess the pharmacokinetics and potential of Example 1 TTS, Example 2 TTS and Comparative Example 5 TTS formulations for equivalence to the existing commercial product BuTrans®, also known as Norspan®.

The study treatments were as follows:

Test Treatments:
 Example 1 TTS—the amount of buprenorphine base being 12 mg; the area of release being 10 cm²—applied for 7 consecutive days.
 Example 2 TTS—the amount of buprenorphine base being 12 mg, the area of release being 10 cm²—applied for 7 consecutive days.
 Comparative Example 5 TTS—the amount of buprenorphine base being 6.75 mg; the area of release being 15 cm²—applied for 7 consecutive days.

Reference Treatment:
 BuTrans® 20 μg/hr (the amount of buprenorphine base being 20 mg; the area of release being 25 cm²)—applied for 7 consecutive days.

The treatments were each worn over a 7-day period. Each subject was randomised to both the order, and TTS site of the treatments to be delivered over the study periods.

As this study was conducted in healthy human subjects, the opioid antagonist naltrexone was co-administered to reduce opioid-related adverse events. 50 mg naltrexone were administered with 100 ml of water every 12 hours beginning −13 hours prior to TTS application and continuing until 215 hours post-TTS application.

Subject Selection
Number of Subjects
 It was anticipated that approximately 32 subjects would be randomized into stage 1 of the study, with 26 subjects targeted to complete stage 1 of the study. An adequate number of subjects were screened in the pre-treatment phase, i.e. within 21 days prior to the treatment phase to achieve this sample size.

Screening Procedure
 Screening procedures were performed for all potential subjects at a screening visit conducted within 21 days prior to the treatment phase, i.e. prior to Day −1 of study period 1. The following evaluations were performed after the subject has signed the study specific consent form:
 Inclusion/Exclusion criteria
 Demography (sex, date of birth, race) and body mass index (BMI)
 Medical history (including confirmation of eligibility from the subject's primary care physician)
 Physical examination including height, weight, and body mass index
 Haematology (haemoglobin, red blood cell count, haematocrit, platelets, white blood cell count and differential (neutrophils, lymphocytes, monocytes, eosinophils and basophils))
 Blood Chemistry (sodium, calcium, potassium, bicarbonate, chloride, urea, creatinine, uric acid, albumin, total protein, alkaline phosphatase, globulin, aspartate aminotransferase, alanine aminotransferase, gamma glutamyl-transferase, total bilirubin, direct bilirubin, glucose, inorganic phosphate, lactate dehydrogenase, triglyceride and cholesterol)
 Urinalysis (specific gravity, pH, protein, ketone, occult blood, glucose; and additional microscopy analysis will be undertaken if any abnormalities are detected to analyse for red blood cells, white blood cells, epithelial cells, bacteria, casts, and crystals)
 Urine drugs of abuse (opiates, cocaine metabolites, barbiturates, amphetamines, methadone, benzodiazepines, phencyclidine, methamphetamine, tricyclic antidepressants and cannabinoids) and alcohol test (urine or breath)

Serology testing (Human immunodeficiency virus (HIV), Hepatitis B surface antigen (HBsAg), Hepatitis C antibody)

12-lead Electrocardiogram (ECG)

Serum pregnancy test for females of child-bearing potential

Serum FSH for post-menopausal females

Vital signs (Pulse oximetry/oxygen saturation ($SpO_2$), supine respiration rate, supine blood pressure, supine pulse rate and oral temperature)

Medication history and concomitant medications will also be recorded.

Inclusion Criteria

Subjects who met the following criteria were included in the study.
1. Provide written informed consent.
2. Healthy male or female subjects aged 18 to 55 inclusive.
3. Female subjects who are sexually active or become sexually active must be willing to use highly effective methods of contraception throughout the study. A highly effective method of birth control is defined as one which results in a low failure rate (i.e. less than 1% per year) when used consistently and correctly such as sterilisation, implants, injectables, combined oral contraceptives, some IUDs (Intrauterine Device), or vasectomised partner.
4. Female subjects including those up to 1 year post-menopausal must have a negative serum pregnancy test.
5. Female subjects who have been post-menopausal for >1 year and have elevated serum follicle-stimulating hormone (FSH) or are treated with hormone replacement therapy (HRT).
6. Male subjects who are willing to use contraception with their partners throughout the study and for 10 days after completion of the study and agree to inform the Investigator if their partner becomes pregnant during this time.
7. Body weight ranging from 55 to 100 kg and a BMI ≥18 and ≤29.
8. Healthy and free of significant abnormal findings as determined by medical history, physical examination, vital signs, laboratory tests and ECG.
9. Willing to eat all the food supplied throughout the study.
10. The subject's primary care physician has confirmed within the last 12 months that there is nothing in the subject's medical history that would preclude their enrolment into a clinical study.
11. Will refrain from strenuous exercise during the entire study. They will not begin a new exercise program nor participate in any unusually strenuous physical exertion.

Exclusion Criteria

The following criteria excluded potential subjects from the study.
1. Female subjects who are pregnant or lactating.
2. Any history of drug or alcohol abuse.
3. Any history of conditions that might interfere with drug absorption, distribution, metabolism or excretion.
4. Use of opioid or opioid antagonist-containing medication in the past 30 days.
5. Any history of frequent nausea or vomiting regardless of aetiology.
6. Any history of seizures or symptomatic head trauma.
7. Participation in a clinical drug study during the 90 days preceding the initial dose in this study or participation in any other study during this study.
8. Any significant illness during the 4 weeks preceding entry into this study.
9. A history of additional risk factors for Torsades de Pointes (e.g. heart failure, hypokalaemia, personal or family history of long QT syndrome, syncope, or family history of sudden death).
10. Abnormal cardiac conditions including any of the following:
    QTc interval greater than 450 msec at screening or at check-in before first dosing.
    Increase in QTc of more than 60 msec above pre-dose values of each study period.
11. Use of medication within 5 times the half-life or minimum 14 days for prescription medication or 7 days for over-the-counter preparations (including vitamins, herbal and/or mineral supplements), whichever is longer, before the first dose of study treatment and during the study (with the exception of the continued use of HRT and contraceptives). Note: subjects taking oral contraceptives containing CYP3A4 inhibitors such as gestodene should be excluded as this may lead to elevated plasma concentrations.
12. Refusal to abstain from caffeine or xanthine containing beverages entirely until the last study PK sample has been taken.
13. Weekly alcohol intake exceeding the equivalent of 14 units/week for females and 21 units/week for males.
14. Consumption of alcoholic beverages within 48 hours before study drug administration, and refusal to abstain from alcohol for the duration of the study confinement and for at least 72 hours after the last naltrexone dose.
15. History of smoking within 45 days of study drug administration and refusal to abstain from smoking during the study.
16. Blood or blood products donated within 90 days prior to study drug administration or any time during the study, except as required by this protocol.
17. Positive results of urine drug screen, alcohol test, pregnancy test, HBsAg, Hepatitis C antibody, or HIV tests.
18. Known hypersensitivity or sensitivity to buprenorphine, naltrexone or related compounds or any of the excipients or any contraindications as detailed in the Summary of Product Characteristics.
19. Clinically significant history of allergic reaction to wound dressings or elastoplast.
20. Subjects with tattoos or any dermatological disorder at the proposed sites of TTS application, or with a history of eczema/cutaneous atrophy.
21. Subjects who will not allow hair to be removed at the proposed TTS application sites which may prevent proper placement of the TTS.
22. Refusal to allow their primary care physician to be informed.

Subjects meeting all the inclusion criteria and none of the exclusion criteria were randomized into the study.

Treatment Phase Procedures

Randomisation

Randomisation was completed once all inclusion and exclusion criteria are verified. Randomisation order was determined on a central randomisation list held at site (one list per site).

Subjects were randomised to the order of the treatments and the skin TTS application sites.

There are 4 possible TTS application sites:
- Deltoid region of the non-dominant arm
- Deltoid region of the dominant arm
- Right upper back
- Left upper back.

Check-in Procedures

On each day prior to treatment (e.g. Day −1 or Day 17), subjects were checked in to the study unit. The following procedures were undertaken:
- Review of consent and eligibility
- Urine pregnancy test (Female subjects of child bearing potential only)
- Alcohol screen (by breath test) and
- Urine drug screen as per screening visit
- Naltrexone HCl dosing
- Adverse events
- Concomitant medications will be recorded.

Randomisation occurred once in the study on Day −1.

Study Procedures

The treatment phase included study periods with a single dose application. The following procedures were undertaken in each period:
- Pre-dosing biochemistry (fasting) as per screening
- TTS application
- Vital signs (supine respiration rate, supine blood pressure, supine pulse rate)
- $SpO_2$
- Blood samples for drug concentration measurements obtained pre-dose and at pre-specified times throughout the duration of the study for each subject; TTS was removed at 168 hours after TTS application; blood draw must be performed immediately prior to TTS removal
- 12-lead ECG (taken before each TTS application, at 72, 120, and 168 hours after each TTS application in each study period and at the Post-Study Medical)
- Oral temperature was recorded at specified times throughout the study
- Adverse events; recorded throughout the study on an ongoing basis whilst confined to the study unit and through open questioning. Any recorded skin reactions will also be recorded as adverse events.
- Concomitant medications; recorded at Screening and throughout the study
- TTS site skin assessment and duration and observation assessments; duration of TTS wear assessments were rated just after application and then at the same time each day of TTS wear. TTS observation assessments were performed just before TTS removal. Skin site reaction will be assessed 30 min after TTS removal.

Where more than one procedure was scheduled at the same time-point, the following order of procedures was ideally followed:
- BTDS blood sample collection within ±5 minutes of scheduled sampling time post dose. Pre-dose sample must be taken within the hour before study drug dosing
- Vital signs and ECG (within ±15 minutes of scheduled time)
- Pulse oximetry (within ±15 minutes of scheduled time)
- Skin reaction assessment at application site (within ±5 minutes of scheduled time)
- Duration of TTS wear observations (within ±30 minutes of scheduled time)
- Observation of TTS at removal (within −30 minutes of scheduled time)
- Food and fluids (start time within ±30 minutes of scheduled time).

Throughout the Study Period when subjects had the TTS applied, they were allowed to have a shower (not bath) but they had to refrain from washing, or rubbing the site of TTS application. The subjects should also refrain from showering until the day after TTS application. The TTS was removed on the eighth day of the Study Period following the blood draw at 168 hours after TTS application.

Washout Period

There was a minimum 10 day washout period between removal of one TTS and application of another.

Confinement to the Study Unit

Subjects were confined to the study unit from Check-In on the day before study drug administration until the time that the 192 hour post-TTS application procedures were completed. Subjects returned to the unit for the 216, 240, 264 and 288 hours post-study procedures and the Post-Study Medical. During confinement in the unit, subjects will receive standardised meals.

Pharmacokinetic Measurements

Blood samples for pharmacokinetic assessments were obtained for each subject at predose and at 2, 4, 8, 12, 16, 24, 36, 48, 60, 72, 84, 96, 108, 120, 144, 168, 169, 172, 176, 180, 192, 216, 240, 264 and 288 hours post-TTS application.

For each sample, 4 ml of blood were drawn into 4 ml tubes containing $K_2EDTA$ solution, an anticoagulant. Samples were centrifuged within 30 minutes of collection. Following centrifugation (1500 G, 4° C., 15 minutes), the plasma was transferred, via pipette, into 2 labelled 3 ml polypropylene tubes, and stored at −20° C. within 1 hour of collection.

Plasma concentrations of analytes were quantified by liquid chromatography-tandem mass spectrometric methodology (LC-MS/MS) using a previously validated assay.

For each subject, the following pharmacokinetic parameters were calculated based on the plasma concentrations of buprenorphine:
- AUCt (pg.hr/ml)—the area under the plasma concentration-time curve from hour 0 to the last measurable plasma concentration, calculated by the linear trapezoidal method;
- AUCINF (pg.hr/ml)—the area under the plasma concentration-time curve extrapolated to infinity, calculated using the formula $$AUCINF = AUCt + \frac{CLast}{LambdaZ},$$

where CLast is the last measurable plasma concentration and LambdaZ is the apparent terminal phase rate constant;
- Cmax (pg/ml)—the maximum observed plasma concentration;
- tmax (hr)—the time to maximum plasma concentration;
- LambdaZ (l/hr)—the apparent terminal phase rate constant, where LambdaZ is the magnitude of the slope of the linear regression of the log concentration versus time profile during the terminal phase;

t½Z (hr)—the apparent plasma terminal phase half-life (whenever possible), where t½Z=(ln 2)/LambdaZ.

Plasma concentration values below the level of quantitation were set to equal zero for the analysis.

AUC values were calculated using the linear trapezoidal method. After removal of the BTDS, where possible, LambdaZ values were estimated using those points determined to be in the terminal log-linear phase. t½Z was determined from the ratio of ln 2 to LambdaZ.

Individual Subject Stopping Criteria

Subjects who met one or more of the following stopping criteria were discontinued from the study:
  Markedly Abnormal Liver Function Tests or Creatinine test
  $O_2$ saturation 85% or less
  Increase in QTc of more than 60 msec above pre-dose values of each study period or QTc greater than 500 msec
  Serious adverse drug reaction
  Severe nausea and vomiting
  Severe reaction at TTS site or a local reaction which necessitates removal of the TTS or discontinuation of the infusion
  Systolic blood pressure (BP) ≥180 mmHg
  Heart rate (HR) ≥140 bpm
  Other BP and HR values and changes from baseline if associated with cardiovascular compromise.

Study Restrictions

As per the inclusion/exclusion criteria, subjects had to be willing to eat all the food supplied throughout the study. Menus were standardised while subjects are in the study unit. The menus were the same for each study period. However, the menus for each day needed not be identical. Subjects had to consume only the food given to them while in the unit. Food and water will be restricted as follows:
  Subjects were given an evening meal and snack following check-in to the study unit on the day before dosing to be consumed >8 hours before dosing.
  Subjects received a light breakfast 1 hour before commencement of treatment. There was free access to drinking water throughout the day, except within 30 minutes before vital sign measurements or commencement of treatment. A low fat lunch (<30% fat), dinner, and an evening snack were provided at 4, 10, and 14 hours after TTS application. Drinks of decaffeinated tea or decaffeinated coffee were supplied with meals.
  Meals were provided at the same time each day (as on Day 1). There was free access to drinking water and de-caffeinated drinks throughout the day, except within 30 minutes before vital sign measurements.
  Breakfast will be optional after all study procedures have been completed.

Subjects had to abstain from smoking within 45 days of study drug administration and during the entire study. Subjects had to abstain from alcohol from 48 hours before the first study drug administration until 72 hours after the last naltrexone dose of the last study period. Caffeine or xanthine containing food or beverages were not permitted during the study from check-in before treatment, until after the last study pharmacokinetic sample has been taken.

Follow-Up Period

Subjects that completed the treatment phase or who discontinued treatment early were followed up within 7 to 10 days after the Subject's last visit/dose of study medication.

Study Completion Procedures

Subjects that completed the Treatment Phase carried out the following Completion/Discontinuation Visit procedures:
  Subjects attended a Post-Study Medical Visit 7 to 10 days after removal of their last TTS if this was the last treatment received in the case of completion/discontinuation from the study.
  Safety was monitored and Post-Study Medical procedures were carried out including the following:
    Physical examination including weight measurement
    Haematology (as for screening visit)
    Blood chemistry (as for screening visit)
    Urinalysis (as for screening visit)
    Serum pregnancy test for females of child bearing potential
    12-lead ECG
    Vital signs (supine respiration rate, supine blood pressure, supine pulse rate)
    Pulse oximetry
    Oral temperature
    Review of adverse events
    Review of concomitant therapy.

The results of this study are shown in FIG. 5 and Tables 7.1 to 7.11 below:

TABLE 7.1

Statistical results for pharmacokinetic parameters (full analysis population): Example 1 TTS (12 mg/10 cm$^2$) and Example 2 TTS (12 mg/10 cm$^2$) relative to BuTrans® (20 mg/25 cm$^2$)

|  | Example 1 TTS | Example 2 TTS | BuTrans ® |
|---|---|---|---|
|  | Cmax (pg/ml) | | |
| n$^a$ | 26 | 28 | 28 |
| Mean$^b$ | 312.20 | 301.28 | 383.63 |
| SD$^c$ | 169.48 | 163.41 | 176.63 |
| SE$^d$ | 33.24 | 30.88 | 33.38 |
| GeoMean$^e$ | 270.93 | 261.30 | 346.47 |
| log SD$^f$ | 0.552 | 0.560 | 0.467 |
| log SE$^g$ | 0.108 | 0.106 | 0.088 |
| Min$^h$ | 92.80 | 80.80 | 120.03 |
| Median$^i$ | 260.87 | 283.00 | 376.74 |
| Max$^k$ | 708.13 | 829.94 | 872.38 |
|  | AUCt (pg · hr/ml) | | |
| n$^a$ | 26 | 28 | 28 |
| Mean$^b$ | 29682.11 | 31223.49 | 44323.44 |
| SD$^c$ | 13814.72 | 15305.33 | 19273.58 |
| SE$^d$ | 2709.29 | 2892.44 | 3642.36 |
| GeoMean$^e$ | 26904.86 | 27468.57 | 40613.23 |
| log SD$^f$ | 0.452 | 0.534 | 0.428 |
| log SE$^g$ | 0.089 | 0.101 | 0.081 |
| Min$^h$ | 12074.7 | 9263.5 | 14312.1 |
| Median$^i$ | 25820.52 | 26981.95 | 40866.71 |
| Max$^k$ | 64020.0 | 63874.7 | 100315.6 |
|  | AUCINF (pg · hr/ml) | | |
| n$^a$ | 24 | 23 | 25 |
| Mean$^b$ | 30689.03 | 33483.34 | 45108.89 |
| SD$^c$ | 14387.48 | 15193.45 | 19782.01 |
| SE$^d$ | 2936.83 | 3168.05 | 3956.40 |
| GeoMean$^e$ | 27724.63 | 30024.46 | 41273.54 |
| log SD$^f$ | 0.462 | 0.495 | 0.434 |
| log SE$^g$ | 0.094 | 0.103 | 0.087 |
| Min$^h$ | 12498.8 | 10821.7 | 14619.5 |
| Median$^i$ | 26437.33 | 32248.48 | 43282.61 |
| Max$^k$ | 64907.6 | 64670.1 | 101394.2 |
|  | tmax (hr) | | |
| n$^a$ | 26 | 28 | 28 |
| Mean$^b$ | 79.12 | 72.00 | 81.93 |
| SD$^c$ | 34.50 | 31.33 | 37.56 |
| SE$^d$ | 6.77 | 5.92 | 7.10 |
| Min$^h$ | 36.00 | 24.00 | 24.00 |

TABLE 7.1-continued

Statistical results for pharmacokinetic parameters (full analysis population): Example 1 TTS (12 mg/10 cm$^2$) and Example 2 TTS (12 mg/10 cm$^2$) relative to BuTrans ® (20 mg/25 cm$^2$)

|  | Example 1 TTS | Example 2 TTS | BuTrans ® |
|---|---|---|---|
| Median$^i$ | 78.00 | 66.00 | 72.00 |
| Max$^k$ | 172.00 | 144.00 | 169.00 |
| LambdaZ (1/hr) | | | |
| n$^a$ | 24 | 23 | 25 |
| Mean$^b$ | 0.0179 | 0.0192 | 0.0175 |
| SD$^c$ | 0.0079 | 0.0087 | 0.0068 |
| SE$^d$ | 0.0016 | 0.0018 | 0.0014 |
| Min$^h$ | 0.007 | 0.008 | 0.007 |
| Median$^i$ | 0.0165 | 0.0165 | 0.0164 |
| Max$^k$ | 0.043 | 0.044 | 0.041 |
| t½Z (hr) | | | |
| n$^a$ | 24 | 23 | 25 |
| Mean$^b$ | 44.77 | 42.75 | 44.73 |
| SD$^c$ | 16.96 | 17.66 | 16.82 |
| SE$^d$ | 3.46 | 3.68 | 3.36 |
| Min$^h$ | 15.94 | 15.92 | 16.75 |
| Median$^i$ | 41.96 | 41.92 | 42.22 |
| Max$^k$ | 93.79 | 83.91 | 98.27 |

$^a$n = number of subjects with data available (non-zero values).
$^b$Mean = arithmetic mean; the sum of all the values of observations divided by the total number of observations.
$^c$SD = standard deviation.
$^d$SE = standard error.
$^e$GeoMean = geometric mean; the mean of the log transformed data backtransformed to the original scale.
$^f$log SD = standard deviation of the log transformed data.
$^g$log SE = standard error of the log transformed data.
$^h$Min = minimum value.
$^i$Median = middle value when the list of values is ranked.
$^k$Max = maximum value.

TABLE 7.2

Statistical results for pharmacokinetic parameters (full analysis population): Comparative Example 5 TTS (6.75 mg/15 cm$^2$) relative to BuTrans ® (20 mg/25 cm$^2$)

|  | Comp. Example 5 TTS | BuTrans ® | Comp. Example 5 TTS | BuTrans ® |
|---|---|---|---|---|
| | Cmax (pg/ml) | | AUCt (pg · hr/ml) | |
| n$^a$ | 28 | 28 | 28 | 28 |
| Mean$^b$ | 288.29 | 383.63 | 27709.30 | 44323.44 |
| SD$^c$ | 137.67 | 176.63 | 13213.42 | 19273.58 |
| SE$^d$ | 26.02 | 33.38 | 2497.10 | 3642.36 |
| GeoMean$^e$ | 258.05 | 346.47 | 25025.91 | 40613.23 |
| log SD$^f$ | 0.484 | 0.467 | 0.456 | 0.428 |
| log SE$^g$ | 0.091 | 0.088 | 0.086 | 0.081 |
| Min$^h$ | 111.98 | 120.03 | 11539.6 | 14312.1 |
| Median$^i$ | 254.25 | 376.74 | 24401.87 | 40866.71 |
| Max$^k$ | 595.80 | 872.38 | 57931.7 | 100315.6 |
| | AUCINF (pg · hr/ml) | | tmax (hr) | |
| n$^a$ | 26 | 25 | 28 | 28 |
| Mean$^b$ | 28850.38 | 45108.89 | 108.21 | 81.93 |
| SD$^c$ | 13805.37 | 19782.01 | 38.02 | 37.56 |
| SE$^d$ | 2707.46 | 3956.40 | 7.19 | 7.10 |
| GeoMean$^e$ | 26019.04 | 41273.54 | NA$^l$ | NA$^l$ |
| log SD$^f$ | 0.461 | 0.434 | NA$^l$ | NA$^l$ |
| log SE$^g$ | 0.090 | 0.087 | NA$^l$ | NA$^l$ |
| Min$^h$ | 11702.00 | 14619.5 | 48.00 | 24.00 |
| Median$^i$ | 25186.06 | 43282.61 | 96.00 | 72.00 |
| Max$^k$ | 60731.70 | 101394.2 | 169.00 | 169.00 |
| | LambdaZ (1/hr) | | t½Z (hr) | |
| n$^a$ | 26 | 25 | 26 | 25 |
| Mean$^b$ | 0.0172 | 0.0175 | 50.38 | 44.73 |
| SD$^c$ | 0.0090 | 0.0068 | 27.38 | 16.82 |
| SE$^d$ | 0.0018 | 0.0014 | 5.37 | 3.36 |
| Min$^h$ | 0.004 | 0.0070 | 13.80 | 16.75 |
| Median$^i$ | 0.0157 | 0.0164 | 44.14 | 42.22 |
| Max$^k$ | 0.050 | 0.041 | 154.54 | 98.27 |

$^a$n = number of subjects with data available (non-zero values).
$^b$Mean = arithmetic mean; the sum of all the values of observations divided by the total number of observations.
$^c$SD = standard deviation.
$^d$SE = standard error.
$^e$GeoMean = geometric mean; the mean of the log transformed data backtransformed to the original scale.
$^f$log SD = standard deviation of the log transformed data.
$^g$log SE = standard error of the log transformed data.
$^h$Min = minimum value.
$^i$Median = middle value when the list of values is ranked.
$^k$Max = maximum value.
$^l$NA = not applicable.

TABLE 7.3

Mean AUCt per area of release (pg · hr/ml-cm$^2$)

| Example 1 TTS | Example 2 TTS | Comparative Example 5 TTS | BuTrans ® |
|---|---|---|---|
| 2690.49 | 2746.86 | 1668.39 | 1624.53 |

TABLE 7.4

Summary of mixed model$^a$ for pharmacokinetic parameters Cmax, AUCt, and AUCINF (full analysis population): Example 1 TTS (12 mg) relative to BuTrans ® (20 mg)

|  |  | LS Mean$^b$ | | LS Mean$^c$ | |
|---|---|---|---|---|---|
|  | n$^d$ | Example 1 TTS | BuTrans ® | Ratio Exampel 1 TTS/ BuTrans ® (%) | 90% Confidence Interval (%) |
| Cmax | 25 | 278.48 | 352.93 | 78.90$^e$ | [66.65, 93.41] |
| AUCt | 25 | 27289.42 | 42335.49 | 64.46$^f$ | [55.05, 75.45] |
| AUCINF | 20 | 26968.66 | 40541.38 | 66.52$^f$ | [58.09, 76.18] |

$^a$Data analysed using a mixed effects linear model with treatment, actual sequence and period as fixed effects and subject within sequence as random effect. The analyses only consider subjects who completed both periods of the respective treatment comparison.
$^b$Least square mean; back-transformed from log scale to linear scale.
$^c$Least square mean; back-transformed from difference on log scale to ratio on linear scale.
$^d$Number of subjects with data for both Example 1 and BuTrans ® available.
$^e$equivalent to relative Cmax ratio.
$^f$equivalent to relative bioavailability.

TABLE 7.5

Summary of mixed model[a] for pharmacokinetic parameters Cmax, AUCt, and AUCINF (full analysis population): Example 2 TTS (12 mg) relative to BuTrans ® (20 mg)

|  |  | LS Mean[b] |  | LS Mean[c] |  |
|---|---|---|---|---|---|
|  | n[d] | Example 2 TTS | BuTrans ® | Ratio Exampel 2 TTS/ BuTrans ® (%) | 90% Confidence Interval (%) |
| Cmax | 24 | 267.94 | 338.34 | 79.19[e] | [69.03, 90.86] |
| AUCt | 24 | 28021.68 | 39507.72 | 70.93[f] | [61.99, 81.15] |
| AUCINF | 16 | 31910.44 | 42095.11 | 75.81 | [62.53, 91.90] |

[a]Data analysed using a mixed effects linear model with treatment, actual sequence and period as fixed effects and subject within sequence as random effect. The analyses only consider subjects who completed both periods of the respective treatment comparison.
[b]Least square mean; back-transformed from log scale to linear scale.
[c]Least square mean; back-transformed from difference on log scale to ratio on linear scale.
[d]Number of subjects with data for both Example 2 and BuTrans ® available.
[e]equivalent to relative Cmax ratio.
[f]equivalent to relative bioavailability.

TABLE 7.6

Summary of mixed model[a] for pharmacokinetic parameters Cmax, AUCt, and AUCINF (full analysis population): Comparative Example 5 TTS (6.75 mg) relative to BuTrans ® (20 mg)

|  |  | LS Mean[b] |  | LS Mean[c] |  |
|---|---|---|---|---|---|
|  | n[d] | Comp. Example 5 TTS | BuTrans ® | Ratio Comp. Exampel 5 TTS/ BuTrans ® (%) | 90% Confidence Interval (%) |
| Cmax | 26 | 274.03 | 348.94 | 78.53[e] | [65.43, 94.26] |
| AUCt | 26 | 26037.56 | 41121.81 | 63.32[f] | [52.64, 76.16] |
| AUCINF | 21 | 26782.27 | 41460.21 | 64.60[f] | [51.62, 80.84] |

[a]Data analysed using a mixed effects linear model with treatment, actual sequence and period as fixed effects and subject within sequence as random effect. The analyses only consider subjects who completed both periods of the respective treatment comparison.
[b]Least square mean; back-transformed from log scale to linear scale.
[c]Least square mean; back-transformed from difference on log scale to ratio on linear scale.
[d]Number of subjects with data for both Comparative Example 5 TTS and BuTrans ® available.
[e]equivalent to relative Cmax ratio.
[f]equivalent to relative bioavailability.

TABLE 7.7

Summary of mixed model[a] for pharmacokinetic parameter t½Z (full analysis population): Example 1 TTS (12 mg) relative to BuTrans ® (20 mg)

|  |  | LS Mean[b] |  |  |  |
|---|---|---|---|---|---|
|  | n[c] | Example 1 | BuTrans ® | Exampel 1 - BuTrans ® | 90% Confidence Interval |
| t½Z | 20 | 42.69 | 42.62 | 0.07 | [−4.38, 4.53] |

[a]Data analysed using a mixed effects linear model with treatment, actual sequence and period as fixed effects and subject within sequence as random effect. The analyses only consider subjects who completed both periods of the respective treatment comparison.
[b]Least square mean.
[c]Number of subjects with data for both Example 1 and BuTrans ® available.

TABLE 7.8

Summary of mixed model[a] for pharmacokinetic parameter t½Z (full analysis population): Example 2 TTS (12 mg) relative to BuTrans ® (20 mg)

|  |  | LS Mean[b] |  |  |  |
|---|---|---|---|---|---|
|  | n[c] | Example 2 | BuTrans ® | Exampel 2 - BuTrans ® | 90% Confidence Interval |
| t½Z | 16 | 43.16 | 44.63 | −1.47 | [−10.63, 7.70] |

[a]Data analysed using a mixed effects linear model with treatment, actual sequence and period as fixed effects and subject within sequence as random effect. The analyses only consider subjects who completed both periods of the respective treatment comparison.
[b]Least square mean.
[c]Number of subjects with data for both Example 2 and BuTrans ® available.

TABLE 7.9

Summary of mixed model[a] for pharmacokinetic parameter t½Z (full analysis population): Comparative Example 5 TTS (6.75 mg) relative to BuTrans ® (20 mg)

|  |  | LS Mean[b] |  |  |  |
|---|---|---|---|---|---|
|  | n[c] | Comp. Example 5 TTS | BuTrans ® | Comp. Example 5 TTS - BuTrans ® | 90% Confidence Interval |
| t½Z | 21 | 52.64 | 42.59 | 10.05 | [0.32, 19.78] |

[a]Data analysed using a mixed effects linear model with treatment, actual sequence and period as fixed effects and subject within sequence as random effect. The analyses only consider subjects who completed both periods of the respective treatment comparison.
[b]Least square mean.
[c]Number of subjects with data for both Comparative Example 5 TTS and BuTrans ® available.

TABLE 7.10

Bioequivalence assessment relative to BuTrans ® for a 36% increase[a] in plasma concentrations for Example 2 TTS

|  | Ratio Exampel 2 TTS/BuTrans ® (%) | 90% Confidence Interval (%) |
|---|---|---|
| ln(Cmax) | 106.93 | [91.92; 124.41] |
| ln(AUCt) | 95.37 | [82.07; 110.82] |
| ln(AUCINF) | 100.56 | [85.63; 118.10] |

[a]Calculated based on the individual subject data of Example 2 TTS (12 mg).

An increase of about 36% in plasma concentrations for Example 2 TTS would be expected to render the TTS bioequivalent to BuTrans® (20 mg/25 cm²), also known as Norspan®, in a single dose study.

TABLE 7.11

Bioequivalence assessment relative to BuTrans ® for a 50% increase[a] in plasma concentrations for Comparative Example 5 TTS

|  | Ratio Comp. Exampel 5 TTS/BuTrans ® (%) | 90% Confidence Interval (%) |
|---|---|---|
| ln(Cmax) | 119.77 | [102.53; 139.91] |
| ln(AUCt) | 97.43 | [83.70; 113.41] |
| ln(AUCINF) | 101.14 | [85.04; 120.29] |

[a]Calculated based on the individual subject data of Comparative Example 5 TTS (6.75 mg).

Even an increase of about 50% in plasma concentrations for Comparative Example 5 TTS would not be expected to render the TTS bioequivalent to BuTrans® (20 mg/25 cm²), also known as Norspan®, in a single dose study.

The Invention Relates in Particular to the Following Further Items

1. Transdermal therapeutic system for the transdermal administration of buprenorphine, comprising a buprenorphine-containing self-adhesive layer structure comprising
   A) a buprenorphine-impermeable backing layer, and
   B) a buprenorphine-containing pressure-sensitive adhesive layer on said buprenorphine-impermeable backing layer, the adhesive layer comprising
      a) at least one polymer-based pressure-sensitive adhesive,
      b) an analgesically effective amount of buprenorphine base or a pharmaceutically acceptable salt thereof, and
      c) a carboxylic acid selected from the group consisting of oleic acid, linoleic acid, linolenic acid, levulinic acid and mixtures thereof, in an amount sufficient so that said analgesically effective amount of buprenorphine is solubilized therein to form a mixture, and the carboxylic acid buprenorphine mixture forms dispersed deposits in the said pressure-sensitive adhesive,
wherein said buprenorphine-containing pressure-sensitive adhesive layer is the skin contact layer.

2. Transdermal therapeutic system in accordance with item 1, wherein said buprenorphine is present in the form of buprenorphine base.

3. Transdermal therapeutic system in accordance with item 1, wherein said carboxylic acid is levulinic acid.

4. Transdermal therapeutic system in accordance with item 1, wherein said buprenorphine is present in the form of buprenorphine base and said carboxylic acid is levulinic acid.

5. Transdermal therapeutic system in accordance with item 1, wherein said polymer-based pressure-sensitive adhesive is based on polysiloxanes or polyisobutylenes.

6. Transdermal therapeutic system in accordance with item 1, wherein said polymer-based pressure-sensitive adhesive is based on polysiloxanes.

7. Transdermal therapeutic system in accordance with item 1, wherein said buprenorphine is present in the form of buprenorphine base, said carboxylic acid is levulinic acid and the polymer-based pressure-sensitive adhesive is based on polysiloxanes.

8. Transdermal therapeutic system in accordance with any one of items 1 to 7, the amount of said buprenorphine contained in the transdermal therapeutic system ranging from
about 1 mg to about 4 mg buprenorphine base or an equimolar amount of a pharmaceutically acceptable salt thereof, or
about 3.5 mg to about 8 mg buprenorphine base or an equimolar amount of a pharmaceutically acceptable salt thereof, or
about 6.5 mg to about 16 mg buprenorphine base or an equimolar amount of a pharmaceutically acceptable salt thereof, or
about 11.5 mg to about 24 mg buprenorphine base or an equimolar amount of a pharmaceutically acceptable salt thereof, or
about 15 mg to about 32 mg buprenorphine base or an equimolar amount of a pharmaceutically acceptable salt thereof 9. Transdermal therapeutic system in accordance with item 8, the amount of said buprenorphine contained in the transdermal therapeutic system ranging from about 1 mg to about 3.5 mg buprenorphine base or an equimolar amount of a pharmaceutically acceptable salt thereof, or
about 3.5 mg to about 7 mg buprenorphine base or an equimolar amount of a pharmaceutically acceptable salt thereof, or
about 6.5 mg to about 14 mg buprenorphine base or an equimolar amount of a pharmaceutically acceptable salt thereof, or
about 11.5 mg to about 21 mg buprenorphine base or an equimolar amount of a pharmaceutically acceptable salt thereof, or
about 15 mg to about 28 mg buprenorphine base or an equimolar amount of a pharmaceutically acceptable salt thereof 10. Transdermal therapeutic system in accordance with item 8, the amount of said buprenorphine contained in the transdermal therapeutic system ranging from
about 1 mg to about 3 mg buprenorphine base or an equimolar amount of a pharmaceutically acceptable salt thereof, or
about 3.5 mg to about 6 mg buprenorphine base or an equimolar amount of a pharmaceutically acceptable salt thereof, or
about 6.5 mg to about 11 mg buprenorphine base or an equimolar amount of a pharmaceutically acceptable salt thereof, or
about 11.5 mg to about 14 mg buprenorphine base or an equimolar amount of a pharmaceutically acceptable salt thereof, or
about 15 mg to about 24 mg buprenorphine base or an equimolar amount of a pharmaceutically acceptable salt thereof 11. Transdermal therapeutic system in accordance with any one of items 1 to 10, the size of said buprenorphine-containing pressure-sensitive adhesive layer providing the area of release ranging from
about 1 $cm^2$ to about 4.8 $cm^2$, or
about 3 $cm^2$ to about 9.5 $cm^2$,
about 6 $cm^2$ to about 19 $cm^2$,
about 12 $cm^2$ to about 28.5 $cm^2$, or
about 16 $cm^2$ to about 38 $cm^2$.

12. Transdermal therapeutic system in accordance with item 11, the size of said buprenorphine-containing pressure-sensitive adhesive layer providing the area of release ranging from
about 1 $cm^2$ to about 4.5 $cm^2$, or
about 3 $cm^2$ to about 9 $cm^2$,
about 6 $cm^2$ to about 18 $cm^2$,
about 12 $cm^2$ to about 27 $cm^2$, or
about 16 $cm^2$ to about 35 $cm^2$.

13. Transdermal therapeutic system in accordance with item 11, the size of said buprenorphine-containing pressure-sensitive adhesive layer providing the area of release ranging from
about 2.5 $cm^2$ to about 4 $cm^2$,
about 5 $cm^2$ to about 8 $cm^2$,
about 10 $cm^2$ to about 16 $cm^2$,
about 17 $cm^2$ to about 23 $cm^2$, or
about 23.5 $cm^2$ to about 32 $cm^2$.

14. Transdermal therapeutic system in accordance with any one of items 1 to 7, the size of said buprenorphine-containing pressure-sensitive adhesive layer providing the area of release ranging from about 1 $cm^2$ to about 4.8 $cm^2$ and the amount of said buprenorphine contained in the transdermal therapeutic system ranging from about 1 mg to about 4 mg buprenorphine base or an equimolar amount of a pharmaceutically acceptable salt thereof.

15. Transdermal therapeutic system in accordance with any one of items 1 to 7, the size of said buprenorphine-containing pressure-sensitive adhesive layer providing the area of release ranging from about 3 cm² to about 9.5 cm², and the amount of said buprenorphine contained in the transdermal therapeutic system ranging from
about 3.5 mg to about 8 mg buprenorphine base or an equimolar amount of a pharmaceutically acceptable salt thereof 16. Transdermal therapeutic system in accordance with any one of items 1 to 7, the size of said buprenorphine-containing pressure-sensitive adhesive layer providing the area of release ranging from about 6 cm² to about 19 cm² and the amount of said buprenorphine contained in the transdermal therapeutic system ranging from
about 6.5 mg to about 16 mg buprenorphine base or an equimolar amount of a pharmaceutically acceptable salt thereof 17. Transdermal therapeutic system in accordance with any one of items 1 to 7, the size of said buprenorphine-containing pressure-sensitive adhesive layer providing the area of release ranging from about 12 cm² to about 28.5 cm², and the amount of said buprenorphine contained in the transdermal therapeutic system ranging from
about 11.5 mg to about 24 mg buprenorphine base or an equimolar amount of a pharmaceutically acceptable salt thereof 18. Transdermal therapeutic system in accordance with any one of items 1 to 7, the size of said buprenorphine-containing pressure-sensitive adhesive layer providing the area of release ranging from about 16 cm² to about 38 cm², and the amount of said buprenorphine contained in the transdermal therapeutic system ranging from
about 15 mg to about 32 mg buprenorphine base or an equimolar amount of a pharmaceutically acceptable salt thereof 19. Transdermal therapeutic system in accordance with any one of items 1 to 7, the size of said buprenorphine-containing pressure-sensitive adhesive layer providing the area of release ranging from about 1 cm² to about 4.5 cm² and the amount of said buprenorphine contained in the transdermal therapeutic system ranging from
about 1 mg to about 3.5 mg buprenorphine base or an equimolar amount of a pharmaceutically acceptable salt thereof 20. Transdermal therapeutic system in accordance with any one of items 1 to 7, the size of said buprenorphine-containing pressure-sensitive adhesive layer providing the area of release ranging from about 3 cm² to about 9 cm², and the amount of said buprenorphine contained in the transdermal therapeutic system ranging from
about 3.5 mg to about 7 mg buprenorphine base or an equimolar amount of a pharmaceutically acceptable salt thereof 21. Transdermal therapeutic system in accordance with any one of items 1 to 7, the size of said buprenorphine-containing pressure-sensitive adhesive layer providing the area of release ranging from about 6 cm² to about 18 cm² and the amount of said buprenorphine contained in the transdermal therapeutic system ranging from
about 6.5 mg to about 14 mg buprenorphine base or an equimolar amount of a pharmaceutically acceptable salt thereof 22. Transdermal therapeutic system in accordance with any one of items 1 to 7, the size of said buprenorphine-containing pressure-sensitive adhesive layer providing the area of release ranging from about 12 cm² to about 27 cm², and the amount of said buprenorphine contained in the transdermal therapeutic system ranging from
about 11.5 mg to about 21 mg buprenorphine base or an equimolar amount of a pharmaceutically acceptable salt thereof 23. Transdermal therapeutic system in accordance with any one of items 1 to 7, the size of said buprenorphine-containing pressure-sensitive adhesive layer providing the area of release ranging from about 16 cm² to about 35 cm², and the amount of said buprenorphine contained in the transdermal therapeutic system ranging from
about 15 mg to about 28 mg buprenorphine base or an equimolar amount of a pharmaceutically acceptable salt thereof 24. Transdermal therapeutic system in accordance with any one of items 1 to 7, the size of said buprenorphine-containing pressure-sensitive adhesive layer providing the area of release ranging from about 2.5 cm² to about 4 cm² and the amount of said buprenorphine contained in the transdermal therapeutic system ranging from
about 1 mg to about 3 mg buprenorphine base or an equimolar amount of a pharmaceutically acceptable salt thereof.

25. Transdermal therapeutic system in accordance with any one of items 1 to 7, the size of said buprenorphine-containing pressure-sensitive adhesive layer providing the area of release ranging from about 5 cm² to about 8 cm², and the amount of said buprenorphine contained in the transdermal therapeutic system ranging from
about 3.5 mg to about 6 mg buprenorphine base or an equimolar amount of a pharmaceutically acceptable salt thereof 26. Transdermal therapeutic system in accordance with any one of items 1 to 7, the size of said buprenorphine-containing pressure-sensitive adhesive layer providing the area of release ranging from about 10 cm² to about 16 cm² and the amount of said buprenorphine contained in the transdermal therapeutic system ranging from
about 6.5 mg to about 11 mg buprenorphine base or an equimolar amount of a pharmaceutically acceptable salt thereof 27. Transdermal therapeutic system in accordance with any one of items 1 to 7, the size of said buprenorphine-containing pressure-sensitive adhesive layer providing the area of release ranging from about 17 cm² to about 23 cm², and the amount of said buprenorphine contained in the transdermal therapeutic system ranging from
about 11.5 mg to about 14 mg buprenorphine base or an equimolar amount of a pharmaceutically acceptable salt thereof 28. Transdermal therapeutic system in accordance with any one of items 1 to 7, the size of said buprenorphine-containing pressure-sensitive adhesive layer providing the area of release ranging from about 23.5 cm² to about 32 cm², and the amount of said buprenorphine contained in the transdermal therapeutic system ranging from
about 15 mg to about 24 mg buprenorphine base or an equimolar amount of a pharmaceutically acceptable salt thereof 29. Transdermal therapeutic system in accordance with any one of items 1 to 7, the amount of said buprenorphine contained in the transdermal therapeutic system ranging from about about 1 mg to about 4 mg buprenorphine base or an equimolar amount of a pharmaceutically acceptable salt thereof.

30. Transdermal therapeutic system in accordance with item 29, the amount of said buprenorphine contained in the transdermal therapeutic system ranging from about 1 mg to about 3.5 mg buprenorphine base or an equimolar amount of a pharmaceutically acceptable salt thereof 31. Transdermal therapeutic system in accordance with item 29, the amount of said buprenorphine contained in the transdermal therapeutic system ranging from about 1 mg to about 3 mg buprenorphine base or an equimolar amount of a pharmaceutically acceptable salt thereof 32. Transdermal therapeutic system in accordance with any one of items 29 to 31, the size of said buprenorphine-containing pressure-sensitive adhesive layer providing the area of release ranging from about 1 cm$^2$ to about 4.8 cm$^2$.

33. Transdermal therapeutic system in accordance with item 32, the size of said buprenorphine-containing pressure-sensitive adhesive layer providing the area of release ranging from about 1 cm$^2$ to about 4.5 cm$^2$.

34. Transdermal therapeutic system in accordance with item 32, the size of said buprenorphine-containing pressure-sensitive adhesive layer providing the area of release ranging from about 2.5 cm$^2$ to about 4 cm$^2$.

35. Transdermal therapeutic system in accordance with any one of items 14, 19, 24, or 29 to 34, said transdermal therapeutic system providing a mean AUCt of more than 7,000 pg.hr/ml over about 168 hours of administration after a single-dose administration to a subject population.

36. Transdermal therapeutic system in accordance with item 35, said transdermal therapeutic system providing a mean AUCt of more than 8,000 pg.hr/ml over about 168 hours of administration after a single-dose administration to a subject population.

37. Transdermal therapeutic system in accordance with item 35, said transdermal therapeutic system providing a mean AUCt of from more than 8,000 pg.hr/ml to about 16,000 pg.hr/ml over about 168 hours of administration after a single-dose administration to a subject population.

38. Transdermal therapeutic system in accordance with any one of items 14, 19, 24, or 29 to 37, wherein the transdermal therapeutic system provides a nominal mean release rate of about 5 µg/hr over about 168 hours of administration.

39. Transdermal therapeutic system in accordance with any one of items 14, 19, 24, or 29 to 37, wherein the transdermal therapeutic system provides a mean release rate ranging from about 2.5 to about 7.5 µg/hr over about 168 hours of administration.

40. Transdermal therapeutic system in accordance with any one of items 14, 19, 24, or 29 to 39, wherein buprenorphine is present in the form of buprenorphine base and wherein the transdermal therapeutic system when tested in a comparative clinical study is bioequivalent to the commercial product BuTrans® having an area of release of 6.25 cm$^2$.

41. Transdermal therapeutic system in accordance with any one of items 1 to 7, the amount of said buprenorphine contained in the transdermal therapeutic system ranging from about 3.5 mg to about 8 mg buprenorphine base or an equimolar amount of a pharmaceutically acceptable salt thereof.

42. Transdermal therapeutic system in accordance with item 41, the amount of said buprenorphine contained in the transdermal therapeutic system ranging from about 3.5 mg to about 7 mg buprenorphine base or an equimolar amount of a pharmaceutically acceptable salt thereof 43. Transdermal therapeutic system in accordance with item 41, the amount of said buprenorphine contained in the transdermal therapeutic system ranging from about 3.5 mg to about 6 mg buprenorphine base or an equimolar amount of a pharmaceutically acceptable salt thereof 44. Transdermal therapeutic system in accordance with any one of items 41 to 43, the size of said buprenorphine-containing pressure-sensitive adhesive layer providing the area of release ranging from about 3 cm$^2$ to about 9.5 cm$^2$.

45. Transdermal therapeutic system in accordance with item 44, the size of said buprenorphine-containing pressure-sensitive adhesive layer providing the area of release ranging from about 3 cm$^2$ to about 9 cm$^2$.

46. Transdermal therapeutic system in accordance with item 44, the size of said buprenorphine-containing pressure-sensitive adhesive layer providing the area of release ranging from about 5 cm$^2$ to about 8 cm$^2$.

47. Transdermal therapeutic system in accordance with any one of items 15, 20, 25, or 41 to 46, said transdermal therapeutic system providing a mean AUCt of more than 14,000 pg.hr/ml over about 168 hours of administration after a single-dose administration to a subject population.

48. Transdermal therapeutic system in accordance with item 47, said transdermal therapeutic system providing a mean AUCt of more than 16,000 pg.hr/ml over about 168 hours of administration after a single-dose administration to a subject population.

49. Transdermal therapeutic system in accordance with item 47, said transdermal therapeutic system providing a mean AUCt of from more than 16,000 pg.hr/ml to about 32,000 pg.hr/ml over about 168 hours of administration after a single-dose administration to a subject population.

50. Transdermal therapeutic system in accordance with any one of items 15, 20, 25, or 41 to 49, wherein the transdermal therapeutic system provides a nominal mean release rate of about 10 µg/hr over about 168 hours of administration.

51. Transdermal therapeutic system in accordance with any one of items 15, 20, 25, or 41 to 49, wherein the transdermal therapeutic system provides a mean release rate ranging from about 8 to about 12 µg/hr over about 168 hours of administration.

52. Transdermal therapeutic system in accordance with any one of items 15, 20, 25, or 41 to 51, wherein buprenorphine is present in the form of buprenorphine base and wherein the transdermal therapeutic system when tested in a comparative clinical study is bioequivalent to the commercial product BuTrans® having an area of release of 12.5 cm$^2$.

53. Transdermal therapeutic system in accordance with any one of items 1 to 7, the amount of said buprenorphine contained in the transdermal therapeutic system ranging from about 6.5 mg to about 16 mg buprenorphine base or an equimolar amount of a pharmaceutically acceptable salt thereof.

54. Transdermal therapeutic system in accordance with item 53, the amount of said buprenorphine contained in the transdermal therapeutic system ranging from about 6.5 mg to about 14 mg buprenorphine base or an equimolar amount of a pharmaceutically acceptable salt thereof 55. Transdermal therapeutic system in accordance with item 53, the amount of said buprenorphine contained in the transdermal therapeutic system ranging from about 6.5 mg to about 11 mg buprenorphine base or an equimolar amount of a pharmaceutically acceptable salt thereof 56. Transdermal therapeutic system in accordance with any one of items 53 to 55, the size of said buprenorphine-containing pressure-sensitive adhesive layer providing the area of release ranging from about 6 cm$^2$ to about 19 cm$^2$.

57. Transdermal therapeutic system in accordance with item 56, the size of said buprenorphine-containing pressure-sensitive adhesive layer providing the area of release ranging from about 6 cm² to about 18 cm².

58. Transdermal therapeutic system in accordance with item 56, the size of said buprenorphine-containing pressure-sensitive adhesive layer providing the area of release ranging from about 10 cm² to about 16 cm².

59. Transdermal therapeutic system in accordance with any one of items 16, 21, 26, or 53 to 58, said transdermal therapeutic system providing a mean AUCt of more than 28,000 pg.hr/ml over about 168 hours of administration after a single-dose administration to a subject population.

60. Transdermal therapeutic system in accordance with item 59, said transdermal therapeutic system providing a mean AUCt of more than 32,000 pg.hr/ml over about 168 hours of administration after a single-dose administration to a subject population.

61. Transdermal therapeutic system in accordance with item 59, said transdermal therapeutic system providing a mean AUCt of from more than 32,000 pg.hr/ml to about 64,000 pg.hr/ml over about 168 hours of administration after a single-dose administration to a subject population.

62. Transdermal therapeutic system in accordance with any one of items 16, 21, 26, or 53 to 61, wherein the transdermal therapeutic system provides a nominal mean release rate of about 20 µg/hr over about 168 hours of administration.

63. Transdermal therapeutic system in accordance with any one of items 16, 21, 26, or 53 to 61, wherein the transdermal therapeutic system provides a mean release rate ranging from about 15 to about 25 µg/hr over about 168 hours of administration.

64. Transdermal therapeutic system in accordance with any one of items 16, 21, 26, or 53 to 63, wherein buprenorphine is present in the form of buprenorphine base and wherein the transdermal therapeutic system when tested in a comparative clinical study is bioequivalent to the commercial product BuTrans® having an area of release of 25 cm².

65. Transdermal therapeutic system in accordance with any one of items 1 to 7, the amount of said buprenorphine contained in the transdermal therapeutic system ranging from about 11.5 mg to about 24 mg buprenorphine base or an equimolar amount of a pharmaceutically acceptable salt thereof.

66. Transdermal therapeutic system in accordance with item 65, the amount of said buprenorphine contained in the transdermal therapeutic system ranging from about 11.5 mg to about 21 mg buprenorphine base or an equimolar amount of a pharmaceutically acceptable salt thereof 67. Transdermal therapeutic system in accordance with item 65, the amount of said buprenorphine contained in the transdermal therapeutic system ranging from about 11.5 mg to about 14 mg buprenorphine base or an equimolar amount of a pharmaceutically acceptable salt thereof 68. Transdermal therapeutic system in accordance with any one of items 65 to 67, the size of said buprenorphine-containing pressure-sensitive adhesive layer providing the area of release ranging from about 12 cm² to about 28.5 cm².

69. Transdermal therapeutic system in accordance with item 68, the size of said buprenorphine-containing pressure-sensitive adhesive layer providing the area of release ranging from about 12 cm² to about 27 cm².

70. Transdermal therapeutic system in accordance with item 68, the size of said buprenorphine-containing pressure-sensitive adhesive layer providing the area of release ranging from about 17 cm² to about 23 cm².

71. Transdermal therapeutic system in accordance with any one of items 17, 22, 27, or 65 to 70, said transdermal therapeutic system providing a mean AUCt of more than 42,000 pg.hr/ml over about 168 hours of administration after a single-dose administration to a subject population.

72. Transdermal therapeutic system in accordance with item 71, said transdermal therapeutic system providing a mean AUCt of more than 48,000 pg.hr/ml over about 168 hours of administration after a single-dose administration to a subject population.

73. Transdermal therapeutic system in accordance with item 71, said transdermal therapeutic system providing a mean AUCt of from more than 48,000 pg.hr/ml to about 96,000 pg.hr/ml over about 168 hours of administration after a single-dose administration to a subject population.

74. Transdermal therapeutic system in accordance with any one of items 17, 22, 27, or 65 to 73, wherein the transdermal therapeutic system provides a nominal mean release rate of about 30 µg/hr over about 168 hours of administration.

75. Transdermal therapeutic system in accordance with any one of items 17, 22, 27, or 65 to 73, wherein the transdermal therapeutic system provides a mean release rate ranging from about 26 to about 35 µg/hr over about 168 hours of administration.

76. Transdermal therapeutic system in accordance with any one of items 1 to 7, the amount of said buprenorphine contained in the transdermal therapeutic system ranging from about 15 mg to about 32 mg buprenorphine base or an equimolar amount of a pharmaceutically acceptable salt thereof.

77. Transdermal therapeutic system in accordance with item 76, the amount of said buprenorphine contained in the transdermal therapeutic system ranging from about 15 mg to about 28 mg buprenorphine base or an equimolar amount of a pharmaceutically acceptable salt thereof 78. Transdermal therapeutic system in accordance with item 76, the amount of said buprenorphine contained in the transdermal therapeutic system ranging from about 15 mg to about 24 mg buprenorphine base or an equimolar amount of a pharmaceutically acceptable salt thereof 79. Transdermal therapeutic system in accordance with any one of items 76 to 78, the size of said buprenorphine-containing pressure-sensitive adhesive layer providing the area of release ranging from about 16 cm² to about 38 cm².

80. Transdermal therapeutic system in accordance with item 79, the size of said buprenorphine-containing pressure-sensitive adhesive layer providing the area of release ranging from about 16 cm² to about 35 cm².

81. Transdermal therapeutic system in accordance with item 79, the size of said buprenorphine-containing pressure-sensitive adhesive layer providing the area of release ranging from about 23.5 cm² to about 32 cm².

82. Transdermal therapeutic system in accordance with any one of items 18, 23, 28, or 76 to 81, said transdermal therapeutic system providing a mean AUCt of more than 62,000 pg.hr/ml over about 168 hours of administration after a single-dose administration to a subject population.

83. Transdermal therapeutic system in accordance with item 82, said transdermal therapeutic system providing a mean AUCt of more than 64,000 pg.hr/ml over about 168 hours of administration after a single-dose administration to a subject population.

84. Transdermal therapeutic system in accordance with item 82, said transdermal therapeutic system providing a mean AUCt of from more than 64,000 pg.hr/ml to about 128,000 pg.hr/ml over about 168 hours of administration after a single-dose administration to a subject population.

85. Transdermal therapeutic system in accordance with any one of items 18, 23, 28, or 76 to 84, wherein the transdermal therapeutic system provides a nominal mean release rate of about 40 μg/hr over about 168 hours of administration.

86. Transdermal therapeutic system in accordance with any one of items 18, 23, 28, or 76 to 84, wherein the transdermal therapeutic system provides a mean release rate ranging from about 36 to about 45 μg/hr over about 168 hours of administration.

87. Transdermal therapeutic system in accordance with any one of items 1 to 86, said transdermal therapeutic system providing an arithmetic mean tmax of from about 60 hr to about 120 hr after a single-dose administration to a subject population.

88. Transdermal therapeutic system in accordance with item 87, said transdermal therapeutic system providing an arithmetic mean tmax of from about 66 hr to less than 108 hr after a single-dose administration to a subject population.

89. Transdermal therapeutic system in accordance with item 87, said transdermal therapeutic system providing an arithmetic mean tmax of from about 72 hr to about 96 hr after a single-dose administration to a subject population.

90. Transdermal therapeutic system in accordance with any one of items 1 to 89, said transdermal therapeutic system providing a mean AUCt per area of release of more than 1,700 pg.hr/ml-cm² over about 168 hours of administration after a single-dose administration to a subject population.

91. Transdermal therapeutic system in accordance with item 90, said transdermal therapeutic system providing a mean AUCt per area of release of more than 1,900 pg.hr/ml-cm² over about 168 hours of administration after a single-dose administration to a subject population.

92. Transdermal therapeutic system in accordance with item 90, said transdermal therapeutic system providing a mean AUCt per area of release of more than 2,300 pg.hr/ml-cm² over about 168 hours of administration after a single-dose administration to a subject population.

93. Transdermal therapeutic system in accordance with any one of items 1 to 92, said buprenorphine-containing pressure-sensitive adhesive layer containing more than 0.55 mg/cm² of buprenorphine base or an equimolar amount of a pharmaceutically acceptable salt thereof 94. Transdermal therapeutic system in accordance with item 93, said buprenorphine-containing pressure-sensitive adhesive layer containing more than 0.6 mg/cm² of buprenorphine base or an equimolar amount of a pharmaceutically acceptable salt thereof.

95. Transdermal therapeutic system in accordance with item 93, said buprenorphine-containing pressure-sensitive adhesive layer containing more than 0.7 mg/cm² of buprenorphine base or an equimolar amount of a pharmaceutically acceptable salt thereof.

96. Transdermal therapeutic system in accordance with item 93, said buprenorphine-containing pressure-sensitive adhesive layer containing more than 0.8 mg/cm² of buprenorphine base or an equimolar amount of a pharmaceutically acceptable salt thereof.

97. Transdermal therapeutic system in accordance with item 93, said buprenorphine-containing pressure-sensitive adhesive layer containing more than 0.9 mg/cm² of buprenorphine base or an equimolar amount of a pharmaceutically acceptable salt thereof.

98. Transdermal therapeutic system in accordance with item 93, said buprenorphine-containing pressure-sensitive adhesive layer containing more than 1 mg/cm² of buprenorphine base or an equimolar amount of a pharmaceutically acceptable salt thereof.

99. Transdermal therapeutic system in accordance with item 93, said buprenorphine-containing pressure-sensitive adhesive layer containing more than 1.1 mg/cm² of buprenorphine base or an equimolar amount of a pharmaceutically acceptable salt thereof.

100. Transdermal therapeutic system in accordance with any one of items 1 to 92, said buprenorphine-containing pressure-sensitive adhesive layer containing from about 0.55 mg/cm² to about 2 mg/cm² or from about 0.6 mg/cm² to about 2 mg/cm² of buprenorphine base or an equimolar amount of a pharmaceutically acceptable salt thereof.

101. Transdermal therapeutic system in accordance with item 100, said buprenorphine-containing pressure-sensitive adhesive layer containing from about 0.7 mg/cm² to about 2 mg/cm² of buprenorphine base or an equimolar amount of a pharmaceutically acceptable salt thereof 102. Transdermal therapeutic system in accordance with item 100, said buprenorphine-containing pressure-sensitive adhesive layer containing from about 0.8 mg/cm² to about 2 mg/cm² of buprenorphine base or an equimolar amount of a pharmaceutically acceptable salt thereof 103. Transdermal therapeutic system in accordance with item 100, said buprenorphine-containing pressure-sensitive adhesive layer containing from about 0.9 mg/cm² to about 2 mg/cm² of buprenorphine base or an equimolar amount of a pharmaceutically acceptable salt thereof 104. Transdermal therapeutic system in accordance with item 100, said buprenorphine-containing pressure-sensitive adhesive layer containing from about 1 mg/cm² to about 2 mg/cm² of buprenorphine base or an equimolar amount of a pharmaceutically acceptable salt thereof 105. Transdermal therapeutic system in accordance with item 100, said buprenorphine-containing pressure-sensitive adhesive layer containing from about 1.1 mg/cm² to about 2 mg/cm² of buprenorphine base or an equimolar amount of a pharmaceutically acceptable salt thereof 106. Transdermal therapeutic system in accordance with any one of items 1 to 105, said buprenorphine-containing pressure-sensitive adhesive layer containing more than 5% buprenorphine base or an equimolar amount of a pharmaceutically acceptable salt thereof.

107. Transdermal therapeutic system in accordance with item 106, said buprenorphine-containing pressure-sensitive adhesive layer containing more than 6% buprenorphine base or an equimolar amount of a pharmaceutically acceptable salt thereof.

108. Transdermal therapeutic system in accordance with item 106, said buprenorphine-containing pressure-sensitive adhesive layer containing more than 7% buprenorphine base or an equimolar amount of a pharmaceutically acceptable salt thereof.

109. Transdermal therapeutic system in accordance with item 106, said buprenorphine-containing pressure-sensitive adhesive layer containing more than 8% buprenorphine base or an equimolar amount of a pharmaceutically acceptable salt thereof.

110. Transdermal therapeutic system in accordance with item 106, said buprenorphine-containing pressure-sensitive adhesive layer containing more than 9% buprenorphine base or an equimolar amount of a pharmaceutically acceptable salt thereof.

111. Transdermal therapeutic system in accordance with any one of items 1 to 105, said buprenorphine-containing pressure-sensitive adhesive layer containing from about 6% to about 20% buprenorphine base or an equimolar amount of a pharmaceutically acceptable salt thereof 112. Transdermal therapeutic system in accordance with item 111, said buprenorphine-containing pressure-sensitive adhesive layer containing from about 7% to about 20% buprenorphine base or an equimolar amount of a pharmaceutically acceptable salt thereof.

113. Transdermal therapeutic system in accordance with item 111, said buprenorphine-containing pressure-sensitive adhesive layer containing from about 8% to about 20% buprenorphine base or an equimolar amount of a pharmaceutically acceptable salt thereof.

114. Transdermal therapeutic system in accordance with item 111, said buprenorphine-containing pressure-sensitive adhesive layer containing from more than 9% to about 20% buprenorphine base or an equimolar amount of a pharmaceutically acceptable salt thereof 115. Transdermal therapeutic system in accordance with any one of items 1 to 114, the buprenorphine-containing pressure-sensitive adhesive layer being coated at a dry weight of more than 6 mg/cm$^2$.

116. Transdermal therapeutic system in accordance with item 115, the buprenorphine-containing pressure-sensitive adhesive layer being coated at a dry weight of more than 8 mg/cm$^2$.

117. Transdermal therapeutic system in accordance with item 115, the buprenorphine-containing pressure-sensitive adhesive layer being coated at a dry weight of more than 10 mg/cm$^2$.

118. Transdermal therapeutic system in accordance with any one of items 1 to 114, the buprenorphine-containing pressure-sensitive adhesive layer being coated at a dry weight ranging from 6 mg/cm$^2$ to about 14 mg/cm$^2$.

119. Transdermal therapeutic system in accordance with item 118, the buprenorphine-containing pressure-sensitive adhesive layer being coated at a dry weight ranging from 8 mg/cm$^2$ to about 14 mg/cm$^2$.

120. Transdermal therapeutic system in accordance with item 118, the buprenorphine-containing pressure-sensitive adhesive layer being coated at a dry weight ranging from 10 mg/cm$^2$ to about 13 mg/cm$^2$.

121. Transdermal therapeutic system in accordance with item 118, the buprenorphine-containing pressure-sensitive adhesive layer being coated at a dry weight ranging from 11.5 mg/cm$^2$ to about 12.5 mg/cm$^2$.

122. Transdermal therapeutic system in accordance with any one of items 1 to 121, wherein the carboxylic acid is levulinic acid, said buprenorphine-containing pressure-sensitive adhesive layer containing the same % amounts of levulinic acid and buprenorphine, based on the % amount of buprenorphine base.

123. Transdermal therapeutic system in accordance with any one of items 1 to 121, wherein the carboxylic acid is levulinic acid, said buprenorphine-containing pressure-sensitive adhesive layer containing less % amounts of levulinic acid than % amounts of buprenorphine, based on the % amount of buprenorphine base.

124. Transdermal therapeutic system in accordance with any one of items 1 to 123, wherein the carboxylic acid is levulinic acid, said buprenorphine-containing pressure-sensitive adhesive layer containing more than 5% levulinic acid.

125. Transdermal therapeutic system in accordance with item 124, said buprenorphine-containing pressure-sensitive adhesive layer containing more than 6% levulinic acid.

126. Transdermal therapeutic system in accordance with item 124, said buprenorphine-containing pressure-sensitive adhesive layer containing more than 7% levulinic acid.

127. Transdermal therapeutic system in accordance with item 124, said buprenorphine-containing pressure-sensitive adhesive layer containing more than 8% levulinic acid.

128. Transdermal therapeutic system in accordance with item 124, said buprenorphine-containing pressure-sensitive adhesive layer containing more than 9% levulinic acid.

129. Transdermal therapeutic system in accordance with any one of items 1 to 78, wherein the carboxylic acid is levulinic acid, said buprenorphine-containing pressure-sensitive adhesive layer containing from about 6% to about 20% levulinic acid.

130. Transdermal therapeutic system in accordance with item 129, said buprenorphine-containing pressure-sensitive adhesive layer containing from about 7% to about 20% levulinic acid.

131. Transdermal therapeutic system in accordance with item 129, said buprenorphine-containing pressure-sensitive adhesive layer containing from about 6% to about 9% levulinic acid.

132. Transdermal therapeutic system in accordance with item 129, said buprenorphine-containing pressure-sensitive adhesive layer containing from more than 9% to about 15% levulinic acid.

133. Transdermal therapeutic system in accordance with item 129, said buprenorphine-containing pressure-sensitive adhesive layer containing from more than 9% to about 15% buprenorphine base and form about 6% to about 9% levulinic acid.

134. Transdermal therapeutic system in accordance with item 129, said buprenorphine-containing pressure-sensitive adhesive layer containing from more than 9% to about 15% buprenorphine base and from more than 9% to about 15% levulinic acid.

135. Transdermal therapeutic system in accordance with any one of items 1 to 134, the pressure-sensitive adhesive layer being coated at a dry weight of about 12 mg/cm$^2$, and wherein said buprenorphine is present in the form of buprenorphine base and the dry pressure-sensitive adhesive layer contains about 10% buprenorphine base, and wherein the carboxylic acid is levulinic acid the dry pressure-sensitive adhesive layer contains about 7% levulinic acid.

136. Transdermal therapeutic system in accordance with any one of items 1 to 134, the pressure-sensitive adhesive layer being coated at a dry weight of about 12 mg/cm$^2$, and wherein said buprenorphine is present in the form of buprenorphine base and the dry pressure-sensitive adhesive layer contains about 10% buprenorphine base, and wherein the carboxylic acid is levulinic acid the dry pressure-sensitive adhesive layer contains about 10% levulinic acid.

137. A set of five different transdermal therapeutic systems in accordance with any one of items 1 to 136, wherein
the first transdermal therapeutic system provides a size of said buprenorphine-containing pressure-sensitive adhesive layer providing the area of release ranging from about 1.5 cm$^2$ to about 5.5 cm$^2$ and contains an amount of said buprenorphine from about 1 mg to about 4.5 mg buprenorphine base or an equimolar amount of a pharmaceutically acceptable salt thereof;
the second transdermal therapeutic system provides a size of said buprenorphine-containing pressure-sensitive adhesive layer providing the area of release ranging from about 3 cm$^2$ to about 9 cm$^2$ and contains an amount of said buprenorphine from about 4 mg to about 9 mg buprenorphine base or an equimolar amount of a pharmaceutically acceptable salt thereof; and
the third transdermal therapeutic system provides a size of said buprenorphine-containing pressure-sensitive adhesive layer providing the area of release ranging from about 6 cm² to about 14 cm² and contains an amount of said buprenorphine from about 8 mg to about 14 mg buprenorphine base or an equimolar amount of a pharmaceutically acceptable salt thereof; and the fourth transdermal therapeutic system provides a size of said buprenorphine-containing pressure-sensitive adhesive layer providing the area of release ranging from about 13 cm² to about 17 cm² and contains an amount of said buprenorphine from about 15 mg to about 20 mg buprenorphine base or an equimolar amount of a pharmaceutically acceptable salt thereof; and the fifth transdermal therapeutic system provides a size of said buprenorphine-containing pressure-sensitive adhesive layer providing the area of release ranging from about 16 cm² to about 24 cm² and contains an amount of said buprenorphine from about 20 mg to about 28 mg buprenorphine base or an equimolar amount of a pharmaceutically acceptable salt thereof 138. A set of five different transdermal therapeutic systems in accordance with any one of items 1 to 136, wherein
the first transdermal therapeutic system provides a size of said buprenorphine-containing pressure-sensitive adhesive layer providing the area of release ranging from about 2 cm² to about 4 cm² and contains an amount of said buprenorphine from about 2 mg to about 4 mg buprenorphine base or an equimolar amount of a pharmaceutically acceptable salt thereof the second transdermal therapeutic system provides a size of said buprenorphine-containing pressure-sensitive adhesive layer providing the area of release ranging from about 4.5 cm² to about 7.5 cm² and contains an amount of said buprenorphine from about 5 mg to about 8 mg buprenorphine base or an equimolar amount of a pharmaceutically acceptable salt thereof; and the third transdermal therapeutic system provides a size of said buprenorphine-containing pressure-sensitive adhesive layer providing the area of release ranging from about 8 cm² to about 12 cm² and contains an amount of said buprenorphine from about 10 mg to about 14 mg buprenorphine base or an equimolar amount of a pharmaceutically acceptable salt thereof; and the fourth transdermal therapeutic system provides a size of said buprenorphine-containing pressure-sensitive adhesive layer providing the area of release ranging from about 13 cm² to about 16 cm² and contains an amount of said buprenorphine from about 16 mg to about 19 mg buprenorphine base or an equimolar amount of a pharmaceutically acceptable salt thereof; and the fifth transdermal therapeutic system provides a size of said buprenorphine-containing pressure-sensitive adhesive layer providing the area of release ranging from about 17 cm² to about 22 cm² and contains an amount of said buprenorphine from about 21 mg to about 26 mg buprenorphine base or an equimolar amount of a pharmaceutically acceptable salt thereof 139. A set of five different transdermal therapeutic systems in accordance with any one of items 1 to 136, wherein
the first transdermal therapeutic system provides a size of said buprenorphine-containing pressure-sensitive adhesive layer providing the area of release ranging from about 2 cm² to about 3 cm² and contains an amount of said buprenorphine from about 2.5 mg to about 4 mg buprenorphine base or an equimolar amount of a pharmaceutically acceptable salt thereof;

the second transdermal therapeutic system provides a size of said buprenorphine-containing pressure-sensitive adhesive layer providing the area of release ranging from about 4.5 cm² to about 6 cm² and contains an amount of said buprenorphine from about 5 mg to about 7 mg buprenorphine base or an equimolar amount of a pharmaceutically acceptable salt thereof; and the third transdermal therapeutic system provides a size of said buprenorphine-containing pressure-sensitive adhesive layer providing the area of release ranging from about 9 cm² to about 11 cm² and contains an amount of said buprenorphine from about 11 mg to about 13 mg buprenorphine base or an equimolar amount of a pharmaceutically acceptable salt thereof; and the fourth transdermal therapeutic system provides a size of said buprenorphine-containing pressure-sensitive adhesive layer providing the area of release ranging from about 14 cm² to about 16 cm² and contains an amount of said buprenorphine from about 17 mg to about 19 mg buprenorphine base or an equimolar amount of a pharmaceutically acceptable salt thereof; and the fifth transdermal therapeutic system provides a size of said buprenorphine-containing pressure-sensitive adhesive layer providing the area of release ranging from about 18 cm² to about 21 cm² and contains an amount of said buprenorphine from about 22 mg to about 25 mg buprenorphine base or an equimolar amount of a pharmaceutically acceptable salt thereof 140. Transdermal therapeutic system in accordance with any one of items 1 to 139, said buprenorphine-containing self-adhesive layer structure being attached to a second larger active agent-free self-adhesive layer structure for enhancing the adhesive properties of the overall transdermal therapeutic system.

141. Transdermal therapeutic system in accordance with item 140, said second active-free self-adhesive layer structure comprising a backing layer and an active agent-free pressure-sensitive adhesive layer of pressure-sensitive adhesive based on polyacrylates.

142. Transdermal therapeutic system in accordance with item 140, said second active-free self-adhesive layer structure comprising a backing layer and an active agent-free pressure-sensitive adhesive layer of pressure-sensitive adhesive based on polysiloxane.

143. Transdermal therapeutic system in accordance with any one of items 1 to 140, said polymer-based pressure-sensitive adhesive is based on polysiloxane in the buprenorphine-containing pressure-sensitive adhesive layer and/or in the active agent-free pressure-sensitive adhesive layer being amine-resistant.

144. Transdermal therapeutic system in accordance with any one of items 1 to 143, wherein the polymer-based pressure-sensitive adhesive is based on polysiloxane and the polysiloxane is amine-resistant being a product of the condensation reaction of silanol endblocked polydimethylsiloxane with a silica resin and the residual silanol functionality being capped with trimethylsiloxy groups.

145. Transdermal therapeutic system in accordance with anyone of items 1 to 144, wherein the polymer-based pressure-sensitive adhesive is based on polysiloxane and wherein for the production of the buprenorphine-containing and the active agent-free pressure-sensitive adhesive layer an adhesive composition of the pressure-sensitive adhesive based on polysiloxane in heptane is used.

146. Transdermal therapeutic system in accordance with any one of items 1 to 145, wherein the polymer-based pressure-sensitive adhesive is based on polysiloxane and is characterized by a solution viscosity at 25° C. and 60% solids content in heptane of more than about 150 mPa s.

147. Transdermal therapeutic system in accordance with item 146, the polymer-based pressure-sensitive adhesive is based on polysiloxane and is characterized by a solution viscosity at 25° C. 60% solids content in heptane of from about 200 mPa s to about 700 mPa s.

148. Transdermal therapeutic system in accordance with item 146, the polymer-based pressure-sensitive adhesive is based on polysiloxane and is characterized by a solution viscosity at 25° C. and 60% solids content in heptane of from about 350 mPa s to about 600 mPa s.

149. Transdermal therapeutic system in accordance with item 146, wherein the polymer-based pressure-sensitive adhesive is based on polysiloxane and is characterized by a solution viscosity at 25° C. and 60% solids content in heptane of from 480 mPa s to about 550 mPa s or alternatively from about 400 to less than 480 mPa s.

150. Transdermal therapeutic system in accordance items 146, wherein the polymer-based pressure-sensitive adhesive is based on polysiloxane is characterized by a solution viscosity at 25° C. and 60% solids content in heptane of about 500 mPa s or alternatively of about 450 mPa s.

151. Transdermal therapeutic system in accordance with any one of items 1 to 150, the polymer-based pressure-sensitive adhesive in the buprenorphine-containing layer and in the active agent-free layer being an amine-resistant pressure-sensitive adhesive based on polysiloxane and the polysiloxane being a product of the condensation reaction of silanol endblocked polydimethylsiloxane with a silica resin and the residual silanol functionality being capped with trimethylsiloxy groups and characterized by a solution viscosity at 25° C. and 60% solids content in heptane of more than 400 mPa s, and the buprenorphine-containing pressure-sensitive adhesive layer being coated at a coating dry weight of about 12 mg/cm$^2$ and containing about 10% buprenorphine base and about 10% levulinic acid.

152. Transdermal therapeutic system in accordance with any one of items 1 to 151, wherein buprenorphine is present in the form of buprenorphine base and providing a mean cumulative skin permeation rate measured in a Franz diffusion cell with dermatomed human skin of more than 1.3 μg/cm$^2$-hr over a 168 hours test.

153. Transdermal therapeutic system in accordance with item 152, providing a mean cumulative skin permeation rate measured in a Franz diffusion cell with dermatomed human skin of more than 1.5 μg/cm$^2$-hr over a 168 hours test.

154. Transdermal therapeutic system in accordance with item 152, providing a mean cumulative skin permeation rate measured in a Franz diffusion cell with dermatomed human skin of more than 1.7 μg/cm$^2$-hr over a 168 hours test.

155. Transdermal therapeutic system in accordance with item 152, providing a mean cumulative skin permeation rate measured in a Franz diffusion cell with dermatomed human skin of more than 2 μg/cm$^2$-hr over a 168 hours test.

156. Transdermal therapeutic system in accordance with item 152, providing a mean cumulative skin permeation rate measured in a Franz diffusion cell with dermatomed human skin of more than 2.5 μg/cm$^2$-hr over a 168 hours test.

157. Transdermal therapeutic system in accordance with item 152, providing a mean cumulative skin permeation rate measured in a Franz diffusion cell with dermatomed human skin of more than 3 μg/cm$^2$-hr over a 168 hours test.

158. Transdermal therapeutic system in accordance with any one of items 1 to 151, wherein buprenorphine is present in the form of buprenorphine base and providing a mean cumulative skin permeation rate measured in a Franz diffusion cell with dermatomed human skin from about 1.3 μg/cm$^2$-hr to about 4 μg/cm$^2$-hr over a 168 hours test.

159. Transdermal therapeutic system in accordance with item 158, providing a mean cumulative skin permeation rate measured in a Franz diffusion cell with dermatomed human skin from about 1.7 μg/cm$^2$-hr to about 4 μg/cm$^2$-hr over a 168 hours test.

160. Transdermal therapeutic system in accordance with item 158, providing a mean cumulative skin permeation rate measured in a Franz diffusion cell with dermatomed human skin from about 2 μg/cm$^2$-hr to about 4 μg/cm$^2$-hr over a 168 hours test.

161. Transdermal therapeutic system in accordance with item 158, providing a mean cumulative skin permeation rate measured in a Franz diffusion cell with dermatomed human skin from about 2.5 μg/cm$^2$-hr to about 4 μg/cm$^2$-hr over a 168 hours test.

162. Transdermal therapeutic system in accordance with item 158, providing a mean cumulative skin permeation rate measured in a Franz diffusion cell with dermatomed human skin from about 3 μg/cm$^2$-hr to about 4 μg/cm$^2$-hr over a 168 hours test.

163. Transdermal therapeutic system in accordance with any one of items 1 to 162, wherein buprenorphine is present in the form of buprenorphine base and providing a cumulative release of buprenorphine base as measured in a Franz diffusion cell with dermatomed human skin of 220 μg/cm$^2$ to 640 μg/cm$^2$ over a time period of 168 hours.

164. Transdermal therapeutic system in accordance with item 163, providing a cumulative release of buprenorphine base as measured in a Franz diffusion cell with dermatomed human skin of 390 μg/cm$^2$ to 640 μg/cm$^2$ over a time period of 168 hours.

165. Transdermal therapeutic system in accordance with item 163, providing a cumulative release of buprenorphine base as measured in a Franz diffusion cell with dermatomed human skin of about 400 μg/cm$^2$ to about 640 μg/cm$^2$ over a time period of 168 hours.

166. Transdermal therapeutic system in accordance with item 163, providing a cumulative release of buprenorphine base as measured in a Franz diffusion cell with dermatomed human skin of about 450 μg/cm$^2$ to about 640 μg/cm$^2$ over a time period of 168 hours.

167. Transdermal therapeutic system in accordance with item 163, providing a cumulative release of buprenorphine base as measured in a Franz diffusion cell with dermatomed human skin of about 500 μg/cm$^2$ to about 640 μg/cm$^2$ over a time period of 168 hours.

168. Transdermal therapeutic system in accordance with item 163, providing a cumulative release of buprenorphine base as measured in a Franz diffusion cell with dermatomed human skin of about 600 μg/cm$^2$ to about 640 μg/cm$^2$ over a time period of 168 hours.

169. Transdermal therapeutic system in accordance with any one of items 1 to 168, wherein buprenorphine is present in the form of buprenorphine base and providing a non-cumulative release of buprenorphine base as measured in a Franz diffusion cell with dermatomed human skin of
2 μg/cm$^2$ to 10 μg/cm$^2$ in the first 8 hours,
20 μg/cm$^2$ to 80 μg/cm$^2$ from hour 8 to hour 24,
20 μg/cm$^2$ to 80 μg/cm$^2$ from hour 24 to hour 32,
30 μg/cm$^2$ to 120 μg/cm$^2$ from hour 32 to hour 48,
40 μg/cm$^2$ to 150 μg/cm$^2$ from hour 48 to hour 72,
100 μg/cm$^2$ to 300 μg/cm$^2$ from hour 72 to hour 144, and
30 μg/cm$^2$ to 100 μg/cm$^2$ from hour 144 to hour 168.

170. Transdermal therapeutic system in accordance with item 169, wherein buprenorphine is present in the form of buprenorphine base and providing a non-cumulative release of buprenorphine base as measured in a Franz diffusion cell with dermatomed human skin of 2 μg/cm² to 6 μg/cm² in the first 8 hours,
25 μg/cm² to 60 μg/cm² from hour 8 to hour 24,
25 μg/cm² to 60 μg/cm² from hour 24 to hour 32,
40 μg/cm² to 100 μg/cm² from hour 32 to hour 48,
50 μg/cm² to 140 μg/cm² from hour 48 to hour 72,
100 μg/cm² to 280 μg/cm² from hour 72 to hour 144, and
30 μg/cm² to 100 μg/cm² from hour 144 to hour 168.

171. Transdermal therapeutic system in accordance with item 169, wherein buprenorphine is present in the form of buprenorphine base and providing a non-cumulative release of buprenorphine base as measured in a Franz diffusion cell with dermatomed human skin of 3 μg/cm² to 6 μg/cm² in the first 8 hours,
30 μg/cm² to 50 μg/cm² from hour 8 to hour 24,
30 μg/cm² to 50 μg/cm² from hour 24 to hour 32,
60 μg/cm² to 90 μg/cm² from hour 32 to hour 48,
100 μg/cm² to 130 μg/cm² from hour 48 to hour 72,
200 μg/cm² to 280 μg/cm² from hour 72 to hour 144, and
60 μg/cm² to 100 μg/cm² from hour 144 to hour 168.

172. A set of two to five different transdermal therapeutic systems each in accordance with any one of items 1 to 171, wherein the first transdermal therapeutic system provides a size of said buprenorphine-containing pressure-sensitive adhesive layer providing the area of release ranging from about 1 cm² to about 4.8 cm² and contains an amount of said buprenorphine from about 1 mg to about 4 mg buprenorphine base or an equimolar amount of a pharmaceutically acceptable salt thereof;

the second transdermal therapeutic system provides a size of said buprenorphine-containing pressure-sensitive adhesive layer providing the area of release ranging from about 3 cm² to about 9.5 cm² and contains an amount of said buprenorphine from about 3.5 mg to about 8 mg buprenorphine base or an equimolar amount of a pharmaceutically acceptable salt thereof; and the third transdermal therapeutic system provides a size of said buprenorphine-containing pressure-sensitive adhesive layer providing the area of release ranging from about 6 cm² to about 19 cm² and contains an amount of said buprenorphine from about 6.5 mg to about 16 mg buprenorphine base or an equimolar amount of a pharmaceutically acceptable salt thereof; and the fourth transdermal therapeutic system provides a size of said buprenorphine-containing pressure-sensitive adhesive layer providing the area of release ranging from about 12 cm² to about 28.5 cm² and contains an amount of said buprenorphine from about 11.5 mg to about 24 mg buprenorphine base or an equimolar amount of a pharmaceutically acceptable salt thereof; and the fifth transdermal therapeutic system provides a size of said buprenorphine-containing pressure-sensitive adhesive layer providing the area of release ranging from about 16 cm² to about 38 cm² and contains an amount of said buprenorphine from about 15 mg to about 32 mg buprenorphine base or an equimolar amount of a pharmaceutically acceptable salt thereof 173. A set of two to five different transdermal therapeutic systems each in accordance with any one of items 1 to 171, wherein the first transdermal therapeutic system provides a size of said buprenorphine-containing pressure-sensitive adhesive layer providing the area of release ranging from about 1 cm² to about 4.5 cm² and contains an amount of said buprenorphine from about 1 mg to about 3.5 mg buprenorphine base or an equimolar amount of a pharmaceutically acceptable salt thereof;

the second transdermal therapeutic system provides a size of said buprenorphine-containing pressure-sensitive adhesive layer providing the area of release ranging from about 3 cm² to about 9 cm² and contains an amount of said buprenorphine from about 3.5 mg to about 7 mg buprenorphine base or an equimolar amount of a pharmaceutically acceptable salt thereof; and the third transdermal therapeutic system provides a size of said buprenorphine-containing pressure-sensitive adhesive layer providing the area of release ranging from about 6 cm² to about 18 cm² and contains an amount of said buprenorphine from about 6.5 mg to about 14 mg buprenorphine base or an equimolar amount of a pharmaceutically acceptable salt thereof; and the fourth transdermal therapeutic system provides a size of said buprenorphine-containing pressure-sensitive adhesive layer providing the area of release ranging from about 12 cm² to about 27 cm² and contains an amount of said buprenorphine from about 11.5 mg to about 21 mg buprenorphine base or an equimolar amount of a pharmaceutically acceptable salt thereof; and the fifth transdermal therapeutic system provides a size of said buprenorphine-containing pressure-sensitive adhesive layer providing the area of release ranging from about 16 cm² to about 35 cm² and contains an amount of said buprenorphine from about 15 mg to about 28 mg buprenorphine base or an equimolar amount of a pharmaceutically acceptable salt thereof 174. A set of two to five different transdermal therapeutic systems each in accordance with any one of items 1 to 171, wherein the first transdermal therapeutic system provides a size of said buprenorphine-containing pressure-sensitive adhesive layer providing the area of release ranging from about 2.5 cm² to about 4 cm² and contains an amount of said buprenorphine from about 1 mg to about 3 mg buprenorphine base or an equimolar amount of a pharmaceutically acceptable salt thereof;

the second transdermal therapeutic system provides a size of said buprenorphine-containing pressure-sensitive adhesive layer providing the area of release ranging from about 5 cm² to about 8 cm² and contains an amount of said buprenorphine from about 3.5 mg to about 6 mg buprenorphine base or an equimolar amount of a pharmaceutically acceptable salt thereof; and the third transdermal therapeutic system provides a size of said buprenorphine-containing pressure-sensitive adhesive layer providing the area of release ranging from about 10 cm² to about 16 cm² and contains an amount of said buprenorphine from about 6.5 mg to about 11 mg buprenorphine base or an equimolar amount of a pharmaceutically acceptable salt thereof; and the fourth transdermal therapeutic system provides a size of said buprenorphine-containing pressure-sensitive adhesive layer providing the area of release ranging from about 17 cm² to about 23 cm² and contains an amount of said buprenorphine from about 11.5 mg to about 14 mg buprenorphine base or an equimolar amount of a pharmaceutically acceptable salt thereof; and the fifth transdermal therapeutic system provides a size of said buprenorphine-containing pressure-sensitive adhesive layer providing the area of release ranging from about 23.5 cm² to about 32 cm² and contains an amount of said buprenorphine from about 15 mg to about 24 mg buprenorphine base or an equimolar amount of a pharmaceutically acceptable salt thereof 175. Transdermal therapeutic system selected from a set in accordance with any one of items 172 to 174, wherein buprenorphine is present in the form of buprenorphine base and wherein the first transdermal therapeutic system when tested in a comparative clinical study is bioequivalent to a reference product having an area of release of about 6.25 cm$^2$ and providing a nominal mean release rate of about 5 μg/hr over about 168 hours of administration, the second transdermal therapeutic system when tested in a comparative clinical study is bioequivalent to a reference product having an area of release of about 12.5 cm$^2$ and providing a nominal mean release rate of about 10 μg/hr over about 168 hours of administration, the third transdermal therapeutic system when tested in a comparative clinical study is bioequivalent to a reference product having an area of release of about 25 cm$^2$ and providing a nominal mean release rate of about 20 μg/hr over about 168 hours of administration, the fourth transdermal therapeutic system when tested in a comparative clinical study is bioequivalent to a reference product having an area of release of about 37.5 cm$^2$ and providing a nominal mean release rate of about 30 μg/hr over about 168 hours of administration, the fifth transdermal therapeutic system when tested in a comparative clinical study is bioequivalent to a reference product having an area of release of about 50 cm$^2$ and providing a nominal mean release rate of about 40 μg/hr over about 168 hours of administration, wherein the reference product is prepared by the following steps:
1. homogenizing of 1,139 g of a 47.83% polyacrylate solution of a self-crosslinked acrylate copolymer of 2-ethylhexyl acrylate, vinyl acetate, acrylic acid (solvent: ethyl acetate:heptanes:isopropanol:toluene:acetylacetonate in the ratio of 37:26:26:4:1), 100 g of levulinic acid, 150 g of oleyl oleate, 100 g of polyvinylpyrrolidone, 150 g of ethanol, 200 g of ethyl acetate, and 100 g of buprenorphine base to provide a mixture;
2. stirring the mixture of step 1 for about 2 hours and controlling the dissolution of all solids visually whereas controlling the evaporation loss by reweighing and replenishing the possible solvent loss by ethyl acetate;
3. subsequently applying the mixture on a transparent polyester film in such a manner that the mass per unit area of the dry adhesive layer amounts to about 80 g/m$^2$ wherein the polyester film is rendered removable by means of siliconization and serves as protective layer;
4. removing the solvents of the mixture applied on a transparent polyester film in step 3 by drying with heated air which is led over a moist lane resulting in evaporation of the solvents, but also in melting of the levulinic acid and covering the adhesive film with a polyester foil;
5. punching the area of release of 6.25 cm$^2$, 12.5 cm$^2$, 25 cm$^2$, 37.5 cm$^2$ and 50 cm$^2$, respectively, by means of suitable cutting tools and removing the edges left between the individual systems.

176. Transdermal therapeutic system comprising buprenorphine for the transdermal administration of buprenorphine selected from:

a first transdermal therapeutic system providing a size of the area of release ranging from about 1 cm$^2$ to about 4.8 cm$^2$ and containing an amount of said buprenorphine from 1 mg to about 4 mg buprenorphine base or an equimolar amount of a pharmaceutically acceptable salt thereof and providing a mean AUCt of more than 7,000 pg.hr/ml over about 168 hours of administration after a single-dose administration to a subject population;

a second transdermal therapeutic system providing a size of the area of release ranging from about 3 cm$^2$ to about 9.5 cm$^2$ and containing an amount of said buprenorphine from about 3.5 mg to about 8 mg buprenorphine base or an equimolar amount of a pharmaceutically acceptable salt thereof and providing a mean AUCt of more than 14,000 pg.hr/ml over about 168 hours of administration after a single-dose administration to a subject population; and a third transdermal therapeutic system providing a size of the area of release ranging from about 6 cm$^2$ to about 19 cm$^2$ and containing an amount of said buprenorphine from about 6.5 mg to about 16 mg buprenorphine base or an equimolar amount of a pharmaceutically acceptable salt thereof and providing a mean AUCt of more than 28,000 pg.hr/ml over about 168 hours of administration after a single-dose administration to a subject population; and a fourth transdermal therapeutic system providing a size of the area of release ranging from about 12 cm$^2$ to about 28.5 cm$^2$ and containing an amount of said buprenorphine from about 11.5 mg to about 24 mg buprenorphine base or an equimolar amount of a pharmaceutically acceptable salt thereof and providing a mean AUCt of more than 42,000 pg.hr/ml over about 168 hours of administration after a single-dose administration to a subject population; and a fifth transdermal therapeutic system providing a size of the area of release ranging from about 16 cm$^2$ to about 38 cm$^2$ and containing an amount of said buprenorphine from about 15 mg to about 32 mg buprenorphine base or an equimolar amount of a pharmaceutically acceptable salt thereof and providing a mean AUCt of more than 62,000 pg.hr/ml over about 168 hours of administration after a single-dose administration to a subject population.

177. Transdermal therapeutic system in accordance with item 176, wherein the first transdermal therapeutic system contains an amount of said buprenorphine ranging from about 1 mg to about 3.5 mg buprenorphine base or an equimolar amount of a pharmaceutically acceptable salt thereof and provides a size of the area of release ranging from about 1 cm$^2$ to about 4.5 cm$^2$; and the second transdermal therapeutic system contains an amount of said buprenorphine ranging from about 3.5 mg to about 7 mg buprenorphine base or an equimolar amount of a pharmaceutically acceptable salt thereof and provides a size of the area of release ranging from about 3 cm$^2$ to about 9 cm$^2$; and the third transdermal therapeutic system contains an amount of said buprenorphine ranging from about 6.5 mg to about 14 mg buprenorphine base or an equimolar amount of a pharmaceutically acceptable salt thereof and provides a size of the area of release ranging from about 6 cm$^2$ to about 18 cm$^2$; and the fourth transdermal therapeutic system contains an amount of said buprenorphine ranging from about 11.5 mg to about 21 mg buprenorphine base or an equimolar amount of a pharmaceutically acceptable salt thereof and provides a size of the area of release ranging about 12 cm$^2$ to about 27 cm$^2$; and the fifth transdermal therapeutic system contains an amount of said buprenorphine ranging from about 15 mg to about 28 mg buprenorphine base or an equimolar amount of a pharmaceutically acceptable salt thereof and provides a size of the area of release ranging from about 16 cm² to about 35 cm².

178. Transdermal therapeutic system in accordance with item 176, wherein
the first transdermal therapeutic system contains an amount of said buprenorphine ranging from about 1 mg to about 3 mg buprenorphine base or an equimolar amount of a pharmaceutically acceptable salt thereof and provides a size of the area of release ranging from about 2.5 cm² to about 4 cm²; and
the second transdermal therapeutic system contains an amount of said buprenorphine ranging from about 3.5 mg to about 6 mg buprenorphine base or an equimolar amount of a pharmaceutically acceptable salt thereof and provides a size of the area of release ranging from about 5 cm² to about 8 cm²; and
the third transdermal therapeutic system contains an amount of said buprenorphine ranging from about 6.5 mg to about 11 mg buprenorphine base or an equimolar amount of a pharmaceutically acceptable salt thereof and provides a size of the area of release ranging from about 10 cm² to about 16 cm²; and
the fourth transdermal therapeutic system contains an amount of said buprenorphine ranging from about 11.5 mg to about 14 mg buprenorphine base or an equimolar amount of a pharmaceutically acceptable salt thereof and provides a size of the area of release ranging about 17 cm² to about 23 cm²; and
the fifth transdermal therapeutic system contains an amount of said buprenorphine ranging from about 15 mg to about 24 mg buprenorphine base or an equimolar amount of a pharmaceutically acceptable salt thereof and provides a size of the area of release ranging from about 23.5 cm² to about 32 cm².

179. Transdermal therapeutic system in accordance with any one of items 176 to 178, wherein
the first transdermal therapeutic system provides a mean AUCt of more than 8,000 pg.hr/ml over about 168 hours of administration after a single-dose administration to a subject population; and
the second transdermal therapeutic system provides a mean AUCt of more than 16,000 pg.hr/ml over about 168 hours of administration after a single-dose administration to a subject population; and
the third transdermal therapeutic system provides a mean AUCt of more than 32,000 pg.hr/ml over about 168 hours of administration after a single-dose administration to a subject population; and
the fourth transdermal therapeutic system provides a mean AUCt of more than 48,000 pg.hr/ml over about 168 hours of administration after a single-dose administration to a subject population; and
the fifth transdermal therapeutic system provides a mean AUCt of more than 64,000 pg.hr/ml over about 168 hours of administration after a single-dose administration to a subject population.

180. Transdermal therapeutic system comprising buprenorphine for the transdermal administration of buprenorphine selected from:
a first transdermal therapeutic system providing a size of the area of release ranging from about 1 cm² to about 4.8 cm² and containing an amount of said buprenorphine from 1 mg to about 4 mg buprenorphine base or an equimolar amount of a pharmaceutically acceptable salt thereof and providing a nominal mean release rate of about 5 µg/hr over about 168 hours of administration;

a second transdermal therapeutic system providing a size of the area of release ranging from about 3 cm² to about 9.5 cm² and containing an amount of said buprenorphine from about 3.5 mg to about 8 mg buprenorphine base or an equimolar amount of a pharmaceutically acceptable salt thereof and providing a nominal mean release rate of about 10 µg/hr over about 168 hours of administration; and
a third transdermal therapeutic system providing a size of the area of release ranging from about 6 cm² to about 19 cm² and containing an amount of said buprenorphine from about 6.5 mg to about 16 mg buprenorphine base or an equimolar amount of a pharmaceutically acceptable salt thereof and providing a nominal mean release rate of about 20 µg/hr over about 168 hours of administration; and
a fourth transdermal therapeutic system providing a size of the area of release ranging from about 12 cm² to about 28.5 cm² and containing an amount of said buprenorphine from about 11.5 mg to about 24 mg buprenorphine base or an equimolar amount of a pharmaceutically acceptable salt thereof and providing a nominal mean release rate of about 30 µg/hr over about 168 hours of administration; and
a fifth transdermal therapeutic system providing a size of the area of release ranging from about 16 cm² to about 38 cm² and containing an amount of said buprenorphine from about 15 mg to about 32 mg buprenorphine base or an equimolar amount of a pharmaceutically acceptable salt thereof and providing a nominal mean release rate of about 40 µg/hr over about 168 hours of administration.

181. Transdermal therapeutic system in accordance with item 180, wherein
the first transdermal therapeutic system contains an amount of said buprenorphine ranging from about 1 mg to about 3.5 mg buprenorphine base or an equimolar amount of a pharmaceutically acceptable salt thereof and provides a size of the area of release ranging from about 1 cm² to about 4.5 cm²; and
the second transdermal therapeutic system contains an amount of said buprenorphine ranging from about 3.5 mg to about 7 mg buprenorphine base or an equimolar amount of a pharmaceutically acceptable salt thereof and provides a size of the area of release ranging from about 3 cm² to about 9 cm²; and
the third transdermal therapeutic system contains an amount of said buprenorphine ranging from about 6.5 mg to about 14 mg buprenorphine base or an equimolar amount of a pharmaceutically acceptable salt thereof and provides a size of the area of release ranging from about 6 cm² to about 18 cm²; and
the fourth transdermal therapeutic system contains an amount of said buprenorphine ranging from about 11.5 mg to about 21 mg buprenorphine base or an equimolar amount of a pharmaceutically acceptable salt thereof and provides a size of the area of release ranging about 12 cm² to about 27 cm²; and
the fifth transdermal therapeutic system contains an amount of said buprenorphine ranging from about 15 mg to about 28 mg buprenorphine base or an equimolar amount of a pharmaceutically acceptable salt thereof and provides a size of the area of release ranging from about 16 cm² to about 35 cm².

182. Transdermal therapeutic system in accordance with item 180, wherein
the first transdermal therapeutic system contains an amount of said buprenorphine ranging from about 1 mg to about 3 mg buprenorphine base or an equimolar amount of a pharmaceutically acceptable salt thereof and provides a size of the area of release ranging from about 2.5 cm² to about 4 cm²; and the second transdermal therapeutic system contains an amount of said buprenorphine ranging from about 3.5 mg to about 6 mg buprenorphine base or an equimolar amount of a pharmaceutically acceptable salt thereof and provides a size of the area of release ranging from about 5 cm² to about 8 cm²; and the third transdermal therapeutic system contains an amount of said buprenorphine ranging from about 6.5 mg to about 11 mg buprenorphine base or an equimolar amount of a pharmaceutically acceptable salt thereof and provides a size of the area of release ranging from about 10 cm² to about 16 cm²; and the fourth transdermal therapeutic system contains an amount of said buprenorphine ranging from about 11.5 mg to about 14 mg buprenorphine base or an equimolar amount of a pharmaceutically acceptable salt thereof and provides a size of the area of release ranging about 17 cm² to about 23 cm²; and the fifth transdermal therapeutic system contains an amount of said buprenorphine ranging from about 15 mg to about 24 mg buprenorphine base or an equimolar amount of a pharmaceutically acceptable salt thereof and provides a size of the area of release ranging from about 23.5 cm² to about 32 cm².

183. Transdermal therapeutic system in accordance with any one of items 176 to 182, wherein buprenorphine is present in the form of buprenorphine base and providing a non-cumulative release of buprenorphine base as measured in a Franz diffusion cell with dermatomed human skin of 2 μg/cm² to 10 μg/cm² in the first 8 hours,
20 μg/cm² to 80 μg/cm² from hour 8 to hour 24,
20 μg/cm² to 80 μg/cm² from hour 24 to hour 32,
30 μg/cm² to 120 μg/cm² from hour 32 to hour 48,
40 μg/cm² to 150 μg/cm² from hour 48 to hour 72,
100 μg/cm² to 300 μg/cm² from hour 72 to hour 144, and
30 μg/cm² to 100 μg/cm² from hour 144 to hour 168.

184. Transdermal therapeutic system in accordance with item 183, wherein buprenorphine is present in the form of buprenorphine base and providing a non-cumulative release of buprenorphine base as measured in a Franz diffusion cell with dermatomed human skin of 2 μg/cm² to 6 μg/cm² in the first 8 hours,
25 μg/cm² to 60 μg/cm² from hour 8 to hour 24,
25 μg/cm² to 60 μg/cm² from hour 24 to hour 32,
40 μg/cm² to 100 μg/cm² from hour 32 to hour 48,
50 μg/cm² to 140 μg/cm² from hour 48 to hour 72,
100 μg/cm² to 280 μg/cm² from hour 72 to hour 144, and
30 μg/cm² to 100 μg/cm² from hour 144 to hour 168.

185. Transdermal therapeutic system in accordance with item 183, wherein buprenorphine is present in the form of buprenorphine base and providing a non-cumulative release of buprenorphine base as measured in a Franz diffusion cell with dermatomed human skin of 3 μg/cm² to 6 μg/cm² in the first 8 hours,
30 μg/cm² to 50 μg/cm² from hour 8 to hour 24,
30 μg/cm² to 50 μg/cm² from hour 24 to hour 32,
60 μg/cm² to 90 μg/cm² from hour 32 to hour 48,
100 μg/cm² to 130 μg/cm² from hour 48 to hour 72,
200 μg/cm² to 280 μg/cm² from hour 72 to hour 144, and
60 μg/cm² to 100 μg/cm² from hour 144 to hour 168.

186. A set of transdermal therapeutic systems including at least two transdermal therapeutic systems selected from the first, second, third, fourth and fifth transdermal therapeutic system in accordance with any one of items 176 to 185.

187. Transdermal therapeutic system comprising buprenorphine for the transdermal administration of buprenorphine, wherein buprenorphine is present in the form of buprenorphine base and providing a non-cumulative release of buprenorphine base as measured in a Franz diffusion cell with dermatomed human skin of 2 μg/cm² to 10 μg/cm² in the first 8 hours,
20 μg/cm² to 80 μg/cm² from hour 8 to hour 24,
20 μg/cm² to 80 μg/cm² from hour 24 to hour 32,
30 μg/cm² to 120 μg/cm² from hour 32 to hour 48,
40 μg/cm² to 150 μg/cm² from hour 48 to hour 72,
100 μg/cm² to 300 μg/cm² from hour 72 to hour 144, and
30 μg/cm² to 100 μg/cm² from hour 144 to hour 168.

188. Transdermal therapeutic system in accordance with item 187, comprising a buprenorphine base-containing self-adhesive layer structure comprising A) a buprenorphine base-impermeable backing layer, and
B) a buprenorphine base-containing pressure-sensitive adhesive layer on said buprenorphine base-impermeable backing layer, the adhesive layer comprising
  a) at least one polymer-based pressure-sensitive adhesive, and
  b) an analgesically effective amount of buprenorphine base, wherein said buprenorphine base-containing pressure-sensitive adhesive layer is the skin contact layer.

189. Transdermal therapeutic system comprising buprenorphine for the transdermal administration of buprenorphine, wherein buprenorphine is present in the form of buprenorphine base and providing a non-cumulative release of buprenorphine base as measured in a Franz diffusion cell with dermatomed human skin of 2 μg/cm² to 10 μg/cm² in the first 8 hours,
20 μg/cm² to 80 μg/cm² from hour 8 to hour 24,
20 μg/cm² to 80 μg/cm² from hour 24 to hour 32,
30 μg/cm² to 120 μg/cm² from hour 32 to hour 48,
40 μg/cm² to 150 μg/cm² from hour 48 to hour 72,
100 μg/cm² to 300 μg/cm² from hour 72 to hour 144, and
30 μg/cm² to 100 μg/cm² from hour 144 to hour 168, and comprising a buprenorphine base-containing self-adhesive layer structure comprising A) a buprenorphine base-impermeable backing layer, and
B) a buprenorphine base-containing pressure-sensitive adhesive layer on said buprenorphine base-impermeable backing layer, the adhesive layer comprising
  a) at least one polymer-based pressure-sensitive adhesive,
  b) an analgesically effective amount of buprenorphine base, and
  c) a carboxylic acid selected from the group consisting of oleic acid, linoleic acid, linolenic acid, levulinic acid and mixtures thereof, in an amount sufficient so that said analgesically effective amount of buprenorphine base is solubilized therein to form a mixture, and the carboxylic acid buprenorphine base solution forms dispersed deposits in the said pressure-sensitive adhesive, wherein said buprenorphine base-containing pressure-sensitive adhesive layer is the skin contact layer.

190. Transdermal therapeutic system in accordance with any one of items 1 to 189 for use in a method of treating pain.

191. Transdermal therapeutic system in accordance with any one of items 1 to 189 for use in a method of treating pain by applying a transdermal therapeutic system for more than 96 hours on the skin of a patient.

192. Transdermal therapeutic system in accordance with any one of items 1 to 189 for use in a method of treating pain by applying a transdermal therapeutic system for more than 4 days on the skin of a patient.
193. Transdermal therapeutic system in accordance with any one of items 1 to 189 for use in a method of treating pain by applying a transdermal therapeutic system for about 120 hours on the skin of a patient.
194. Transdermal therapeutic system in accordance with any one of items 1 to 189 for use in a method of treating pain by applying a transdermal therapeutic system for 5 days on the skin of a patient.
195. Transdermal therapeutic system in accordance with any one of items 1 to 189 for use in a method of treating pain by applying a transdermal therapeutic system for about 144 hours on the skin of a patient.
196. Transdermal therapeutic system in accordance with any one of items 1 to 189 for use in a method of treating pain by applying a transdermal therapeutic system for 6 days on the skin of a patient.
197. Transdermal therapeutic system in accordance with any one of items 1 to 189 for use in a method of treating pain by applying a transdermal therapeutic system for about 168 hours on the skin of a patient.
198. Transdermal therapeutic system in accordance with any one of items 1 to 189 for use in a method of treating pain by applying a transdermal therapeutic system for 7 days on the skin of a patient.
199. Transdermal therapeutic system in accordance with any one of items 1 to 189 for use in a method of treating pain by applying a transdermal therapeutic system for a week on the skin of a patient.
200. Method of treating pain in a patient by applying a transdermal therapeutic system in accordance with any one of items 1 to 189 for more than 96 hours on the skin of a patient.
201. Method of treating pain in a patient by applying a transdermal therapeutic system in accordance with any one of items 1 to 189 for more than 4 days on the skin of a patient.
202. Method of treating pain in a patient by applying a transdermal therapeutic system in accordance with any one of items 1 to 189 for about 120 hours on the skin of a patient.
203. Method of treating pain in a patient by applying a transdermal therapeutic system in accordance with any one of items 1 to 189 for 5 days on the skin of a patient.
204. Method of treating pain in a patient by applying a transdermal therapeutic system in accordance with any one of items 1 to 189 for about 144 hours on the skin of a patient.
205. Method of treating pain in a patient by applying a transdermal therapeutic system in accordance with any one of items 1 to 189 for 6 days on the skin of a patient.
206. Method of treating pain in a patient by applying a transdermal therapeutic system in accordance with any one of items 1 to 189 for about 168 hours on the skin of a patient.
207. Method of treating pain in a patient by applying a transdermal therapeutic system in accordance with any one of items 1 to 189 for 7 days on the skin of a patient.
208. Method of treating pain in a patient by applying a transdermal therapeutic system in accordance with any one of items 1 to 189 for a week on the skin of a patient.
209. Use of a transdermal therapeutic system in accordance with any one of items 1 to 199 for the manufacture of a medicament for the treatment of pain.
210. Use of a transdermal therapeutic system for the manufacture of a medicament in a method of treating pain in accordance with any one of claims 200 to 208.
211. Method of manufacture of a transdermal therapeutic system for the transdermal administration of buprenorphine in accordance with any one of items 1 to 199, comprising the steps of
1. providing a buprenorphine-containing adhesive mixture or solution comprising
   a) buprenorphine base or a pharmaceutically acceptable salt thereof
   b) a carboxylic acid,
   c) a polymer-based pressure-sensitive adhesive, and
   d) solvent
2. coating said buprenorphine-containing adhesive mixture or solution on a film in an amount to provide the desired coating dry weight,
3. drying said coated buprenorphine-containing adhesive mixture or solution to provide a buprenorphine-containing adhesive layer with the desired coating dry weight,
4. laminating said buprenorphine-containing adhesive layer to a backing layer to provide an buprenorphine-containing self-adhesive layer structure,
5. punching the individual systems from the buprenorphine-containing self-adhesive layer structure with the desired area of release, and
6. optionally adhering to the individual systems an active-free self-adhesive layer structure comprising also a backing layer and an active agent-free pressure-sensitive adhesive layer and which is larger than the individual systems of buprenorphine-containing self-adhesive layer structure.
212. Method in accordance with item 211, wherein in step 1 buprenorphine is present in the form of buprenorphine base and the carboxylic acid is levulinic acid and are suspended in ethanol and subsequently combined with a polymer-based pressure-sensitive adhesive based on polysiloxane in heptane to provide the buprenorphine-containing adhesive mixture or solution.
213. Method of treating pain in a patient by applying for about 168 hours on the skin of a patient a transdermal therapeutic system for the transdermal administration of buprenorphine, comprising a buprenorphine-containing self-adhesive layer structure comprising
   A) a buprenorphine-impermeable backing layer, and
   B) a buprenorphine-containing pressure-sensitive adhesive layer on said buprenorphine-impermeable backing layer, the adhesive layer comprising
      a) at least one polymer-based pressure-sensitive adhesive,
      b) an analgesically effective amount of buprenorphine base or a pharmaceutically acceptable salt thereof, and
      c) a carboxylic acid selected from the group consisting of oleic acid, linoleic acid and linolenic acid, levulinic acid and mixtures thereof, in an amount sufficient so that said analgesically effective amount of buprenorphine is solubilized therein to form a mixture, and the carboxylic acid buprenorphine mixture forms dispersed deposits in the said pressure-sensitive adhesive,
wherein said buprenorphine-containing pressure-sensitive adhesive layer is the skin contact layer.
214. Transdermal therapeutic system for administration of buprenorphine, comprising a buprenorphine-containing self-adhesive layer structure comprising A) a buprenorphine-impermeable backing layer, and
B) a buprenorphine-containing pressure-sensitive adhesive layer on said buprenorphine-impermeable backing layer, the adhesive layer comprising
   a) at least one polymer-based pressure-sensitive adhesive,
   b) an analgesically effective amount of buprenorphine base or a pharmaceutically acceptable salt thereof, and
   c) a carboxylic acid selected from the group consisting of oleic acid, linoleic acid, linolenic acid, levulinic acid and mixtures thereof, in an amount sufficient so that said analgesically effective amount of buprenorphine is solubilized therein to form a mixture, and the carboxylic acid buprenorphine mixture forms dispersed deposits in the said pressure-sensitive adhesive, wherein said buprenorphine-containing pressure-sensitive adhesive layer is the skin contact layer for use in a method of treating pain by applying said transdermal therapeutic system for about 168 hours on the skin of a patient.

215. Transdermal therapeutic system for the transdermal administration of buprenorphine base, comprising a buprenorphine base-containing self-adhesive layer structure comprising
A) a buprenorphine base-impermeable backing layer, and
B) a buprenorphine base-containing pressure-sensitive adhesive layer on said buprenorphine base-impermeable backing layer, the adhesive layer comprising
   a) at least one pressure-sensitive adhesive based on polysiloxane,
   b) an analgesically effective amount of buprenorphine base, and
   c) levulinic acid, in an amount sufficient so that said analgesically effective amount of buprenorphine base is solubilized therein to form a mixture, and the levulinic acid buprenorphine base mixture forms dispersed deposits in the said pressure-sensitive adhesive, wherein said buprenorphine base-containing pressure-sensitive adhesive layer is the skin contact layer.

216. Method of treating pain in a patient by applying to the skin of said patient for about 168 hours a transdermal therapeutic system, comprising a buprenorphine base-containing self-adhesive layer structure comprising
A) a buprenorphine base-impermeable backing layer, and
B) a buprenorphine base-containing pressure-sensitive adhesive layer on said buprenorphine base-impermeable backing layer, the adhesive layer comprising
   a) at least one pressure-sensitive adhesive based on polysiloxane,
   b) an analgesically effective amount of buprenorphine base, and
   c) levulinic acid, in an amount sufficient so that said analgesically effective amount of buprenorphine base is solubilized therein to form a mixture, and the levulinic acid buprenorphine base mixture forms dispersed deposits in the said pressure-sensitive adhesive, wherein said buprenorphine base-containing pressure-sensitive adhesive layer is the skin contact layer.

217. Transdermal therapeutic system for the transdermal administration of buprenorphine base, comprising a buprenorphine base-containing self-adhesive layer structure comprising
A) a buprenorphine base-impermeable backing layer, and
B) a buprenorphine base-containing pressure-sensitive adhesive layer on said buprenorphine base-impermeable backing layer, the adhesive layer comprising
   a) at least one pressure-sensitive adhesive based on polysiloxane,
   b) an analgesically effective amount of buprenorphine base, and
   c) levulinic acid, in an amount sufficient so that said analgesically effective amount of buprenorphine base is solubilized therein to form a mixture, and the levulinic acid buprenorphine base mixture forms dispersed deposits in the said pressure-sensitive adhesive, wherein said buprenorphine base-containing pressure-sensitive adhesive layer is the skin contact layer for use in a method of treating pain by applying said transdermal therapeutic system for about 168 hours on the skin of a patient.

218. Transdermal therapeutic system for the transdermal administration of buprenorphine, comprising a buprenorphine-containing self-adhesive layer structure comprising
A) a buprenorphine-impermeable backing layer, and
B) a buprenorphine-containing pressure-sensitive adhesive layer on said buprenorphine-impermeable backing layer, the adhesive layer comprising
   a) at least one polymer-based pressure-sensitive adhesive,
   b) an analgesically effective amount of buprenorphine base or a pharmaceutically acceptable salt thereof, and
   c) a carboxylic acid selected from the group consisting of oleic acid, linoleic acid, linolenic acid, levulinic acid and mixtures thereof, in an amount sufficient so that said analgesically effective amount of buprenorphine is solubilized therein to form a mixture, and the carboxylic acid buprenorphine solution forms dispersed deposits in the said pressure-sensitive adhesive, wherein said buprenorphine-containing pressure-sensitive adhesive layer is the skin contact layer and contains more than about 0.55 mg/cm$^2$ or more than 0.6 mg/cm$^2$ of buprenorphine base or an equimolar amount of a pharmaceutically acceptable salt thereof.

219. Method of treating pain in a patient by applying to the skin of said patient for about 168 hours a transdermal therapeutic system for the transdermal administration of buprenorphine, comprising a buprenorphine-containing self-adhesive layer structure comprising
A) a buprenorphine-impermeable backing layer, and
B) a buprenorphine-containing pressure-sensitive adhesive layer on said buprenorphine-impermeable backing layer, the adhesive layer comprising
   a) at least one polymer-based pressure-sensitive adhesive,
   b) an analgesically effective amount of buprenorphine base or a pharmaceutically acceptable salt thereof, and
   c) a carboxylic acid selected from the group consisting of oleic acid, linoleic acid, linolenic acid, levulinic acid and mixtures thereof, in an amount sufficient so that said analgesically effective amount of buprenorphine is solubilized therein to form a mixture, and the carboxylic acid buprenorphine solution forms dispersed deposits in the said pressure-sensitive adhesive, wherein said buprenorphine-containing pressure-sensitive adhesive layer is the skin contact layer and contains more than about 0.55 mg/cm$^2$ or more than 0.6 mg/cm$^2$ of buprenorphine base or an equimolar amount of a pharmaceutically acceptable salt thereof.

220. Transdermal therapeutic system for the transdermal administration of buprenorphine, comprising a buprenorphine-containing self-adhesive layer structure comprising
   A) a buprenorphine-impermeable backing layer, and
   B) a buprenorphine-containing pressure-sensitive adhesive layer on said buprenorphine-impermeable backing layer, the adhesive layer comprising
      a) at least one polymer-based pressure-sensitive adhesive,
      b) an analgesically effective amount of buprenorphine base or a pharmaceutically acceptable salt thereof, and
      c) a carboxylic acid selected from the group consisting of oleic acid, linoleic acid, linolenic acid, levulinic acid and mixtures thereof, in an amount sufficient so that said analgesically effective amount of buprenorphine is solubilized therein to form a mixture, and the carboxylic acid buprenorphine solution forms dispersed deposits in the said pressure-sensitive adhesive,
wherein said buprenorphine-containing pressure-sensitive adhesive layer is the skin contact layer and contains more than about 0.55 mg/cm$^2$ or more than 0.6 mg/cm$^2$ of buprenorphine base or an equimolar amount of a pharmaceutically acceptable salt thereof for use in a method of treating pain by applying said transdermal therapeutic system for about 168 hours on the skin of a patient.

221. Transdermal therapeutic system for the transdermal administration of buprenorphine base, comprising a buprenorphine base-containing self-adhesive layer structure comprising
   A) a buprenorphine base-impermeable backing layer, and
   B) a buprenorphine base-containing pressure-sensitive adhesive layer on said buprenorphine base-impermeable backing layer, the adhesive layer comprising
      a) at least one pressure-sensitive adhesive based on polysiloxanes,
      b) an analgesically effective amount of buprenorphine base, and
      c) levulinic acid, in an amount sufficient so that said analgesically effective amount of buprenorphine base is solubilized therein to form a mixture, and the levulinic acid buprenorphine base mixture forms dispersed deposits in the said pressure-sensitive adhesive,
wherein said buprenorphine base-containing pressure-sensitive adhesive layer is the skin contact layer and contains more than about 0.55 mg/cm$^2$ or more than 0.6 mg/cm$^2$ of buprenorphine base.

222. Method of treating pain in a patient by applying to the skin of said patient for about 168 hours a transdermal therapeutic system for the transdermal administration of buprenorphine base, comprising a buprenorphine base-containing self-adhesive layer structure comprising
   A) a buprenorphine base-impermeable backing layer, and
   B) a buprenorphine base-containing pressure-sensitive adhesive layer on said buprenorphine base-impermeable backing layer, the adhesive layer comprising
      a) at least one pressure-sensitive adhesive based on polysiloxanes,
      b) an analgesically effective amount of buprenorphine base, and
      c) levulinic acid, in an amount sufficient so that said analgesically effective amount of buprenorphine base is solubilized therein to form a mixture, and the levulinic acid buprenorphine base mixture forms dispersed deposits in the said pressure-sensitive adhesive,
wherein said buprenorphine base-containing pressure-sensitive adhesive layer is the skin contact layer and contains more than about 0.55 mg/cm$^2$ or more than 0.6 mg/cm$^2$ of buprenorphine base.

223. Transdermal therapeutic system for the transdermal administration of buprenorphine base, comprising a buprenorphine base-containing self-adhesive layer structure comprising
   A) a buprenorphine base-impermeable backing layer, and
   B) a buprenorphine base-containing pressure-sensitive adhesive layer on said buprenorphine base-impermeable backing layer, the adhesive layer comprising
      a) at least one pressure-sensitive adhesive based on polysiloxanes,
      b) an analgesically effective amount of buprenorphine base, and
      c) levulinic acid, in an amount sufficient so that said analgesically effective amount of buprenorphine base is solubilized therein to form a mixture, and the levulinic acid buprenorphine base mixture forms dispersed deposits in the said pressure-sensitive adhesive,
wherein said buprenorphine base-containing pressure-sensitive adhesive layer is the skin contact layer and contains more than about 0.55 mg/cm$^2$ or more than 0.6 mg/cm$^2$ of buprenorphine base for use in a method of treating pain by applying said transdermal therapeutic system for about 168 hours on the skin of a patient.

224. A set of two to five different transdermal therapeutic systems for the transdermal administration of buprenorphine base selected from five different transdermal therapeutic systems, a first, a second, a third, a forth and a fifth transdermal therapeutic system, each of the five different transdermal therapeutic systems comprising a buprenorphine-containing self-adhesive layer structure comprising
   A) a buprenorphine base-impermeable backing layer, and
   B) a buprenorphine base-containing pressure-sensitive adhesive layer on said buprenorphine base-impermeable backing layer, the adhesive layer comprising
      a) at least one pressure-sensitive adhesive based on polysiloxanes,
      b) an analgesically effective amount of buprenorphine base, and
      c) levulinic acid, in an amount sufficient so that said analgesically effective amount of buprenorphine base is solubilized therein to form a mixture, and the levulinic acid buprenorphine base mixture forms dispersed deposits in the said pressure-sensitive adhesive,
wherein,
the first transdermal therapeutic system provides a size of said buprenorphine-containing pressure-sensitive adhesive layer providing the area of release ranging from about 1 cm$^2$ to about 4.8 cm$^2$ and contains from about 1 mg to about 4 mg buprenorphine base;
the second transdermal therapeutic system provides a size of said buprenorphine-containing pressure-sensitive adhesive layer providing the area of release ranging from about 3 cm$^2$ to about 9.5 cm$^2$ and contains from about 3.5 mg to about 8 mg buprenorphine base; and
the third transdermal therapeutic system provides a size of said buprenorphine-containing pressure-sensitive adhesive layer providing the area of release ranging from about 6 cm² to about 19 cm² and contains from about 6.5 mg to about 16 mg buprenorphine base; and the fourth transdermal therapeutic system provides a size of said buprenorphine-containing pressure-sensitive adhesive layer providing the area of release ranging from about 12 cm² to about 28.5 cm² and contains from about 11.5 mg to about 24 mg buprenorphine base; and the fifth transdermal therapeutic system provides a size of said buprenorphine-containing pressure-sensitive adhesive layer providing the area of release ranging from about 16 cm² to about 38 cm² from about 15 mg to about 32 mg buprenorphine base, wherein the five different transdermal therapeutic systems have increasing areas of release and amounts of buprenorphine from the first to the fifth transdermal therapeutic system for use in method of treating pain by applying one of said transdermal therapeutic systems for about 168 hours on the skin of a patient.

The invention claimed is:

1. A method of treating pain in a patient comprising applying a transdermal therapeutic system for the transdermal administration of buprenorphine to the skin of the patient, wherein the transdermal therapeutic system comprises a buprenorphine-containing self-adhesive layer structure comprising
    a. a buprenorphine-impermeable backing layer, and
    b. a buprenorphine-containing pressure-sensitive adhesive layer on the buprenorphine-impermeable backing layer, the adhesive layer comprising
        i. at least one polymer-based pressure-sensitive adhesive based on polysiloxanes or polyisobutylenes,
        ii. an analgesically effective amount of buprenorphine base or a pharmaceutically acceptable salt thereof, and
        iii. a carboxylic acid selected from the group consisting of oleic acid, linoleic acid, linolenic acid, levulinic acid and mixtures thereof, in an amount sufficient so that the analgesically effective amount of buprenorphine is solubilized therein to form a mixture, and the carboxylic acid buprenorphine mixture forms dispersed deposits in the pressure-sensitive adhesive, wherein the buprenorphine-containing pressure-sensitive adhesive layer is the skin contact layer; and wherein the transdermal therapeutic system is applied on the skin of the patient for about 168 hours;
wherein the transdermal therapeutic system provides a size of the buprenorphine-containing pressure-sensitive adhesive layer providing an area of release ranging from about 1 cm² to about 4.8 cm² and contains an amount of the buprenorphine from about 1 mg to about 4 mg buprenorphine base or an equimolar amount of a pharmaceutically acceptable salt thereof, and
wherein the transdermal therapeutic system provides a mean AUCt per area of release of more than 1,700 pg.hr/ml-cm² over about 168 hours of administration after a single-dose administration to a subject population.

2. The method of claim 1, wherein the transdermal therapeutic system provides a nominal mean release rate of about 5 µg/hr over about 168 hours of administration.

3. The method of claim 1, wherein the carboxylic acid is levulinic acid and the polymer-based pressure-sensitive adhesive is based on polysiloxanes.

4. The method of claim 1, wherein the transdermal therapeutic system provides a mean AUCt of more than 7,000 pg.hr/ml over about 168 hours of administration after a single-dose administration to a subject population.

5. The method of claim 1, wherein the transdermal therapeutic system provides a mean cumulative skin permeation rate of buprenorphine measured in a Franz diffusion cell with dermatomed human skin of more than 1.3 µg/cm²-hr over a 168 hours test.

6. The method of claim 1, wherein the transdermal therapeutic system provides a cumulative release of buprenorphine as measured in a Franz diffusion cell with dermatomed human skin of 220 µg/cm² to 640 µg/cm² over a time period of 168 hours.

7. The method of claim 1, wherein the transdermal therapeutic system provides a non-cumulative release of buprenorphine as measured in a Franz diffusion cell with dermatomed human skin of
    2 µg/cm² to 10 µg/cm² in the first 8 hours,
    20 µg/cm² to 80 µg/cm² from hour 8 to hour 24,
    20 µg/cm² to 80 µg/cm² from hour 24 to hour 32,
    30 µg/cm² to 120 µg/cm² from hour 32 to hour 48,
    40 µg/cm² to 150 µg/cm² from hour 48 to hour 72,
    100 µg/cm² to 300 µg/cm² from hour 72 to hour 144, and
    30 µg/cm² to 100 µg/cm² from hour 144 to hour 168.

8. A method of treating pain in a patient comprising applying a transdermal therapeutic system for the transdermal administration of buprenorphine to the skin of the patient, wherein the transdermal therapeutic system comprises a buprenorphine-containing self-adhesive layer structure comprising
    a. a buprenorphine-impermeable backing layer, and
    b. a buprenorphine-containing pressure-sensitive adhesive layer on the buprenorphine-impermeable backing layer, the adhesive layer comprising
        i. at least one polymer-based pressure-sensitive adhesive based on polysiloxanes or polyisobutylenes,
        ii. an analgesically effective amount of buprenorphine base or a pharmaceutically acceptable salt thereof, and
        iii. a carboxylic acid selected from the group consisting of oleic acid, linoleic acid, linolenic acid, levulinic acid and mixtures thereof, in an amount sufficient so that the analgesically effective amount of buprenorphine is solubilized therein to form a mixture, and the carboxylic acid buprenorphine mixture forms dispersed deposits in the pressure-sensitive adhesive, wherein the buprenorphine-containing pressure-sensitive adhesive layer is the skin contact layer; and wherein the transdermal therapeutic system is applied on the skin of the patient for about 168 hours;
wherein the transdermal therapeutic system provides a size of the buprenorphine-containing pressure-sensitive adhesive layer providing an area of release ranging from about 3 cm² to about 9.5 cm² and contains an amount of the buprenorphine from about 3.5 mg to about 8 mg buprenorphine base or an equimolar amount of a pharmaceutically acceptable salt thereof, and
wherein the transdermal therapeutic system provides a mean AUCt per area of release of more than 1,700 pg.hr/ml-cm² over about 168 hours of administration after a single-dose administration to a subject population.

9. The method of claim 8, wherein the transdermal therapeutic system provides a nominal mean release rate of about 10 µg/hr over about 168 hours of administration.

10. The method of claim 8, wherein the carboxylic acid is levulinic acid and the polymer-based pressure-sensitive adhesive is based on polysiloxanes.

11. The method of claim 8, wherein the transdermal therapeutic system provides a mean AUCt of more than 14,000 pg.hr/ml over about 168 hours of administration after a single-dose administration to a subject population.

12. The method of claim 8, wherein the transdermal therapeutic system provides a mean cumulative skin permeation rate of buprenorphine measured in a Franz diffusion cell with dermatomed human skin of more than 1.3 µg/cm²-hr over a 168 hours test.

13. The method of claim 8, wherein the transdermal therapeutic system provides a cumulative release of buprenorphine as measured in a Franz diffusion cell with dermatomed human skin of 220 µg/cm² to 640 µg/cm² over a time period of 168 hours.

14. The method of claim 8, wherein the transdermal therapeutic system provides a non-cumulative release of buprenorphine as measured in a Franz diffusion cell with dermatomed human skin of
   2 µg/cm² to 10 µg/cm² in the first 8 hours,
   20 µg/cm² to 80 µg/cm² from hour 8 to hour 24,
   20 µg/cm² to 80 µg/cm² from hour 24 to hour 32,
   30 µg/cm² to 120 µg/cm² from hour 32 to hour 48,
   40 µg/cm² to 150 µg/cm² from hour 48 to hour 72,
   100 µg/cm² to 300 µg/cm² from hour 72 to hour 144, and
   30 µg/cm² to 100 µg/cm² from hour 144 to hour 168.

15. A method of treating pain in a patient comprising applying a transdermal therapeutic system for the transdermal administration of buprenorphine to the skin of the patient, wherein the transdermal therapeutic system comprises a buprenorphine-containing self-adhesive layer structure comprising
   a. a buprenorphine-impermeable backing layer, and
   b. a buprenorphine-containing pressure-sensitive adhesive layer on the buprenorphine-impermeable backing layer, the adhesive layer comprising
      i. at least one polymer-based pressure-sensitive adhesive based on polysiloxanes or polyisobutylenes,
      ii. an analgesically effective amount of buprenorphine base or a pharmaceutically acceptable salt thereof, and
      iii. a carboxylic acid selected from the group consisting of oleic acid, linoleic acid, linolenic acid, levulinic acid and mixtures thereof, in an amount sufficient so that the analgesically effective amount of buprenorphine is solubilized therein to form a mixture, and the carboxylic acid buprenorphine mixture forms dispersed deposits in the pressure-sensitive adhesive, wherein the buprenorphine-containing pressure-sensitive adhesive layer is the skin contact layer; and wherein the transdermal therapeutic system is applied on the skin of the patient for about 168 hours;
wherein the transdermal therapeutic system provides a size of the buprenorphine-containing pressure-sensitive adhesive layer providing an area of release ranging from about 6 cm² to about 14 cm² and contains an amount of said buprenorphine from about 6.5 mg to about 16 mg buprenorphine base or an equimolar amount of a pharmaceutically acceptable salt thereof, and
wherein the transdermal therapeutic system provides a mean AUCt per area of release of more than 1,700 pg.hr/ml-cm² over about 168 hours of administration after a single-dose administration to a subject population.

16. The method of claim 15, wherein the transdermal therapeutic system provides a nominal mean release rate of about 20 µg/hr over about 168 hours of administration.

17. The method of claim 15, wherein the carboxylic acid is levulinic acid and the polymer-based pressure-sensitive adhesive is based on polysiloxanes.

18. The method of claim 15, wherein the transdermal therapeutic system provides a mean AUCt of more than 28,000 pg.hr/ml over about 168 hours of administration after a single-dose administration to a subject population.

19. The method of claim 15, wherein the transdermal therapeutic system provides a mean cumulative skin permeation rate of buprenorphine measured in a Franz diffusion cell with dermatomed human skin of more than 1.3 µg/cm²-hr over a 168 hours test.

20. The method of claim 15, wherein the transdermal therapeutic system provides a cumulative release of buprenorphine as measured in a Franz diffusion cell with dermatomed human skin of 220 µg/cm² to 640 µg/cm² over a time period of 168 hours.

21. The method of claim 15, wherein the transdermal therapeutic system provides a non-cumulative release of buprenorphine as measured in a Franz diffusion cell with dermatomed human skin of
   2 µg/cm² to 10 µg/cm² in the first 8 hours,
   20 µg/cm² to 80 µg/cm² from hour 8 to hour 24,
   20 µg/cm² to 80 µg/cm² from hour 24 to hour 32,
   30 µg/cm² to 120 µg/cm² from hour 32 to hour 48,
   40 µg/cm² to 150 µg/cm² from hour 48 to hour 72,
   100 µg/cm² to 300 µg/cm² from hour 72 to hour 144, and
   30 µg/cm² to 100 µg/cm² from hour 144 to hour 168.

22. A method of treating pain in a patient comprising applying a transdermal therapeutic system for the transdermal administration of buprenorphine to the skin of the patient, wherein the transdermal therapeutic system comprises a buprenorphine-containing self-adhesive layer structure comprising
   a. a buprenorphine-impermeable backing layer, and
   b. a buprenorphine-containing pressure-sensitive adhesive layer on the buprenorphine-impermeable backing layer, the adhesive layer comprising
      i. at least one polymer-based pressure-sensitive adhesive based on polysiloxanes or polyisobutylenes,
      ii. an analgesically effective amount of buprenorphine base or a pharmaceutically acceptable salt thereof, and
      iii. a carboxylic acid selected from the group consisting of oleic acid, linoleic acid, linolenic acid, levulinic acid and mixtures thereof, in an amount sufficient so that the analgesically effective amount of buprenorphine is solubilized therein to form a mixture, and the carboxylic acid buprenorphine mixture forms dispersed deposits in the pressure-sensitive adhesive, wherein the buprenorphine-containing pressure-sensitive adhesive layer is the skin contact layer; and wherein the transdermal therapeutic system is applied on the skin of the patient for about 168 hours;
wherein the transdermal therapeutic system provides a size of the buprenorphine-containing pressure-sensitive adhesive layer providing an area of release ranging from about 12 cm² to about 28.5 cm² and contains an amount of the buprenorphine from about 11.5 mg to about 24 mg buprenorphine base or an equimolar amount of a pharmaceutically acceptable salt thereof, and
wherein the transdermal therapeutic system provides a mean AUCt per area of release of more than 1,700 pg.hr/ml-cm² over about 168 hours of administration after a single-dose administration to a subject population.

23. The method of claim 22, wherein the transdermal therapeutic system provides a nominal mean release rate of about 30 μg/hr over about 168 hours of administration.

24. The method of claim 22, wherein the carboxylic acid is levulinic acid and the polymer-based pressure-sensitive adhesive is based on polysiloxanes.

25. The method of claim 22, wherein the transdermal therapeutic system provides a mean AUCt of more than 42,000 pg.hr/ml over about 168 hours of administration after a single-dose administration to a subject population.

26. The method of claim 22, wherein the transdermal therapeutic system provides a mean cumulative skin permeation rate of buprenorphine measured in a Franz diffusion cell with dermatomed human skin of more than 1.3 μg/cm$^2$-hr over a 168 hours test.

27. The method of claim 22, wherein the transdermal therapeutic system provides a cumulative release of buprenorphine as measured in a Franz diffusion cell with dermatomed human skin of 220 μg/cm$^2$ to 640 μg/cm$^2$ over a time period of 168 hours.

28. The method of claim 22, wherein the transdermal therapeutic system provides a non-cumulative release of buprenorphine as measured in a Franz diffusion cell with dermatomed human skin of
2 μg/cm$^2$ to 10 μg/cm$^2$ in the first 8 hours,
20 μg/cm$^2$ to 80 μg/cm$^2$ from hour 8 to hour 24,
20 μg/cm$^2$ to 80 μg/cm$^2$ from hour 24 to hour 32,
30 μg/cm$^2$ to 120 μg/cm$^2$ from hour 32 to hour 48,
40 μg/cm$^2$ to 150 μg/cm$^2$ from hour 48 to hour 72,
100 μg/cm$^2$ to 300 μg/cm$^2$ from hour 72 to hour 144, and
30 μg/cm$^2$ to 100 μg/cm$^2$ from hour 144 to hour 168.

* * * * *